US006894068B2

(12) United States Patent
Michejda et al.

(10) Patent No.: US 6,894,068 B2
(45) Date of Patent: May 17, 2005

(54) SUBSTITUTED BENZIMIDAZOLES AS NON-NUCLEOSIDE INHIBITORS OF REVERSE TRANSCRIPTASE

(75) Inventors: Christopher J. Michejda, North Potomac, MD (US); Marshall Morningstar, San Diego, CA (US); Thomas Roth, Hochheim (DE)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 159 days.

(21) Appl. No.: 10/119,634

(22) Filed: Apr. 9, 2002

(65) Prior Publication Data

US 2003/0191160 A1 Oct. 9, 2003

Related U.S. Application Data

(63) Continuation of application No. 09/380,171, filed as application No. PCT/US98/03588 on Feb. 24, 1998, now Pat. No. 6,369,235.
(60) Provisional application No. 60/038,509, filed on Feb. 25, 1997, now abandoned.

(51) Int. Cl.[7] .................. A61K 31/415; A61K 31/70; A61K 31/495; A61K 31/47; A61K 43/42
(52) U.S. Cl. .................. 514/393; 514/50; 514/365; 514/307; 514/253.01
(58) Field of Search .................. 514/393, 50, 365, 514/307, 253.01

(56) References Cited

U.S. PATENT DOCUMENTS

| 3,825,537 A | 7/1974 | Haugwitz et al. ....... 514/369 X |
| 4,214,089 A | 7/1980 | Fenichel et al. ............. 548/151 |
| 4,434,288 A | 2/1984 | Wike ............................ 544/54 |
| 4,912,219 A | 3/1990 | Manoury et al. ............ 544/321 |
| 5,217,984 A | 6/1993 | Monforte et al. ........... 514/366 |
| 5,356,917 A | 10/1994 | Panetta ....................... 514/369 |
| 5,360,795 A | 11/1994 | Townsend et al. ............. 514/43 |
| 5,468,765 A | 11/1995 | Banks et al. ................. 514/395 |
| 5,545,653 A | 8/1996 | Miller et al. ................. 514/388 |
| 5,606,060 A | 2/1997 | Pommier et al. ............. 546/85 |
| 5,622,960 A | 4/1997 | Pommier et al. ........... 514/287 |
| 5,712,255 A | 1/1998 | Townsend et al. ............ 514/43 |
| 5,747,520 A | 5/1998 | Pommier et al. ........... 514/412 |
| 5,821,242 A | 10/1998 | Colacino et al. ......... 514/227.2 |

FOREIGN PATENT DOCUMENTS

| EP | 0471991 | 2/1992 |
| FR | 2092648 | 1/1972 |
| FR | 2096648 | 1/1972 |
| WO | WO 94/10175 | 5/1994 |
| WO | WO 95/08540 | 3/1995 |
| WO | WO 95/19772 | 7/1995 |
| WO | WO 97/25337 | 7/1997 |
| WO | WO 98/55120 | 12/1998 |

OTHER PUBLICATIONS

Roth et al., *J. Medicinal Chem.*, 40(26):4199–4207 (1997).
Balzarini et al., *Proc. Natl. Acad. Sci. USA*, 89:4392–4396 (1992).
Boyer et al., *J. Virol.*, 67:2412–2420 (1993).
Buckheit et al., *Antiviral Res.*, 21:247–265 (1993).
Buckheit et al., *Antiviral Res.*, 26:117–132 (1995).
Chimirri et al., *Il Farmaco*, 46:817–823 (1991).
Chimirri et al., *Il Farmaco*, 46:925–933 (1991).
Chimirri et al., "Thiazobenzimidazoles as Non–Nucleoside HIV–1 RT Inhibitors", Abs. Il Congresso Congiunto Italiano–Spagnolo di Chemica Farmaceutica, Aug. 30–Sep. 3, (1995), ML20.
Cloyd, *Medical Microbiology*, University of Texas Medical Branch at Galveston, pp. 761–775 (1996).
De Clercq, *Biochem. Pharm.*, 47:155–169 (1994).
Ding et al., *Structure*, 3:365–379 (1995).
Ding et al., *Nature Struct. Biol.*, 2:407–415 (1995).
El Dareer et al., *Drug Metabol. Dispos.*, 21:231–235.
Famighetti, *1996 World Almanac and Book of Facts*, World Almanac Books, Mahwah, NJ (1995), p. 840.
Fenichel et al., *Jour. Immunopharmacol.*, 2(4):491–508 (1980).
Gartner and Popovic, *Techniques in HIV Research*, Stockton Press, NY, pp. 69–63 (1991).
Gilbert et al., *Antiviral Res.*, 9:355–365 (1998).
Goldman et al., *Proc. Natl. Acad. Sci. USA*, 88:6863–6867 (1991).
Merluzzi et al., *Science*, 250:1411–1413 (1990).
Nanni et al., *Perspect. Drug Discov. Des.*, 1:129–150 (1993).
Nara and Fischinger, *Nature*, 332:469–470 (1988).
Nunberg et al., *J. Virol.*, 65:4887–4892 (1991).
Patel et al., *Biochem.*, 34:5351–5363 (1995).
Pauwels et al., *Antimicrob. Agents Chemother.*, 38:2863–2870 (1994).
Pauwels et al., *Nature*, 343:470–474 (1990).
Pauwels et al., *Proc. Natl. Acad. Sci., USA*, 90:1711–1715 (1993).
Richman, *Agents Chemother.*, 37:1207–1213 (1993).
Romero et al., *Proc. Natl. Acad. Sci., USA*, 88:8806–8810 (1991).
Smith et al., *Prot. Sci.*, 4:2203–2222 (1995).
Tantillo et al., *J. Mol. Biol.*, 243:369–387 (1994).
Warren et al., *immunopharmacol.*, 1:269–276 (1979).

(Continued)

*Primary Examiner*—Russell Travers
(74) *Attorney, Agent, or Firm*—Peter F. Corless; Christine C. O'Day

(57) ABSTRACT

The present invention provides compositions and methods for the treatment of HIV infection. In particular, the present invention provides non-nucleoside inhibitors of reverse transcriptase (RT), as well as methods to treat HIV infection using these non-nucleoside inhibitors of RT. In preferred embodiments, the present invention provides a novel class of substituted benzimidazoles, effective in the inhibition of human immunodeficiency virus (HIV) RT.

11 Claims, 20 Drawing Sheets

OTHER PUBLICATIONS

Yang et al., *Leukemia*, 9:S75–S85 (1995).
Young, *Perspect. Drug Discov. Des.*, 1:181–192 (1993).
Clark et al., *Meth. In Enzymol.*, 262:171–185 (1995).
Eymin et al., *Int. J. Cancer*, 63(2):268–275 (1995).
Goker et al., *Arch Pharm.* (Weinheim), 328(5):425–430 (1995).
Jacobo–Molina et al., *Biochem.*, 30(26):6351–6356 (1991).
Leteurtre et al., *Cancer Res.*, 52:4478–4483 (1992).
Leteurtre et al., *Biochem. Pharmacol.*, 49(9):1283–1290 (1995).
Solary et al., *Biochem. Pharmacol.*, 45(12):2449–2456 (1993).
Chimirri et al., *Il Farmaco*, 51(4):279–282 (Apr., 1996).
Roth et al., *J. Med. Chem.*, 40:4199–4207 (Dec. 19, 1997).
Smith et al., *J. Med. Chem.*, 41(26):5272–5286 (1998).
Chimirri et al., *Abst. Il Congresso Italiano–Spagnolo di Chimica farmaceutica*, Ferrara, Italy, Aug. 30–Sep. 3, 1995, ML20.

IMIDAZOLE

BENZIMIDAZOLE

1 X=H
3 X=CH₃

2 X=H, R'=CH₂OH
4 X=CH₃, R'=CH₂OH
5 X=CH₃, R'=CH₂OTBDMS
6 X=CH₃, R'=iPr

31 X=H, R'=CH₂OTBDMS
32 X=H, R'=CH₂O(2,6-F₂Bn)
48 X=CH₃, R'=CH₂OH
49 X=CH₃, R'=H
50 X=CH₃, R'=CHO
34 X=CH₃, R'=iPr
35 X=H, R'=CH₃
39 X=H, R'=Ph

39

TBZ

A

B

A

B

4008 X=CH₂CH₃
9    X=CH₃

4009 X=CH₂CH₃, R=2,6-F₂Ph
6001 X=CH₃, R=2,6-F₂Ph

4010 X=CH₂CH₃, R'=H
4011 X=CH₂,CH₃, R'=2,6-F₂Bn  ⎤ c
6002 X=CH₃, R'=H
6003 X=CH₃, R'=CH₂-CH=C(CH₃)₂ ⎤ d

5008 X'=NO₂, X"=OCH₃
5009 X'=NH₂, X"=OCH₃  a

5010 X'=HNAc, X"=F
5011 X'=MeNAc, X"=F  b
5012 X'=MeNH, X"=F  c

4012  X=NO₂, R=H

4013  X=NO₂, R=CH₂-CH=C(CH₃)₂

4014  X=NH₂, R=CH₂-CH=C(CH₃)₂

4015  X=C(OH)(CH₃)₂, R=2,6-F₂Bn

4016  X=isopropenyl, R=2,6-F₂Bn

SUBSTITUTED BENZIMIDAZOLES AS NON-NUCLEOSIDE INHIBITORS OF REVERSE TRANSCRIPTASE

The present application is a Continuation of U.S. Ser. No. 09/380,171, filed Feb. 1, 2000 which issued as U.S. Pat. No. 6,369,235 on Apr. 9, 2002, which in turn was a 371 of PCT/US98/03588 filed on Feb. 24, 1998, which claimed the priority benefit of U.S. provisional application No. 60/038,509, filed Feb. 25, 1997, abandoned.

This invention was made during the course of work supported by the United States Government, at the National Cancer Institute under the National Institutes of Health. As such, the United States Government may have certain rights to this invention.

FIELD OF THE INVENTION

The present invention is related to non-nucleoside inhibitors of reverse transcriptase (RT). In particular, the present invention relates to a novel class of substituted benzimidazoles effective in the inhibition of human immunodeficiency virus (HIV) RT.

BACKGROUND OF THE INVENTION

Since its recognition in 1981, the acquired immunodeficiency syndrome (AIDS) has become a major pandemic. The worldwide prevalence of HIV infection has been, estimated at more than 18,500,000 cases, with an additional estimate of 1.5 million infected children (R. Famighetti, 1996 *World Almanac and Book of Facts*, World Almanac Books, Mahwah, N.J., [1995], p. 840).

The etiologic agent associated with AIDS was identified as the human immunodeficiency virus (HIV). HIV is classified as a retrovirus, as it contains reverse transcriptase (RT), a multi-functional enzyme that contains RNA-dependent DNA polymerase activity, as well as DNA-dependent DNA polymerase and ribonuclease H activities. These three activities are essential for the conversion of genomic retroviral RNA into double-stranded DNA that can then be integrated into an infected host cell genome.

HIV is a D-type virus within the lentivirus family, with two major antigenic types (HIV-1 and HIV-2). HIV-1 and HIV-2 share approximately 40% genetic identity, although they can be readily distinguished based on differences in antibody reactivity to the envelope glycoprotein (M. Cloyd, "Human Retroviruses," in S. Baron (ed.), *Medical Microbiology*, University of Texas Medical Branch at Galveston, [1996], pp. 761–775). Both HIV-1 and HIV-2 have been associated with AIDS.

The search for effective drugs against HIV has focused on targeting various critical components of the replication cycle of HIV-1. One important component in this cycle is the reverse transcriptase enzyme. Indeed, perhaps because of its pivotal role in the life cycle of HIV, it was the target of the first clinically approved anti-retroviral agents (see, Patel et al., "Insights into DNA Polymerization Mechanisms from Structure and Function Analysis of HIV-1 Reverse Transcriptase," *Biochem.*, 34:5351–5363 [1995]), although other compounds such as protease inhibitors have recently been introduced. In addition to its critical role in HIV replication, targeting RT has a potential benefit in reducing the toxicity to the patient associated with many drugs, as human cells do not normally contain this RT activity. Therefore, the potential for targeted inhibition of only viral replication and not host cell multiplication is present. However, this potential has yet to be realized.

There are two major classes of RT inhibitors. The first comprises nucleoside analogues, such as 3'-azido-3'-deoxythymidine (AZT), 2',3'-didehydro-2',3'-dideoxythymidine (d4T), and 2',3'-dideoxycytidine (ddC). These compounds are analogs of normal deoxynucleoside triphosphates (dNTPs). However, these are not specific for HIV RT, and are incorporated into cellular DNA by host DNA polymerases; thus, these compounds can cause serious side effects. Moreover, administration of these analogs has resulted in the emergence of drug-resistant viral strains that contain mutations in their RT. Thus, these RT inhibitors have dangers that must be considered in developing treatment regimens for HIV-infected patients.

The second major class of RT inhibitors comprises the non-nucleoside RT inhibitors (NNRTI), such as tetrahydroimidazo(4,5,1-1-jk)(1,4)-benzodiazepin-2-(1H)-one, and -thione (TIBO) derivatives, dipyridodiazepinones, pyridinones, bis(heteroaryl)piperazines (BHAPs), 2',5'-bis-O-(tertbutyldimethylsilyl)-3'-spiro-5"-(4"-amino-1",2"-oxathiole-2",2"-dioxide)pyrimidine (TSAO) derivatives, α-anilinophenylacetamide (α-APA), 8-chloro-4,5,6,7-tetrahydro-5-methylimidazo-[4,5,1-jk][1,4]benzodiazepine-2 (1H)-one (8-Cl TIBO), and nevirapine. (See, e.g., Pauwels et al., "Potent and Selective Inhibition of HIV-1 Replication in Vitro By a Novel Series of TIBO Derivatives," *Nature* 343:470–474 [1990]; Merluzzi et al., "Inhibition of HIV-1 Replication by a Non-Nucleoside Reverse Transcriptase Inhibitor," *Science* 250:1411–1413 [1990]; Goldman and Stern, "Pyridinone Derivatives: Specific Human Immunodeficiency Virus Type 1 Reverse Transcriptase Inhibitors with Antiviral Activity," *Proc. Natl. Acad. Sci. USA* 88:6863–6867 [1991]; Romero and Tarpley, "Non-Nucleoside Reverse Transcriptase Inhibitors that Potently and Specifically Block Human Immunodeficiency Virus Type 1 Replication," *Proc. Natl. Acad. Sci., USA* 88:8806–8810 [1991]; Balzarini et al., "2',3'-Bis-O-(Tertbutyldimethylsilyl)-3'-Spiro-5"-(4"-Amino-1",2"-Oxathiole-2",2"-Dioxide) Pyrimidine (TSAO) Nucleoside Analogs: Highly Selective Inhibitors of Human Immunodeficiency Virus Type 1 That are Targeted at the Viral Reverse Transcriptase," *Proc. Natl. Acad. Sci. USA* 89:4392–4396 [1992]; Young, "Non-Nucleoside Inhibitors of HIV-1 Reverse Transcriptase," *Perspect. Drug Discov. Des.*, 1:181–192; and Pauwels et al., "Potent and Highly Selective Human Immunodeficiency Virus Type 1 (HIV-1) Inhibition by a Series of α-Anilinophenylacetamide Derivatives Targeted at HIV-1 Reverse Transcriptase," *Proc. Natl. Acad. Sci., USA* 90:1711–1715 [1993]).

Unlike the nucleoside analogues, the NNRTIs do not act as chain terminators and do not bind at the dNTP-binding site. The majority of these compounds have been shown to share a common binding site unique to HIV-1 RT that is located in proximity to the RT polymerase active site. (See, Tantillo et al., "Locations of Anti-AIDS Drug Binding Sites and Resistance Mutations in Three-Dimensional Structure of HIV-1 Reverse Transcriptase. Implications for Mechanisms of Drug Inhibition and Resistance," *J. Mol. Biol.*, 243:369–387 [1994]; Smith et al., "Molecular Modeling Studies of HIV-1 Reverse Transcriptase Nonnucleoside Inhibitors: Total Energy of Complexation as a Predictor of Drug Placement and Activity," *Prot. Sci.*, 4:2203–2222 [1995]; Ding et al., "Structure of HIV-1 TR/TIBO R86183 Complex Reveals Remarkable Similarity in the Binding of Diverse Nonnucleoside Inhibitors," *Nature Struct. Biol.*, 2:407–415 [1995]; and Nanni et al., "Review of HIV-1 Reverse Transcriptase Three Dimensional Structure: Implications for Drug Design," *Perspect. Drug Discov. Des.*, 1:129–150 [1993]).

NNRTIs are highly specific for HIV-1 RT, and do not inhibit either HIV-2 RT or normal cellular polymerases, resulting in lower cytotoxicity and fewer side effects than the nucleoside analogs. (See, e.g., Ding et al., "Structure of HIV-1 Reverse Transcriptase in a Complex with the Non-Nucleoside Inhibitor α-APA R 95845 at 2.8 Å Resolution," *Structure* 3:365–379 [1995]). However, resistance to some of these compounds has been reported. (See, e.g., Nunberg et al., "Viral Resistance to Human Immunodeficiency Virus Type 1-Specific Pyridinone Reverse Transcriptase Inhibitors," *J. Virol.*, 65:4887–4892 [1991]; Tantillo et al., "Locations of Anti-AIDS Drug Binding Sites and Resistance Mutations in the Three-Dimensional Structure of HIV-1 Reverse Transcriptase: Implications for Mechanisms of Drug Inhibition and Resistance," *J. Mol. Biol.*, 243:369–387; and Richman, "Resistance of Clinical Isolates of Human Immunodeficiency Virus to Antiretroviral Agents," *Antimicrob. Agents Chemother.*, 37:1207–1213 [1993]).

Despite recent developments in drug and compound design to combat HIV, there remains a need for a potent, non-toxic compound that is effective against wild type (WT) RTs, as well as RTs that have undergone mutations, and thereby become refractory to commonly used anti-HIV compounds.

SUMMARY OF THE INVENTION

The present invention is related to substituted benzimidazole compounds. In particular, the present invention provides non-nucleoside inhibitors of reverse transcriptase (RT) comprising a novel class of substituted benzimidazoles effective in the inhibition of human immunodeficiency virus (HIV) RT.

In one embodiment, the present invention provides substituted benzimidazoles having the structure of FIG. 7A. In one embodiment, X" is selected from the group consisting of hydrogen, methyl, ethyl, cyano, methoxyl, nitro, amine, acetamide, methylamine, dimethylamine, isopropyl, isopropenyl, bromine and chlorine. In another embodiment, R" is selected from the group consisting of 2,6-difluorobenzyl (2,6-$F_2$Bn), benzyl (Bn), ethylbenzyl, 2,6-dichlorobenzyl (2,6-$Cl_2$Bn), 2,3,4,5,6-pentafluorobenzyl (2,3,4,5,6-$F_5$Bn), pyridylmethyl ($CH_2$(3-Py), benzenesulfonyl (Ph$SO_2$), 2,6-difluorobenzoyl (2,6-$F_2$Bz), and 3,3-dimethylallyl. In yet another embodiment, X" is selected from the group consisting of hydrogen, methyl, ethyl, cyano, methoxyl, nitro, amine, acetamide, methylamine, dimethylamine, isopropyl, isopropenyl, bromine and chlorine; and R" is selected from the group consisting of 2,6-difluorobenzyl, benzyl, ethylbenzyl, 2,6-dichlorobenzyl, 2,3,4,5,6-pentafluorobenzyl, pyridylmethyl, benzenesulfonyl, 2,6-difluorobenzoyl, and 3,3-dimethylallyl. In a preferred embodiment, R" is 2,6-difluorobenzyl.

In an alternative embodiment, the present invention provides substituted benzimidazoles with the general structure of FIG. 7B. In one embodiment, X' is selected from the group consisting of hydrogen, methyl, ethyl, cyano, methoxyl, nitro, amine, acetamide, methylamine, dimethylamine, isopropyl, isopropenyl, bromine and chlorine. In another embodiment, R' is selected from the group consisting of phenyl (Ph), formyl (CHO), isopropyl (iPr), H, methyl ($CH_3$), cyclopropyl, hydroxymethyl ($CH_2OH$), and 2,6-difluorobenzyloxymethyl ($CH_2O(2,6-F_2Bn)$, 2,6 difluorophenyl (2,6-$F_2$Ph), methylphenyl (2-$CH_3$Ph), 2-fluoro-6-methoxylphenyl, pyridyl (e.g., 4-Py, 3-Py), and naphthyl (e.g., 1-Nap, 2-Nap). In yet another embodiment, X' is selected from the group consisting of hydrogen and methyl, ethyl, cyano, methoxyl, nitro, amine, acetamide, methylamine, dimethylamine, isopropyl, isopropenyl, bromine and chlorine; and R' is selected from the group consisting of phenyl, formyl, isopropyl, H, methyl, cyclopropyl, hydroxymethyl, 2,6-difluorobenzyloxymethyl, 2,6 difluorophenyl (2,6-$F_2$Ph), methylphenyl (2-$CH_3$Ph), 2-fluoro-6-methoxylphenyl, pyridyl (e.g., 4-Py, 3-Py), and naphthyl (e.g., 1-Nap, 2-Nap). In a preferred embodiment, R' is 2,6-difluorophenyl.

In another alternative embodiment, the present invention provides substituted benzimidazoles with the general structure of FIG. 13A, wherein X"" is at least one substituent positioned at a benzimidazole carbon of a substituted 1-(2, 6-difluorobenzyl)-2-(2,6-difluorophenyl)benzimidazole and selected from C4, C5, C6, C7, C4 and C5, and C4 and C6 of the substituted 1-(2,6-difluorobenzyl)-2-(2,6-difluorophenyl)benzimidazole, and wherein said X"" is selected from the group consisting of hydrogen, 4-methyl, 5-methyl, 6-methyl, 7-methyl, 4,5-dimethyl, 4,6-dimethyl, 4-ethyl, 4-cyano (CN), 4-methylenecyano ($CH_2CN$), 4-methoxy, 4-nitro, 5-nitro, 4-amino, 4-N-acetamido (NHAc), 4-N-methylamino (NHCH$_3$), 4-N-dimethylamino [N(CH$_3$)$_2$], 4-isopropyl, 4-isoprenyl, 4-bromo, 5-bromo, 6-bromo, 4-chloro, 5-chloro, 6-chloro, fluoro, N-methylacetamido (NAcCH$_3$), methyl carboxylate (CO$_2$Me), methyl acetamido ester (CH$_2$OAc), hydroxy, CNH(NH$_2$OH), amide (CONH$_2$), N-dimethylamide [CON(CH$_3$)$_2$], carboxylic acid, hydroxymethyl (CH$_2$OH), formyl, chloromethyl, 4-methyleneazido (CH$_2N_3$), aminomethyl (CH$_2NH_2$), N-acetamidomethyl (CH$_2$NHAc), CH$_2$NCH$_2$Ac, dimethyl ether (CH$_2$OCH$_3$), 4-methylenethiocyanate (CH$_2$NCS), and 4-methyleneacetylene (CH$_2$CCH). In a preferred embodiment, X"" is selected from the group consisting of hydrogen, 4-methyl, 4-ethyl, 4-cyano, 4-methoxy, 4-nitro, 4-amino, 4-N-acetamido, 4-N-methylamino, 4-N-dimethylamino, 4-isopropyl, 4-isopropenyl, 4-bromo, 4-chloro, 4-methyleneazido, 4-methylenecyano, 4-methylenethiocyanate, and 4-methyleneacetylene. The present invention also provides pharmaceutical compositions of substituted benzimidazoles having the general structure of FIG. 13A, wherein X"" is selected from the group consisting of hydrogen, 4-methyl, 4-ethyl, 4-cyano, 4-methoxy, 4-nitro, 4-amino, 4-N-acetamido, 4-N-methylamino, 4-N-dimethylamino, 4-isopropyl, 4-isopropenyl, 4-bromo, 4-chloro, 4-methyleneazido, 4-methylenecyano, 4-methylenethiocyanate, and 4-methyleneacetylene.

It is contemplated that the substituted benzimidazoles of the present invention comprise derivatives containing various groups. It is not intended that the present invention be limited to particular substituted benzimidazole derivatives. For example, it is intended that the present invention encompasses embodiments in which such groups as aromatic rings, hydrocarbons, and other structures are included. Such groups include, but are not limited to hydrogen, 4-methyl, 5-methyl, 6-methyl, 7-methyl, 4,5-dimethyl, 4,6-dimethyl, 4-chloro, 5-chloro, 6-chloro, 4-bromo, 5-bromo, 4-nitro, and 5-nitro, cyclopropyl, 2,6-difluorobenzyloxymethyl, 2,6-difluorophenyl, 2-fluoro-6-methoxyphenyl, pyridyl, naphthyl, 2,6-difluorobenzyl, benzyl, ethylbenzyl, 2,6-dichlorobenzyl, 2,3,4,5,6-pentafluorobenzyl, pyridylmethyl, benzenesulfonyl, 2,6-difluorobenzoyl, 3,3-dimethylallyl, fluoro, chloromethyl, methoxy, N-methylacetamide (NAcCH$_3$), ethyl, methyl carboxylate (CO$_2$Me), methyl acetamido ester (CH$_2$OAc), hydroxy, amine, N-acetamide (NHAc), N-methylamine (NHCH$_3$), N-diethylamine [N(CH$_3$)$_2$], cyano, CNH(NH$_2$OH), amide (CONH$_2$), N-dimethylamide [CON(CH$_3$)$_2$], carboxylic acid, isoprenyl, hydroxymethyl (CH$_2$OH), formyl, chloromethyl, aminomethyl (CH$_2$NH$_2$), N-acetamidomethyl (CH$_2$NHAc), CH$_2$NCH$_2$Ac, dimethyl ether (CH$_2$OCH$_3$), 4-methyleneazido (CH$_2$N$_3$), 4-methylenecyano, 4-methylenethiocyanate, and 4-methyleneacetylene. It is further intended that these groups be included in these compositions alone or in combination.

It is also contemplated that the aromatic residues of various embodiments of the present invention may be replaced with hydrophobic residues, such as aliphatic groups. For example, the present invention encompasses alkylimidazoles, including, but not limited to 1-(2,6-difluorobenzyl)-2-difluorophenyl-5,6-dialkylimidazole.

It is further contemplated that the present invention includes embodiments in which the carbons (C) present on the benzyl ring (i.e., C4, C5, C6, and C7) are replaced with nitrogen (N), singly, or in combination (e.g., azapurines).

It is contemplated that the substituted benzimidazoles of the present invention will find use in the treatment of HIV infection/disease. In particularly preferred embodiments, the present invention provides pharmaceutical compositions comprising substituted benzimidazoles with activity against HIV-1 RT.

The present invention also provides methods for treating human immunodeficiency virus (HIV) infection, comprising the steps of: a) providing: i) a subject suspected of being infected with human immunodeficiency virus; and ii) a composition having anti-reverse transcriptase activity and comprising at least one substituted benzimidazole having a 2,6-difluorobenzyl substituent at the N-1 site of the benzimidazole ring; b) exposing the subject to the composition having anti-reverse transcriptase activity; and c) observing for inhibition of anti-reverse transcriptase activity. In one preferred embodiment, the human immunodeficiency virus is HIV-1.

In one embodiment, the methods for treating HIV infection utilize substituted benzimidazoles further comprising a 2,6-difluorophenyl substituent at the C2 site of the benzimidazole ring. In particularly preferred embodiments, the methods for treating HIV infection utilize substituted benzimidazoles having the structure of FIG. 13A, wherein X"" is at least one substituent positioned at a benzimidazole carbon selected from C4, C5, C6, C7, C4 and C5, and C4 and C6 of a substituted 1-(2,6-difluorobenzyl)-2-(2,6-difluorophenyl)benzimidazole, and wherein said X"" is selected from the group consisting of hydrogen, 4-methyl, 5-methyl, 6-methyl, 7-methyl, 4,5-dimethyl, 4,6-dimethyl, 4-ethyl, 4-cyano (CN), 4-methylenecyano (CH$_2$CN), 4-methoxy, 4-nitro, 5-nitro, 4-amino, 4-N-acetamido (NHAc), 4-N-methylamino (NHCH$_3$), 4-N-dimethylamino [N(CH$_3$)$_2$], 4-isopropyl, 4-isoprenyl, 4-bromo, 5-bromo, 6-bromo, 4-chloro, 5-chloro, 6-chloro, fluoro, N-methylacetamido (NAcCH$_3$), methyl carboxylate (CO$_2$Me), methyl acetamido ester (CH$_2$OAc), hydroxy, CNH(NH$_2$OH), amide (CONH$_2$), N-dimethylamide [CON(CH$_3$)$_2$], carboxylic acid, hydroxymethyl (CH$_2$OH), formyl, chloromethyl, 4-methyleneazido (CH$_2$N$_3$), aminomethyl (CH$_2$NH$_2$), N-acetamidomethyl (CH$_2$NHAc), CH$_2$NCH$_2$Ac, dimethyl ether (CH$_2$OCH$_3$), 4-methylenethiocyanate (CH$_2$NCS), and 4-methyleneacetylene (CH$_2$CCH). In preferred embodiments, X"" is selected from the group consisting of hydrogen, 4-methyl, 4-ethyl, 4-cyano, 4-methoxy, 4-nitro, 4-amino, 4-N-acetamido, 4-N-methylamino, 4-N-dimethylamino, 4-isopropyl, 4-isopropenyl, 4-bromo, 4-chloro, 4-methyleneazido, 4-methylenecyano, 4-methylenethiocyanate, and 4-methyleneacetylene.

In another embodiment, the methods for treating human immunodeficiency virus infection utilize substituted benzimidazoles having the structure of FIG. 7A, wherein X" is selected from the group consisting of hydrogen, methyl, ethyl, cyano, methoxyl, nitro, amine, acetamide, methylamine, dimethylamine, isopropyl, isopropenyl, bromine and chlorine; and R" is selected from the group consisting of 2,6-difluorobenzyl, benzyl, ethylbenzyl, 2,6-dichlorobenzyl, 2,3,4,5,6-pentafluorobenzyl, pyridylmethyl, benzenesulfonyl, 2,6-difluorobenzoyl, and 3,3-dimethylallyl. In a preferred embodiment, R" is 2,6-difluorobenzyl. In yet another embodiment, the methods for treating human immunodeficiency virus infection utilize substituted benzimidazoles having the structure of FIG. 7B, wherein X' is selected from the group consisting of hydrogen and methyl, ethyl, cyano, methoxyl, nitro, amine, acetamide, methylamine, dimethylamine, isopropyl, isopropenyl, bromine and chlorine; and R' is selected from the group consisting of phenyl, formyl, isopropyl, H, methyl, cyclopropyl, hydroxymethyl, 2,6-difluorobenzyloxymethyl, 2,6 difluorophenyl (2,6-F$_2$Ph), methylphenyl (2-CH$_3$Ph), 2-fluoro-6-methoxylphenyl, pyridyl (e.g., 4-Py, 3-Py), and naphthyl (e.g., 1-Nap, 2-Nap). In a preferred embodiment, R' is 2,6-difluorophenyl.

Furthermore, the present invention provides methods for inhibiting HIV-1 reverse transcriptase, comprising the steps of: a) providing: i) a sample suspected of being infected with HIV-1 virus; and ii) a composition having anti-reverse transcriptase activity and comprising at least one substituted benzimidazole having a 2,6-difluorobenzyl substituent at the N-1 site of said benzimidazole; b) exposing the sample to the composition having anti-reverse transcriptase activity; and c) observing for inhibition of said anti-reverse transcriptase activity.

In some embodiments, the methods for inhibiting HIV-1 reverse transcriptase utilize substituted benzimidazoles further comprising a 2,6-difluorophenyl substituent at the C2 site of the benzimidazole ring. In particularly preferred embodiments, the methods for inhibiting HIV-1 reverse transcriptase utilize substituted benzimidazoles having the structure of FIG. 13A, wherein X"" is at least one substituent positioned at a benzimidazole carbon selected from C4, C5, C6, C7, C4 and C5, and C4 and C6 of a substituted 1-(2,6-difluorobenzyl)-2-(2,6-difluorophenyl) benzimidazole, and wherein said X"" is selected from the group consisting of hydrogen, 4-methyl, 5-methyl, 6-methyl, 7-methyl, 4,5-dimethyl, 4,6-dimethyl, 4-ethyl, 4-cyano (CN), 4-methylenecyano (CH$_2$CN), 4-methoxy, 4-nitro, 5-nitro, 4-amino, 4-N-acetamido (NHAc), 4-N-methylamino (NHCH$_3$), 4-N-dimethylamino [N(CH$_3$)$_2$], 4-isopropyl, 4-isoprenyl, 4-bromo, 5-bromo, 6-bromo, 4-chloro, 5-chloro, 6-chloro, fluoro, N-methylacetamido (NAcCH$_3$), methyl carboxylate (CO$_2$Me), methyl acetamido ester (CH$_2$OAc), hydroxy, CNH(NH$_2$OH), amide (CONH$_2$), N-dimethylamide [CON(CH$_3$)$_2$], carboxylic acid, hydroxymethyl (CH$_2$OH), formyl, chloromethyl, 4-methyleneazido (CH$_2$N$_3$), aminomethyl (CH$_2$NH$_2$), N-acetamidomethyl (CH$_2$NHAc), CH$_2$NCH$_2$Ac, dimethyl ether (CH$_2$OCH$_3$), 4-methylenethiocyanate (CH$_2$NCS), and 4-methyleneacetylene (CH$_2$CCH). In preferred embodiments, X"" is selected from the group consisting of hydrogen, 4-methyl, 4-ethyl, 4-cyano, 4-methoxy, 4-nitro, 4-amino, 4-N-acetamido, 4-N-methylamino, 4-N-dimethylamino, 4-isopropyl, 4-isopropenyl, 4-bromo, 4-chloro, 4-methyleneazido, 4-methylenecyano, 4-methylenethiocyanate, and 4-methyleneacetylene.

In another embodiment, the methods for inhibiting HIV-1 reverse transcriptase utilize substituted benzimidazoles having the structure of FIG. 7A, wherein X" is selected from the group consisting of hydrogen, methyl, ethyl, cyano, methoxyl, nitro, amine, acetamide, methylamine, dimethylamine, isopropyl, isopropenyl, bromine and chlorine; and R" is selected from the group consisting of 2,6-difluorobenzyl, benzyl, ethylbenzyl, 2,6-dichlorobenzyl, 2,3,4,5,6-pentafluorobenzyl, pyridylmethyl, benzenesulfonyl, 2,6-difluorobenzoyl, and 3,3-dimethylallyl. In a preferred embodiment, R" is 2,6-difluorobenzyl. In yet another embodiment, the methods for inhibiting HIV-1 reverse transcriptase utilize substituted benzimidazoles having the structure of FIG. 7B, wherein X' is selected from the group consisting of hydrogen and methyl, H, methyl, ethyl, cyano, methoxyl, nitro, amine, acetamide, methylamine, dimethylamine, isopropyl, isopropenyl, bromine and chlorine; and R' is selected from the group consisting of phenyl, formyl, isopropyl, H, methyl, cyclopropyl, hydroxymethyl, 2,6-difluorobenzyloxymethyl, 2,6 difluorophenyl (2,6-F$_2$Ph), methylphenyl (2-CH$_3$Ph), 2-fluoro-6-methoxylphenyl, pyridyl (e.g., 4-Py, 3-Py), and naphthyl (e.g., 1-Nap, 2-Nap). In a preferred embodiment, R' is 2,6-difluorophenyl.

In addition, it is contemplated that the present invention encompasses analogs of the benzimidazole ring system which are capable of undergoing dissociation in the binding pocket of HIV RT, to give rise to electrophilic intermediates that react with nucleophilic sites in the pocket. Thus, it is contemplated that compounds that act as irreversible inhibitors of HIV RT also be encompassed as embodiments within the present invention.

It is not intended that the compounds of the present invention be limited to any particular use. Indeed, it is intended that the compounds of the present invention will be utilized against organisms other than HIV.

Definitions

To facilitate understanding of the invention, a number of terms are defined below.

As used herein, the term "retrovirus" refers to a group of viruses with RNA genomes. Retroviruses are characterized as having reverse transcriptase, the enzyme that allows the RNA genome to be transcribed into DNA.

As used herein, the term "reverse transcriptase" refers to an enzyme with RNA-dependent DNA polymerase activity, with or without the usually associated DNA-dependent DNA polymerase and ribonuclease activity observed with wild-type reverse transcriptases.

As used herein, the term "anti-viral" is used in reference to any compound, substance, or molecule capable of inhibiting or preventing viral replication and/or dissemination. It is intended that the term encompasses compounds capable of inhibiting viral replication by interfering with such activities as the reverse transcriptase activity of retroviruses. It is also intended to encompass "non-nucleoside reverse transcriptase inhibitors" (NNRTI). In preferred embodiments, the term is used in reference to substituted benzimidazole compounds.

As used herein, the term "chemotherapeutic" refers to any compound, element, or substance useful against disease. In preferred embodiments, the term encompasses compounds such as the substituted benzimidazoles of the present invention.

As used herein, the term "purified" refers to the removal of contaminants from a sample. Methods such as carbon, hydrogen and nitrogen analyses (CHN analysis, or "elemental analysis") may be used to determine the purity of compounds. In preferred embodiments, the CHN values of compounds of the present invention are very close to the predicted values. Correspondence of experimental with the predicted values to within 0.3% indicates high levels of purity. In particularly preferred embodiments, the compounds of the present invention have CHN values within 0.3% of the predicted values. In less preferred embodiments, the level of purity may be lower (i.e., greater than 0.3% difference between the predicted and actual CHN values).

As used herein, the terms "benzimidazole" and "substituted benzimidazole" are used in reference to molecules with the core structure as indicated in FIG. 1. It is intended that the term encompasses compounds in which substitutions, including additions, have been made to the chemical structure. The term encompasses, but is not limited to substitution reactions, wherein there is replacement of one or more atoms or group in a molecule by another atom or group. In a preferred embodiment, the present invention encompasses 1- and 2-substituted benzimidazoles (See e.g., FIG. 7), including but not limited to 1-(2,6-difluorobenzyl)-2-(2,6-difluorophenyl)-4-methylbenzimidazole (See e.g., FIG. 13).

As used herein, the term "substituent" is used in reference to functional and molecular groups present in the substituted benzimidazole. The terms "C2," "C4," "C5," "C6," "C7", etc. refer to a carbon in the benzimidazole ring and its position in the benzimidazole ring, following the numbering convention for the benzimidazole ring as indicated in FIG. 1. For example, the term "C4 and C5" refers to the carbons at the 4 and 5 positions of the benzimidazole ring, while the term "C4 and C6" refers to carbons at the 4 and 6 positions of the benzimidazole ring.

As used herein, the term "TBZ" refers to 1-(2,6-difluorophenyl)-1H,3-thiazolo[3,4-a]benzimidazole.

The term "cyclic compounds" refers to compounds having one (i.e., a monocyclic compounds) or more than one (i.e., polycyclic compounds) ring of atoms. The term is not limited to compounds with rings containing a particular number of atoms. While most cyclic compounds contain rings with five or six atoms, rings with other numbers of atoms (e.g., three or four atoms) are also contemplated by the present invention. The identity of the atoms in the rings is not limited, though the atoms are usually predominantly carbon atoms. Generally speaking, the rings of polycyclic compounds are adjacent to one another; however, the term "polycyclic" compound includes those compounds containing multiple rings that are not adjacent to each other.

The term "heterocyclic compounds" refers broadly to cyclic compounds wherein one or more of the rings contains more than one type of atom. In general, carbon represents the predominant atom, while the other atoms include, for example, nitrogen, sulfur, and oxygen. Examples of heterocyclic compounds include benzimidazole, furan, pyrrole, thiophene, and pyridine.

The terms "aromatic," "aromatic compounds," and the like refer broadly to compounds with rings of atoms having delocalized electrons. The monocyclic compound benzene ($C_6H_6$) is a common aromatic compound. However, electron delocalization can occur over more than one adjacent ring (e.g., naphthalene [two rings] and anthracene [three rings]). Different classes of aromatic compounds include, but are not limited to, aromatic halides (aryl halides), aromatic heterocyclic compounds, aromatic hydrocarbons (arenes), and aromatic nitro compounds (aryl nitro compounds).

As used herein, the terms "aliphatic" and "aliphatic compounds" refer to compounds which comprise carbon atoms in chains, rather than the ring structure of aromatic compounds. It is intended that these aliphatic moieties will be bound to -additional elements in some embodiments.

The terms "resistant" and "refractory" used in reference to "resistant mutants" of HIV and/or HIV RT, refer to the ability of some HIV RTs to function in the presence of compounds that are inhibitory to the RT of wild-type HIV. This resistance may result from any number of mutations, including but not limited to conformational changes in the RT structure, as well as to the configuration of the RT bound to its substrate.

The term "mixture" refers to a mingling together of two or more substances without the occurrence of a reaction by which they would lose their individual properties. The term "solution" refers to a liquid mixture. The term "aqueous solution" refers to a solution that contains some water. In many instances, water serves as the diluent for solid substances to create a solution containing those substances. In other instances, solid substances are merely carried in the aqueous solution (i.e., they are not dissolved therein). The term aqueous solution also refers to the combination of one or more other liquid substances with water to form a multi-component solution.

The terms "sample" and "specimen" in the present specification and claims are used in their broadest sense. On the one hand, they are meant to include a specimen or culture. On the other hand, they are meant to include both biological and environmental samples. These terms encompass all types of samples obtained from humans and other animals, including but not limited to, body fluids such as urine, blood, fecal matter, cerebrospinal fluid (CSF), semen, and saliva, as well as solid tissue. These terms also refer to swabs and other sampling devices commonly used to obtain samples for culture of microorganisms.

Biological samples may be animal, including human, fluid or tissue, food products and ingredients such as dairy items, vegetables, meat and meat by-products, and waste. Environmental samples include environmental material such as surface matter, soil, water, and industrial samples, as well as samples obtained from food and dairy processing instruments, apparatus, equipment, disposable, and non-disposable items. These examples are not to be construed as limiting the sample types applicable to the present invention.

As used herein, the term "culture" refers to any sample or specimen which is suspected of containing one or more microorganisms. "Pure cultures" are cultures in which the organisms present are only of one strain of a particular genus and species. This is in contrast to "mixed cultures," which are cultures in which more than one genus, species, and/or strain of microorganism are present.

As used herein, the term "organism" is used to refer to any species or type of microorganism, including but not limited to viruses. In particular, the term is used in reference to RNA viruses, such as the retroviruses. In preferred embodiments, the organism of interest is HIV. In particularly preferred embodiments, the organism of interest is HIV-1.

The term "parenterally" refers to administration to a subject through some means other than through the gastrointestinal tract or the lungs. The most common mode of parenteral administration is intravenous. However, other modes of parenteral administration include, but are not limited to, intramuscular, intradermal, intrathecal, intranasal and subcutaneous administration.

As used herein, the term "pharmaceutical composition" refers to compositions composed of one or more pharmaceutically acceptable diluents, excipients or carriers. As used herein, the phrase "pharmaceutical preparation suitable for parenteral administration" refers to a solution containing compound in a pharmaceutically acceptable form for parenteral administration. The characteristics of the form will depend on a number of factors, including the mode of administration. For example, a preparation for intravenous administration will often comprise compound dissolved in normal saline or sterile water for injection. Of course, the pharmaceutical preparations of the present invention are not limited to those diluents; indeed, other components or diluents known in the field of pharmaceuticals and pharmacy are within the scope of the present invention. The pharmaceutical preparation may contain diluents, adjuvants and excipients, among other components, provided that those additional components neither adversely effect the preparation (e.g., they do not cause degradation of the compound) nor the recipient (e.g., they do not cause a hypersensitivity reaction).

DESCRIPTION OF THE INVENTION

The present invention provides substituted benzimidazole compounds, which act as non-nucleoside inhibitors of reverse transcriptase (RT). In particular, the present invention relates to a novel class of substituted benzimidazoles, effective in the inhibition of human immunodeficiency virus (HIV) RT.

The Description of the Invention is subdivided into I) Imidazoles and Benzimidazoles; II) Synthesis of Substituted Benzimidazoles; III) Biological Activity of Substituted Substituted Benzimidazoles; IV) Geometry of TBX and 1-(2,6-Difluorobenyl)-2-Phenylbenzimidazole; and V) Purity of the Substituted Benzimidazoles.

I. Imidazoles and Benzimidazoles

In addition to compounds such as tetrahydroimidazo(4,5,1-1-jk)(1,4)-benzodiazepin-2-(1H)-one, and -thione (TIBO) derivatives, dipyridodiazepinones, pyridinones, bis(heteroaryl)piperazines (BHAPs), 2',5'-bis-O-(tertbutyldimethylsilyl)-3'-spiro-5"-(4"-amino-1",2"-oxathiole-2",2"-dioxide)pyrirmidine (TSAO) derivatives, α-anilinophenylacetamide (α-APA), 8-chloro-4,5,6,7-tetrahydro-5-methylimidazo-[4,5,1-jk][1,4] benzodiazepine-2 (1H)-one (8-Cl TIBO), and nevirapine, the potential therapeutic utility of imidazole compounds such as 1-(2,6-difluorophenyl)-1H,3H-thiazolo[3,4-a] benzimidazole (TBZ) has been shown. (See, e.g., A. Chimirri et al., "Anti-HIV Agents: Synthesis and In Vitro Anti-HIV Evaluation of Novel 1H,3H-Thiazolo[3,4-a] Benzimidazoles," *Il Farmaco* 46:817–823 [1991]).

Figure 1:
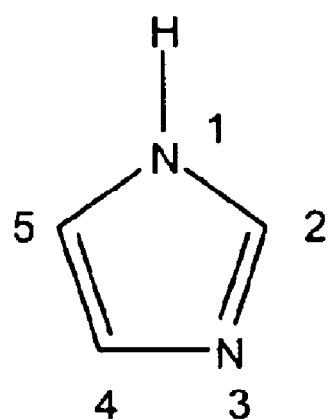
FIG. 1 shows the general structures of imidazole and benzimidazole.
Figure 1:
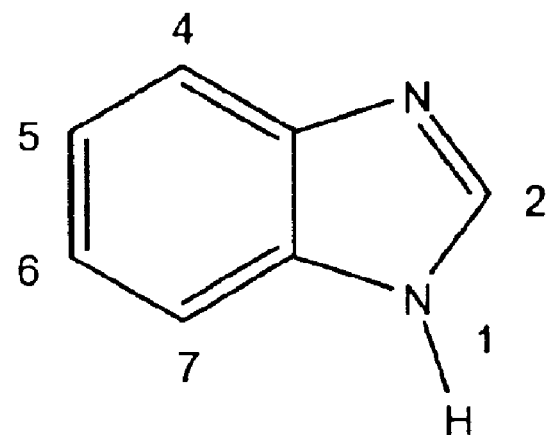

As shown in FIG. 1, imidazoles (i.e., glyoxaline, 1,2-diazole, iminazole, miazole, pyrro[b]monazole, and 1,3-diaza-2,4-cyclopentadiene), are five-membered heterocycles with the formula $C_3H_4N_2$. The properties of these compounds permit the existence of cyclic aromatic structures (i.e., derivatives) with more than two nitrogens or other heteroatoms bonded together. Many derivatives of these heterocyclic structures are important biochemical intermediates. FIG. 1 also shows the structure of benzimidazole (i.e., benziminazole, 1,3-benzodiazole, azindole, benzoglyoxaline, N,N'-methenyl-o-phenylenediamine, with the formula $C_7H_6N_2$). The numbering conventions for the ring positions are indicated in these structures.

Imidazoles (e.g., clotrimazole, miconazole, econazole, and isoconazole) have found clinical use as anti-fungals, as they inhibit fungal cell ergosterol synthesis, but do not readily interfere with cholesterol synthesis in host (e.g., mammalian) cells. However, these drugs have undesirable side effects when administered systemically, such as pruritis, anemia, hyponatremia, leukopenia, thrombocytopenia, and elevated liver enzymes. Thus, their use has mainly been limited to topical treatment of fungal infections. Ketoconazole (another imidazole) is water-soluble and is easily absorbed from the gastrointestinal tract for oral treatment of systemic fungal infections. Although good results are usually obtained with otherwise healthy patients, severe problems in immunocompromised patients have been reported.

Benzimidazoles (e.g., thiabendazole, mebendazole, and albendazole) have found clinical use as anti-helmintics, as they are effective against both the larval and adult stages of nematodes that cause ascariasis, intestinal capillariasis, enterobiasis, trichuriasis, as well as single and mixed hookworm infection. However, as with the imidazoles, the toxicity of these compounds, and/or their limited bioavailability have limited their clinical utility.

Benzimidazole derivatives have been investigated as antiviral agents, and some have been recognized as being capable of inhibiting RNA viruses. (See, e.g., Gilbert et al., *Antiviral Res.*, 9:355 [1988]). In addition, it has been recognized that thiazolobenzimidazole analogs may enhance the immune response. (See, e.g., Warren et al., *Immunopharmacol.*, 1:269 ([1979]; Fenichel et a., *Immunopharmacol.*, 2:491 [1981]; and U.S. Pat. No. 4,214,089 to Fenichel et al., herein incorporated by reference). Other derivatives of thiazolobenzimidazole, such as 1-phenyl substituted 1H,3H-thiazole[3,4-a] benzimidazoles have also been reported as having anti-HIV-1 RT activity. (See, e.g., EP 0471991, to Monforte et al.).

As mentioned above, one thiazolobenzimidazole compound, TBZ, has been shown to have HIV-1 RT inhibitory activity. However, there are some drawbacks to the use of TBZ. (See, e.g., Chimirri et al., Anti-HIV Agents. I. Synthesis and In Vitro Anti-HIV Evaluation of Novel 1H,3H-Thiazolo[3,4-a]Benzimidazoles," supra; Chimirri et al., "Anti-HIV Agents. II. Synthesis and In Vitro Anti-HIV Evaluation of Novel 1H,3H-Thiazolo[3,4-1] Benzimidazoles," *Il Farmaco* 46:925–933 [1991]; and Buckheit et al., "Thiazolobenzimidazole: Biological and Biochemical Anti-Retroviral Activity of a New Non-Nucleoside Reverse Transcriptase Inhibitor," *Antiviral Res.*, 21:247–265 [1993]). One problem with TBZ is its susceptibility to metabolic oxidation of the thiazolo ring, resulting in the formation of less potent sulfoxide and sulfone metabolites (El Dareer et al., "Metabolism and Disposition of a Thiazolobenzimidazole Active Against Human Immunodeficiency Virus-1," *Drug Metabol. Dispos.*, 21:231–235 [1993]).

Another problem is the loss of antiviral activity against HIV strains with mutated RT. (See, Boyer et al., Analysis of Nonnucleoside Drug-Resistant Variants of Human Immunodeficiency Virus Type 1 Reverse Transcriptase," *J. Virol.*, 67:2412–2420; and Buckheit et al., "Comparative Anti-HIV Evaluation of Diverse HIV-1 Specific Reverse Transcriptase Inhibitor-Resistant Virus Isolates Demonstrates the Existence of Distinct Phenotypic Subgroups," *Antiviral Res.*, 26:117–132 [1995]). During the development of the present invention, the drawbacks of TBZ were addressed in order to provide NNRTIs capable of efficiently and effectively inhibiting wild type, as well as mutated HIV-1 RT, with low toxicity levels, and a favorable therapeutic dose.

Figure 2:
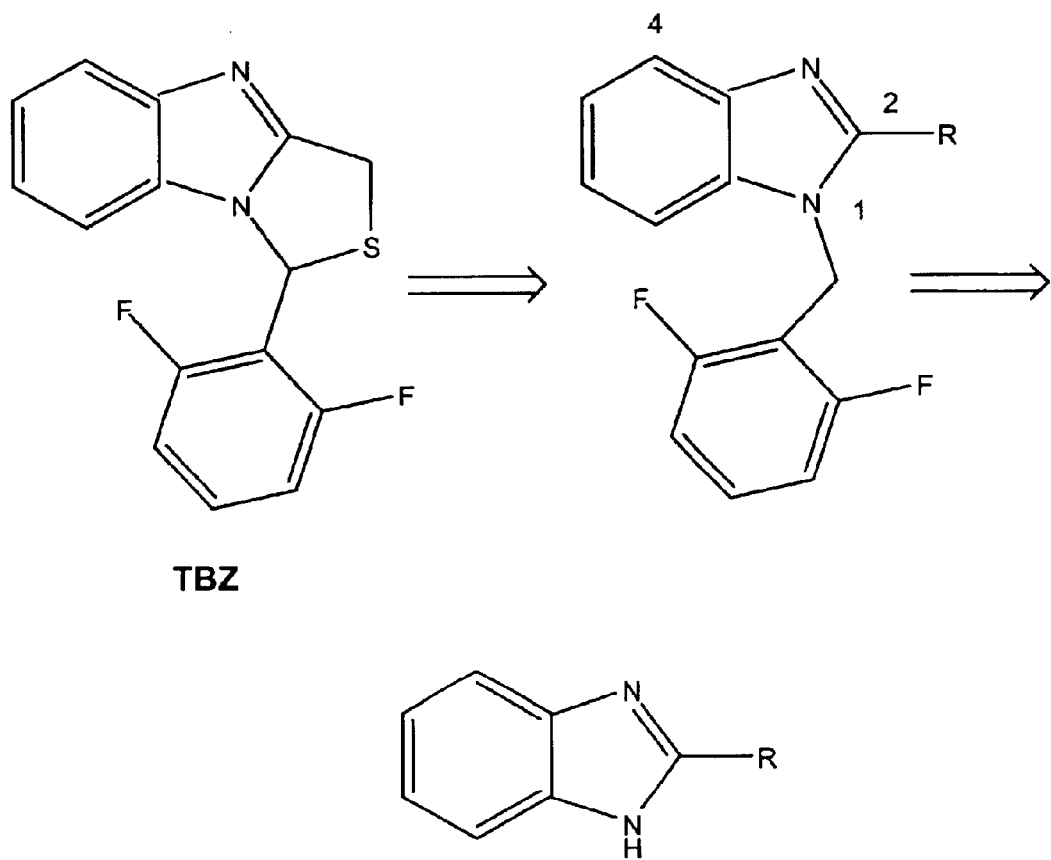
FIG. 2 is a schematic retrosynthetic analysis of N-benzyl-2-alkylbenzimidazoles by alkylation of 2-substituted benzimidazoles.

During early stages in the development of the present invention, retrosynthetic analysis was applied to TBZ. This indicated that opening the thiazolo ring of TBZ could result in the production of compounds potentially useful for inhibition of HIV RT, and resulted in the development of the novel benzimidazoles disclosed herein. FIG. 2 shows a schematic for one embodiment of the present invention, in which N-benzyl-2-alkylbenzimidazoles are synthesized by alkylation of 2-substituted benzimidazoles, as was attempted during the development of the present invention. These substituted N-benzyl-benzimidazoles were of interest as potentially providing enhanced inhibition of wild type RT, and the various clinically observed variant forms of HIV RT. This was one highly important aspect of the present invention, as most of the known NNRTIs are rendered ineffective by the emergence of mutant forms of HIV. (See, De Clercq, "HIV Resistance to Reverse Transcriptase Inhibitors," *Biochem. Pharm.*, 47:155–169 [1994]). Especially in view of the development of resistance to compounds previously effective against HIV, it was of great interest to develop compounds effective against mutants of HIV RT. For example, development of a compound that was effective against Y181 C, a mutant that has a high degree of resistance to most NNRTIs (e.g., α-APA, nevirapine, and TIBO derivatives) was a major consideration in the development of the present invention. (See, e.g. "Structure of HIV-1 RT/TIBO R86183 Complex Reveals Similarity in the Binding of Diverse Nonnucleoside Inhibitors," *Struct. Biol.*, 2:407–415 [1995]). Thus, during the development of the present invention, various compounds were developed and tested for their ability to inhibit both WT and mutated forms of HIV-1 RT. Various approaches were taken in order to produce these compounds, including synthesizing benzimidazoles with substitutions at one or more positions.

II. Synthesis of Substituted Benzimidazoles

A. Synthesis of 1- and 2-Substituted Benzimidazoles

Figure 3:
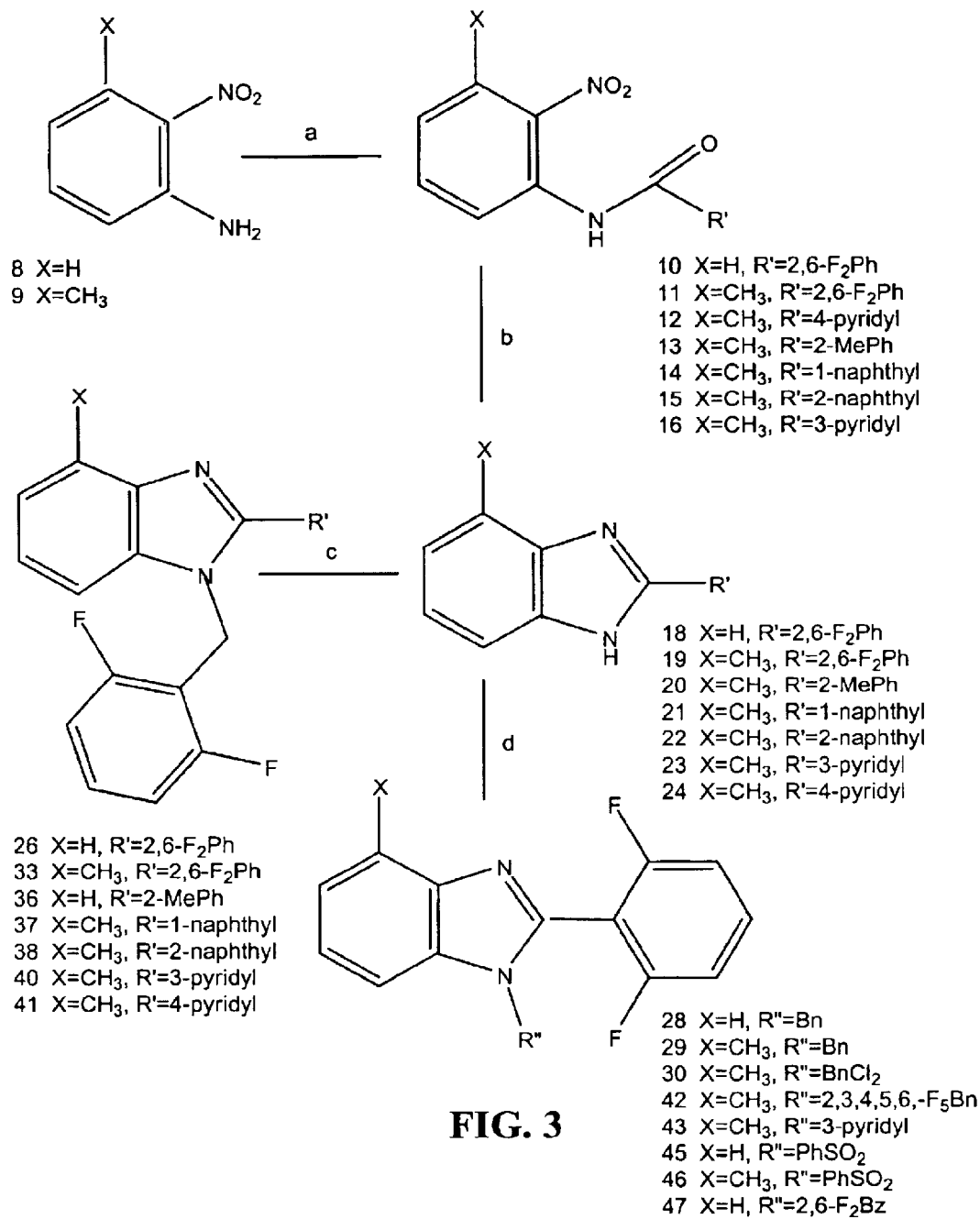
FIG. 3 is a schematic synthesis of substituted 2-(2,6-difluorophenyl)benzimidazoles.

A variety of 1- and 2-substituted benzimidazoles were prepared. FIG. 3 provides a schematic approach for the synthesis of these compounds from nitroanilines and an appropriate choice of acylating reagent. In this Figure, "a" comprises aroyl chloride, pyridine/THF; "b" comprises Fe/AcOH; "c" comprises 2,6-F$_2$-BnBr, NaH, THF; and "d" comprises BnBr or PhSO$_2$Cl or 2,6-F$_2$BzCl (7), THF. In most cases, it was found that high yields of the desired N-acyl-nitroaniline could be obtained from either 2-nitroaniline (3), or 2-methyl-6-nitroaniline (9). Only in the case of 1-naphthyl derivative (14) was a mixture of mono and bis acylated product formed. Subsequent reductive cyclization of compounds 10–16 with iron yielded the desired 2-aryl-benzimidazoles 18–24. Following their coupling with 2,6-difluorophenyl-α-bromotoluene, the desired 2-aryl-1 (2,6-difluorobenzyl)-benzimidazoles were obtained.

The first 2-substituted derivatives of N-2(2,6-difluorobenzyl)benzimidazole studied during the development of the present invention were the methyl, hydroxymethyl, isopropyl, carboxyl, formyl, and phenyl derivatives. With methyl and phenyl compounds, commercially available benzimidazoles were reacted with 2,6-difluorophenyl-α-bromotoluene to give 1-(2,6-difluorobenzyl)-2-methylbenzimidazole (35) and 1-(2,6-difluorobenzyl)-2-phenylbenzimidazole (39). Preparation of the hydroxymethyl substitute was achieved by acid-catalyzed condensation-cyclization of glycolic acid with either o-phenylenediamine or 2,3-diaminotoluene, using an approach similar to that described by Chimirri et al. for the synthesis of TBZ. (See, FIG. 4. See also, Chimirri et al., Anti-HIV Agents. I. Synthesis and In Vitro Anti-HFV Evaluation of Novel 1H,3H-Thiazolo[3,4-a]Benzimidazoles, "supra; and Chimirri et al., "Anti-HIV Agents. II. Synthesis and In Vitro Anti-HIV Evaluation of Novel 1H,3H-Thiazolo [3,4-1]Benzimidazoles," supra).

Figure 4:
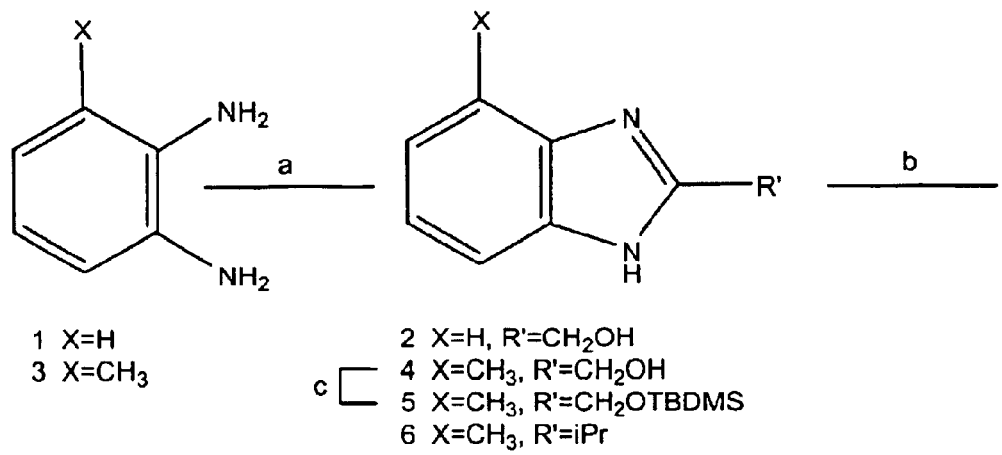
FIG. 4 is a schematic synthesis of substituted 1-(2,6-difluorophenyl)benzimidazoles.
Figure 4:
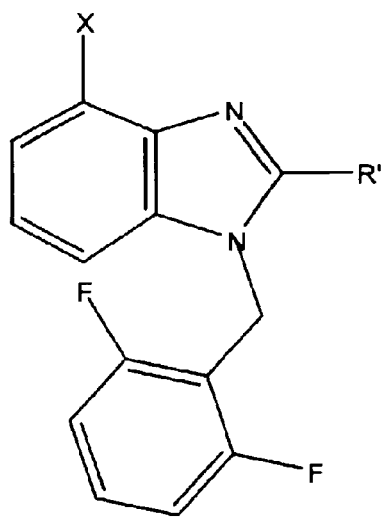
Figure 4:
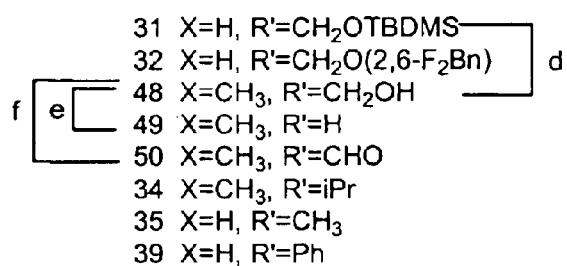

FIG. 4 provides a schematic of substituted N-2(2,6-difluorobenzyl)-benzimidazoles. In this Figure, "a" comprises glycolic or isobutyric acid, 4 N HCl, reflux; "b" comprises 2,6-F$_2$-BzCl (7) or 2,6-F$_2$Bnr (25); "c" comprises t-butyldimethylsilylchloride (tBDMSCl), pyridine; "d" comprises Bu$_4$NF, THF; "e" comprises KMnO$_4$; and "f" comprises CrO$_3$. As shown in FIG. 4, the hydroxymethyl intermediate was protected with t-butyldimethylsilyl (TBDMS), and subsequently N-alkylated with 2,6-difluorophenyl-α-bromotoluene (25). Removal of TBDMS from (31) resulted in the production of 1-(2,6-difluorobenzyl)-2-hydroxymethyl-4-methylbenzimidazole (49). However, oxidation of the hydroxymethyl to the carboxylic acid was found to be problematic. When a strong oxidant (e.g., KMnO$_4$) was used, the isolated product (50) indicated that decarboxylation occurred under acidic reaction conditions. Oxidation under basic conditions with chromium oxide similarly yielded (50), along with the formyl product. The carboxylic acid form was not isolated. A final product prepared from the 2-hydroxymethylbenzimidazole (4) was the bis-2,6-difluorobenzyl derivative (32).

B. Synthesis and Biological Activity of Substituted 1-(2, 6-difluorobenzyl)-2-(2,6-difluorophenyl)Benzimidazoles In addition to the 1- and 2-substituted benzimidazoles described above, 4-, 5-, 6-, and 7-mono- and di-substitutions of 1-(2,6-difluorobenzyl)-2-(2,6-difluorophenyl) benzimidazole, and its des-methyl analog, 1-(2,6-difluorobenzyl)-2-(2,6-difluorobenzyl)benzimidazole (26) were synthesized and their properties observed. On the basis of inhibition of HIV-1 cytopathic effect (i.e., protection from cell killing in the assay described in Example 91), it was determined that C-4 substituted analogs were consistently the most active compounds, as long as the substitution did not introduce strong electron withdrawing groups. Although it was less active, the 6-substituted analogs of 1-(2,6-difluorobenzyl)-2-(2,6-difluorobenzyl)-4-methylbenzimidazole (33) also exhibited desired activity. However, the 5- or 7-substituted analogues of 33 showed decreased RT inhibition (See, FIG. 6).

Figure 8:
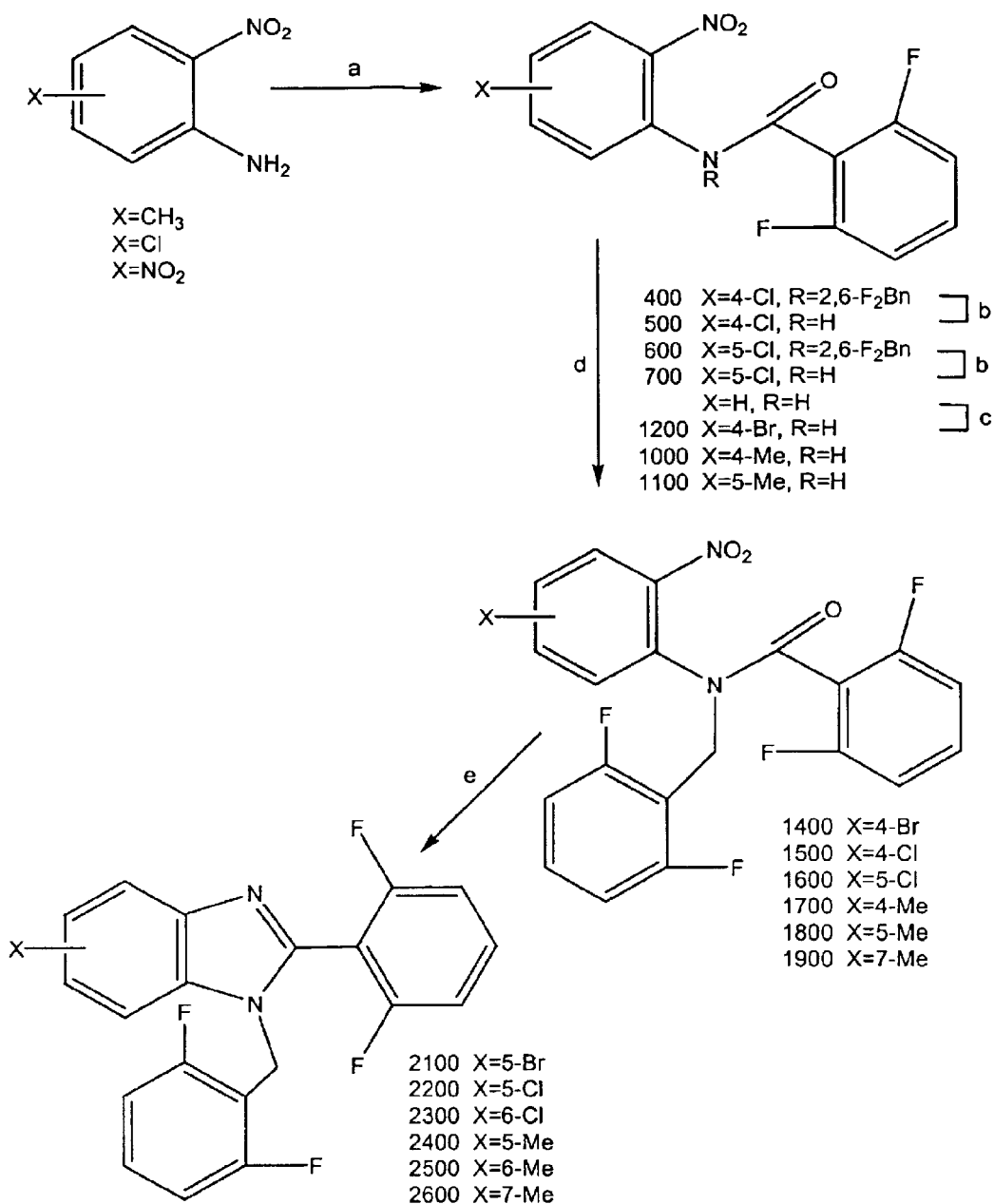
FIG. 8 is a schematic synthesis of substituted 1-(2,6-difluorobenzyl)-2-(2,6-difluorophenyl)benzimidazoles.

A variety of 1-(2,6-difluorobenzyl)-2-(2,6-difluorophenyl)benzimidazole compounds were prepared. The general approach utilized in the synthesis of the desired substituted 1-(2,6-difluorobenzyl)-2-(2,6-difluorophenyl) benzimidazoles is outlined in FIG. 8. In this Figure, "a" comprises 2,6-difluorobenzoyl chloride, pyridine:THF (1:1); "b" comprises NaOH, MeOH, dioxane; "c" comprises Br$_2$, pyridine, THF; "d" comprises 2,6-F$_2$BnBr, NaH, THF; and "e" comprises Fe, AcOH. Since a variety of substituted 6-nitroanilides are commercially available, this starting material was an ideal reagent to prepare a variety of differentially substituted benzimidazole derivatives. Depending on the type and regiochemistry of the different substitutents, the desired mono-acylated product could be obtained in good yields using 1.2 equivalents of 2,6-difluorobenzoyl chloride. In the case electron withdrawing substituents, benzoylation led to a mixture of mono and bis-acylated products. Variations in time, temperature, equivalents of reactants, and concentration were examined in unsuccessful efforts to produce only the desired mono-2,6-difluorobenzoyl products. The mono-2,6-difluorobenzoyl compounds were obtained in high yields by synthesizing the bis-2,6-difluorobenzoyl derivatives with excess 2,6-difluorobenzoyl chloride followed by selective base-catalyzed deacylation to the mono-benzoyl product.

Depending on the desired regiochemistry of the final benzimidazoles, the mono-acylated 6-nitro-anilides were either reductively cyclized with iron (i.e., "Method B." See e.g., Example 12) and alkylated with 2,6-difluorobenzyl bromide (i.e., Method A. See e.g., Example 5) or alkylated with 2,6-difluorobenzyl bromide and then reductively cyclized. For instance, 2-Substituted 6-nitroanilides were reductively cyclized to 4-substituted benzimidazoles. Alkylation of the benzimidazole N1 position with 2,6-difluorobenzyl bromide proceeded with >92% regiochemical purity for a variety of 4-substituted compounds. In the case of 5-, 6- and 7-substituted benzimidazoles, regiochemical control was maintained by alkylation of the mono-acylated derivate (Method A) to N-(2,6-difluorobenzyl)-N-(2,6-difluorophenyl)-nitroanilides followed by reductive cyclization (Method B).

Non-reductive acid catalyzed cyclization, in contrast, was used to synthesize 1-(2,6-difluorobenzyl)-2-(2,6- difluorophenyl)-4-nitrobenzimidazole, a key intermediate for many C4 derivatives. Mono-acylation of 3-nitro-1,2-phenylenediamine with 2,6-difluorobenzoyl chloride yielded a single product that was subsequently cyclized with only acid and heat. Since cyclization of either N-1 or N-2 acylated product would lead to the desired 2-aryl-benzimidazole, detailed regiochemical analysis was not carried out on N-(2,6-difluorobenzoyl)-2-amino-3-nitroanilide.

A side reaction found during the preparation of 1-(2,6-difluorobenzyl)-2-(2,6-difluorophenyl)-4-nitrobenzimidazole (Example 83) and in other electron withdrawing benzimidazoles, was sodium methoxide displacement resulting from methanol used to quench the excess NaH following alkylation of 1-(2,6-difluorobenzyl)-2-(2,6-difluorophenyl)-4-nitrobenzimidazole with 2,6-difluorobenzyl bromide. In order to prevent aromatic nucleophilic displacement, quenching of excess NaH was done subsequently with t-butanol.

Figure 9:
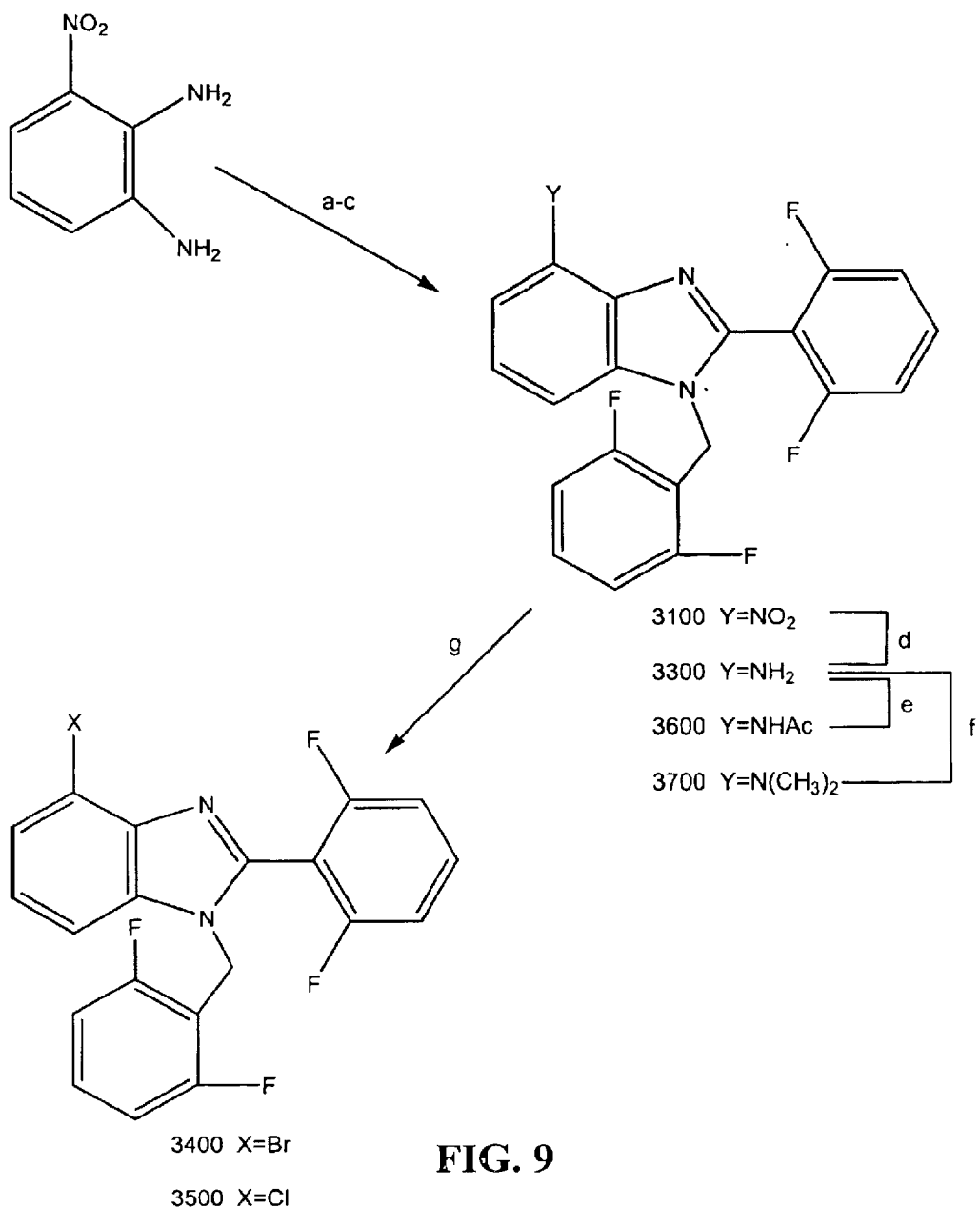
FIG. 9 is a schematic synthesis of the reduction of the 4-nitro group of 3100 with tin chloride.

The 4-nitro group in 1-(2,6-difluorobenzyl)-2-(2,6-difluorophenyl)-4-nitro-benzimidazole was reduced subsequently with tin (II) chloride in acetic acid to yield the 4-amino compound (FIG. 9). Treatment of the 4-amino derivative with either HBr or HCl under Sandmeyer conditions yielded the 4-bromo and 4-chloro products, respectively. Alternatively, reaction of the 4-amino compound with formaldehyde and sodium borohydride provided the 4-dimethylamino derivative. Mono-acetylation of the 4-aminobenzimidazole derivative with acetic anhydride gave the 4-acetamido product. Subsequent alkylation of the 4-acetamido with methyl iodide yielded a mixture of N-methyl-N-acetamido and starting material. Deacylation of the N-methyl-N-acetamido under acidic conditions yielded the 4-methylamino compound.

Other compounds prepared for this series were made via synthetic modification of other intermediates. Bromination of 1-(2,6-difluorobenzoyl)-2-nitroanilide yielded 1-(2,6-difluorobenzoyl)-4-bromo-2-nitroanilide. This derivative was then benzylated and reductively cyclized with standard conditions to yield 1-(2,6-difluorobenzyl)-2-(2,6-difluorophenyl)-5-bromo-benzimidazole. Mono-nitration of 2-(2,6-difluorophenyl)benzimidazole with nitric acid at room temperature yielded the 5-nitro-benzimnidazole derivative as the only product. Alkylation with 2,6-difluorobenzyl bromide occurred regiospecifically to yield the 1-(2,6-difluorobenzyl)-2-(2,6-difluorophenyl)-5-nitro-benzimidazole.

FIG. 9 provides a schematic approach for the preparation of 1-(2,6-difluorobenzyl)-2-(2,6-difluorophenyl) benzimidazole substituted with chloro, bromo, nitro, amino, acetylamino, dimethylamino groups at the C-4 position of the benzimidazole ring. In this Figure, "a" comprises 2,6-difluorobenzoyl chloride, pyridine: TBF (1:1); "b" comprises AcOH reflux; "c" comprises 2,6-F$_2$-BnBr, NaH,THF; "d" comprises SnCl$_2$, AcOH, HCl; "e" comprises Ac$_2$O, THF; "f" comprises H$_2$CO, NaBH$_4$, H$_2$SO$_4$; and "g" comprises NaNO$_2$, HBr or HCl. As shown in this Figure, reduction of the 4-nitro group of 1-(2,6-difluorobenzyl)-2-(2,6-difluorophenyl)-4-nitrobenzimidazole (Example 83) was accomplished with tin (II) chloride, which gives 4-amino-1-(2,6-difluorobenzyl)-2-(2,6-difluorophenyl) benzimidazole 3300 (Example 85). Compound 3300 was used to prepare 4-bromo-1-(2,6-difluorobenzyl)-2-(2,6-difluorophenyl)benzimidazole (Example 86) and 4-chloro-1-(2,6-difluorobenzyl)-2-(2,6-difluorophenyl) benzimidazole (Example 87) via the Sandmeyer reactions (i.e., methods known in the art). Monoacylation of compound 3300 with acetic anhydride gave 1-(2,6-difluorobenzyl)-2-(2,6-difluorophenyl)-4-acetamidobenzimidazole (Example 88), while treatment of 3300 with formaldehyde and sodium borohydride yielded the dimethylamino compound 1-(2,6-difluorobenzyl)-2-(2,6-difluorophenyl)-4-N,N-dimethylaminobenzimidazole (Example 89).

Figure 14:
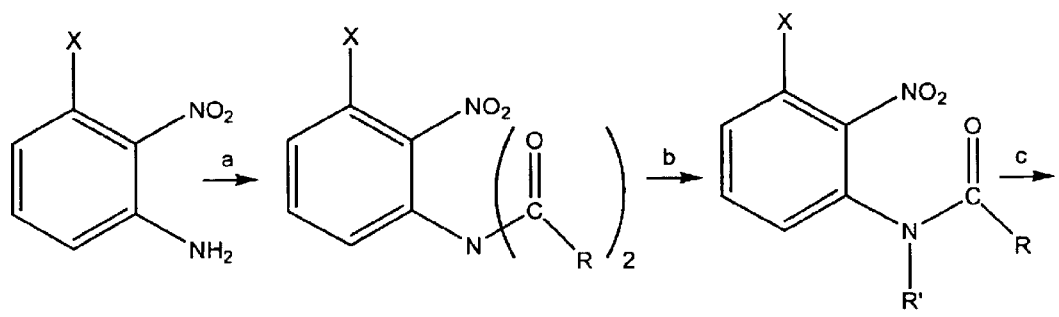
FIG. 14 is a schematic synthesis of 1-(2,6-difluorobenzyl)-2-(2,6-difluorophenyl)benzimidazoles of the present invention.
Figure 14:
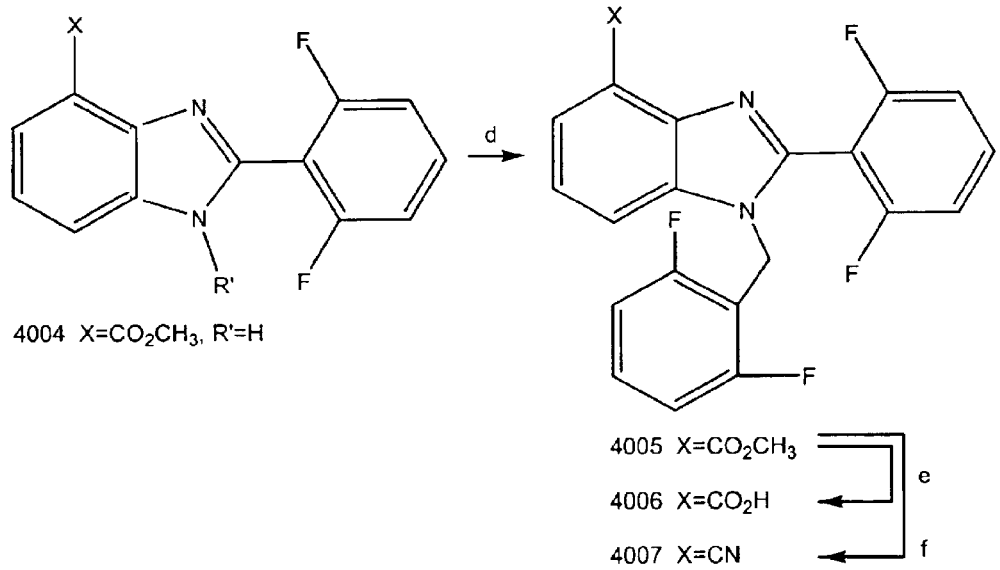

Furthermore, as depicted in FIG. 14, the 4-methyl ester (4005) was a key intermediate for a number of 4-substituted benzimidazole derivatives. In this Figure, "a" comprises difluorobenzoyl chloride, pyridine/THF; "b" comprises hydrazine, pyridine; "c" comprises iron powder; "d" comprises 2,6-difluoro-a-bromo-toluene; "e" comprises barium hydroxide/AcOH; and "f" comprises 1.0 M solution of AlMe$_2$NH$_2$, xylene.Treatment of the 4-methyl ester derivative with dimethylaluminium amine resulted in the 4-nitrile derivative. The 4-nitrile was used subsequently to prepare the 4-hydroxyamidino and 4-amido derivatives by hydrolysis with hydroxylamine and hydrogen peroxide, respectively. Bis methylation of the 4-amido derivative with sodium hydride and methyl iodide yielded the desired 4-(N,N-dimethyl)amido derivative. Alternatively, reaction of the 4-methyl ester derivative with barium hydroxide or methyl lithium yielded the 4-carboxylate and 4-isopropanol derivatives, respectively. Hydrolysis of the 4-isopropanol derivative with strong acid lead to the 4-isopropenyl in low yields. Reduction of the 4-methyl ester to yield the 4-hydroxymethy derivative, however, resulted in low yields under a number of reducing conditions (lithium aluminum hydride, NaBH$_4$, borane). Consequently, the reduction step was carried out earlier in the synthesis with the precursor, methyl-N-(2,6-difluorobenzoyl)-6-nitro-2-anilide-carboxylate. Protection of the 2-hydroxymethyl-6-nitroanilide with acetic anhydride and subsequent modification as done with the 4-methyl ester led to the desire 4-hydroxy methyl benzimidazole derivative. This product was subsequently converted to the 4-formyl, 4-chloromethyl, 4-azidomethyl, 4-aminomethyl, 4-acetamidomethyl and 4-(N-methyl)acetamido derivatives.

Figure 15:
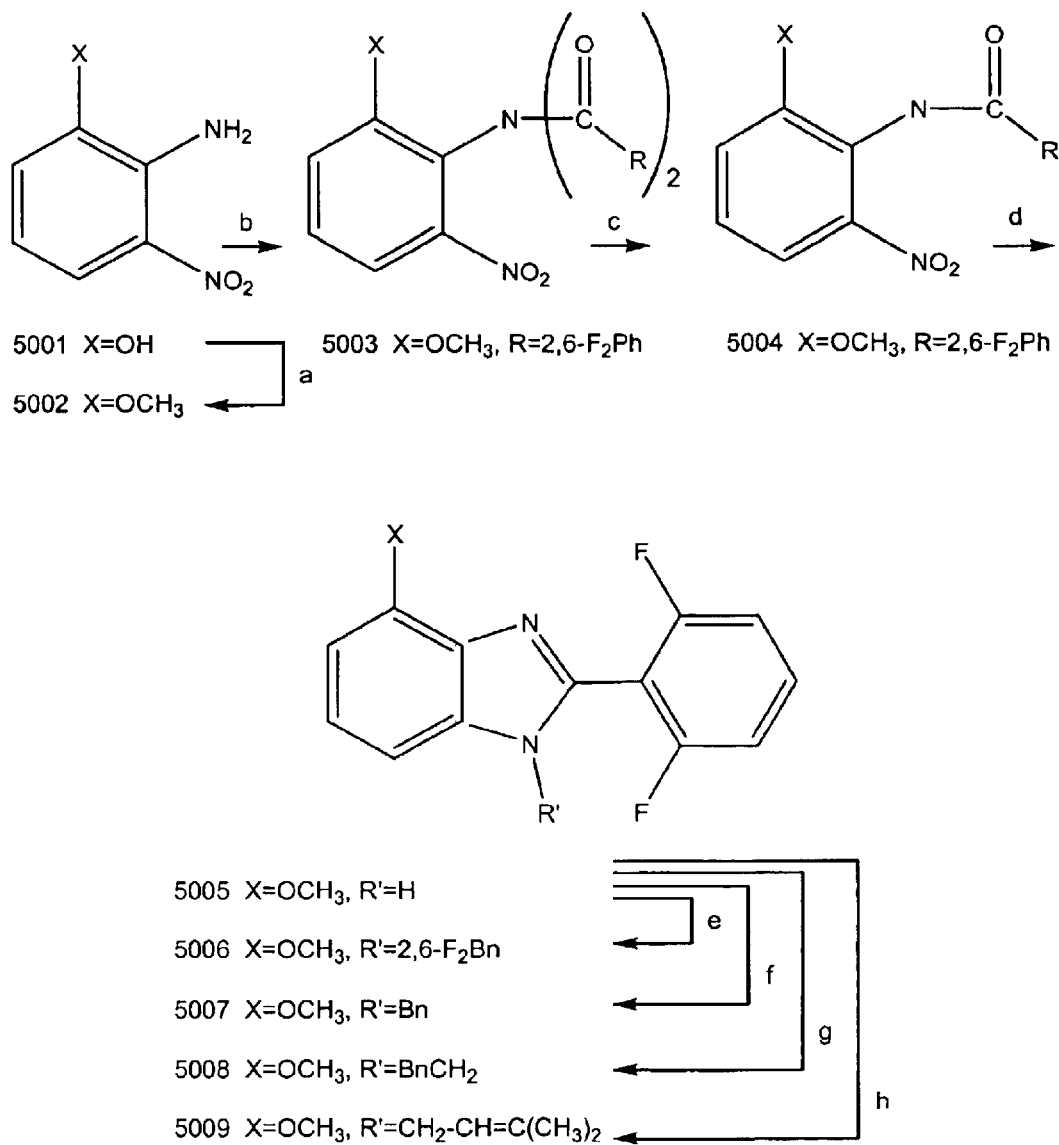
FIG. 15 is a schematic synthesis of N-substituted-2-(2,6-difluorophenyl)-4-methoxylbenzimidazoles.

FIG. 15 provides a schematic approach for the synthesis of 1-(2,6-difluorobenzyl)-2-(2,6-difluorophenyl)-4-methoxybenzimidazole and 2-(2,6-difluorophenyl-4-methoxylbenzimidazoles. In this Figure, "a" comprises K$_2$CO$_3$, methyl iodide, acetone; "b" comprises difluorobenzoyl chloride, pyridine/THF; "c" comprises hydrazine, pyridine; "d" comprises iron powder; "e" comprises 2,6-difluoro-a-bromo-toluene; "f" comprises benzyl bromide; "g" comprises (1-bromoethyl)benzene; and "h" comprises 3,3-dimethylallyl bromide.

Figure 16:
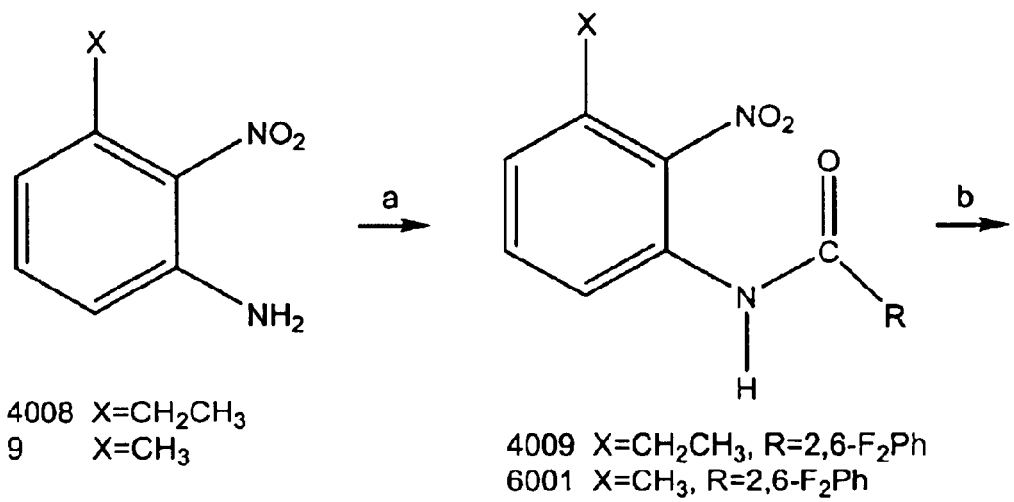
FIG. 16 is a schematic syntheses of N-substituted-(2,6-difluorophenyl)-4-methylbenzimidazoles and N-substituted-(2,6-difluorophenyl)-4-ethylbenzimidazoles.
Figure 16:
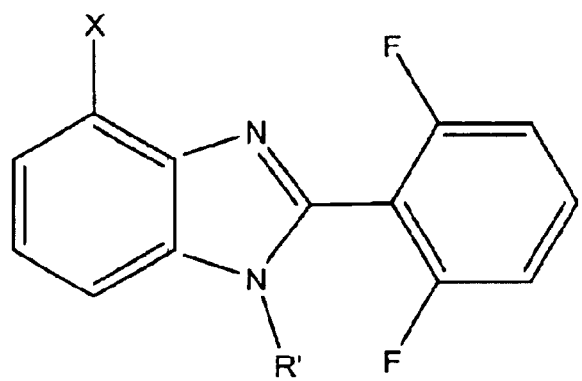
Figure 16:
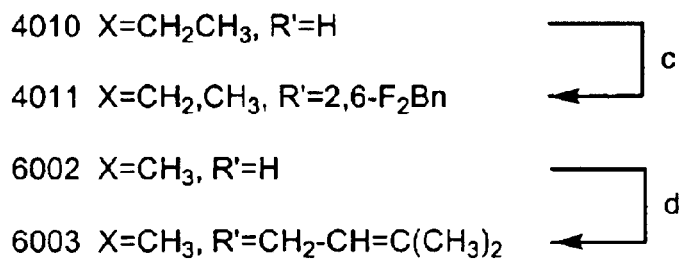

FIG. 16 provides a schematic approach for the synthesis of 2-(2,6-difluorophenyl)-4-ethylbenzimidazoles and 2-(2,6-difluorophenyl)-4-methylbenzimidazoles. In this Figure, "a" comprises difluorobenzoyl chloride; "b" comprises iron powder; "c" comprises 2,6-difluoro-a-bromo-toluene; and "d" comprises 3,3-dimethylallyl bromide.

Figure 17:
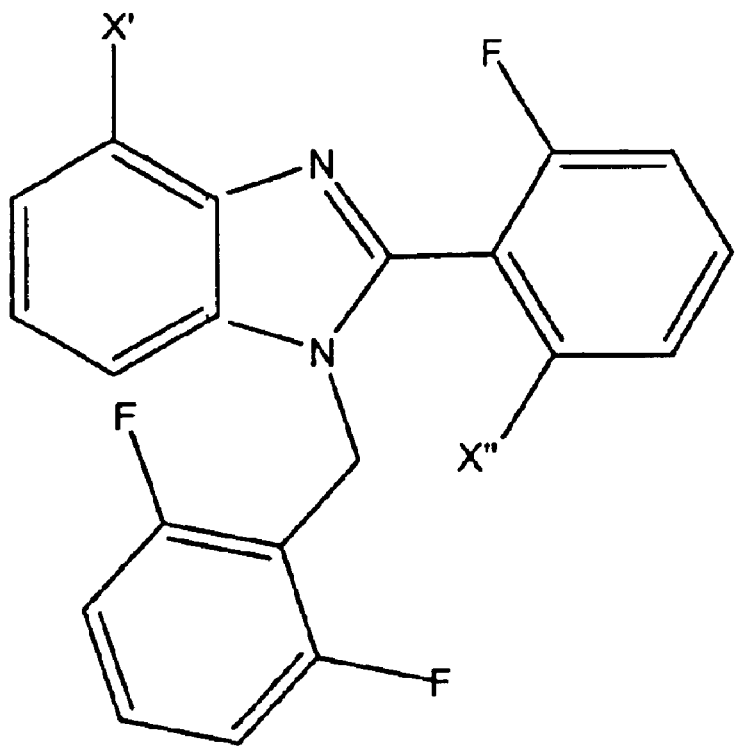
FIG. 17 is a schematic synthesis of substituted 1-(2,6-difluorobenzyl)-2-arylbenzimidazoles.

FIG. 17 provides a schematic approach for the synthesis of 1-(2,6-difluorobenzyl)-2-(2,6-difluorophenyl)-4-(N-substituted)benzimidazole (e.g., benzimidazoles substituted with NHAc, MeNAc, and MeNH). In this Figure, "a" comprises SnCl$_2$x2H$_2$O; "b" comprises methyl iodide, TIF, NaH; and "c" comprises HCl.

Figure 18:
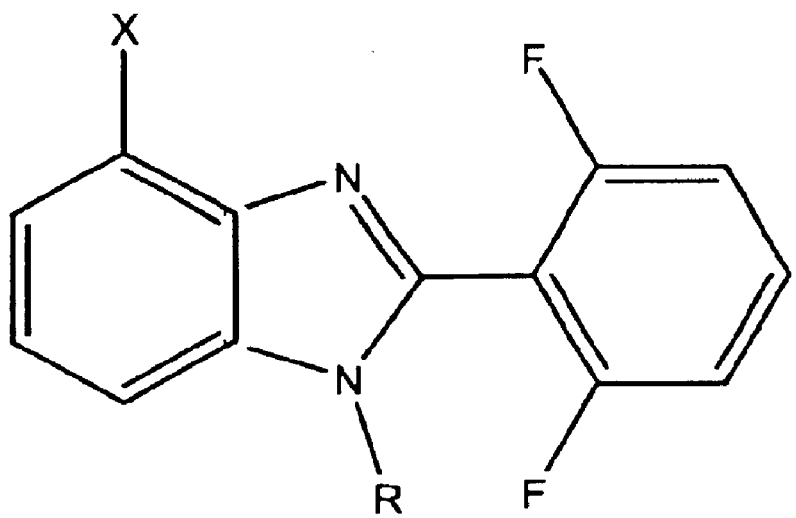
FIG. 18 is a schematic synthesis of 4-substituted N-substituted-2-(2,6-difluorophenyl)benzimidazoles.

FIG. 18 provides a schematic approach for the synthesis of other substituted benzimidazole compounds. In this Figure, "a" comprises 3,3-dimethylallyl bromide; "b" comprises iron powder; and "c" comprises concentrated H$_2$SO$_4$.

Figure 19:
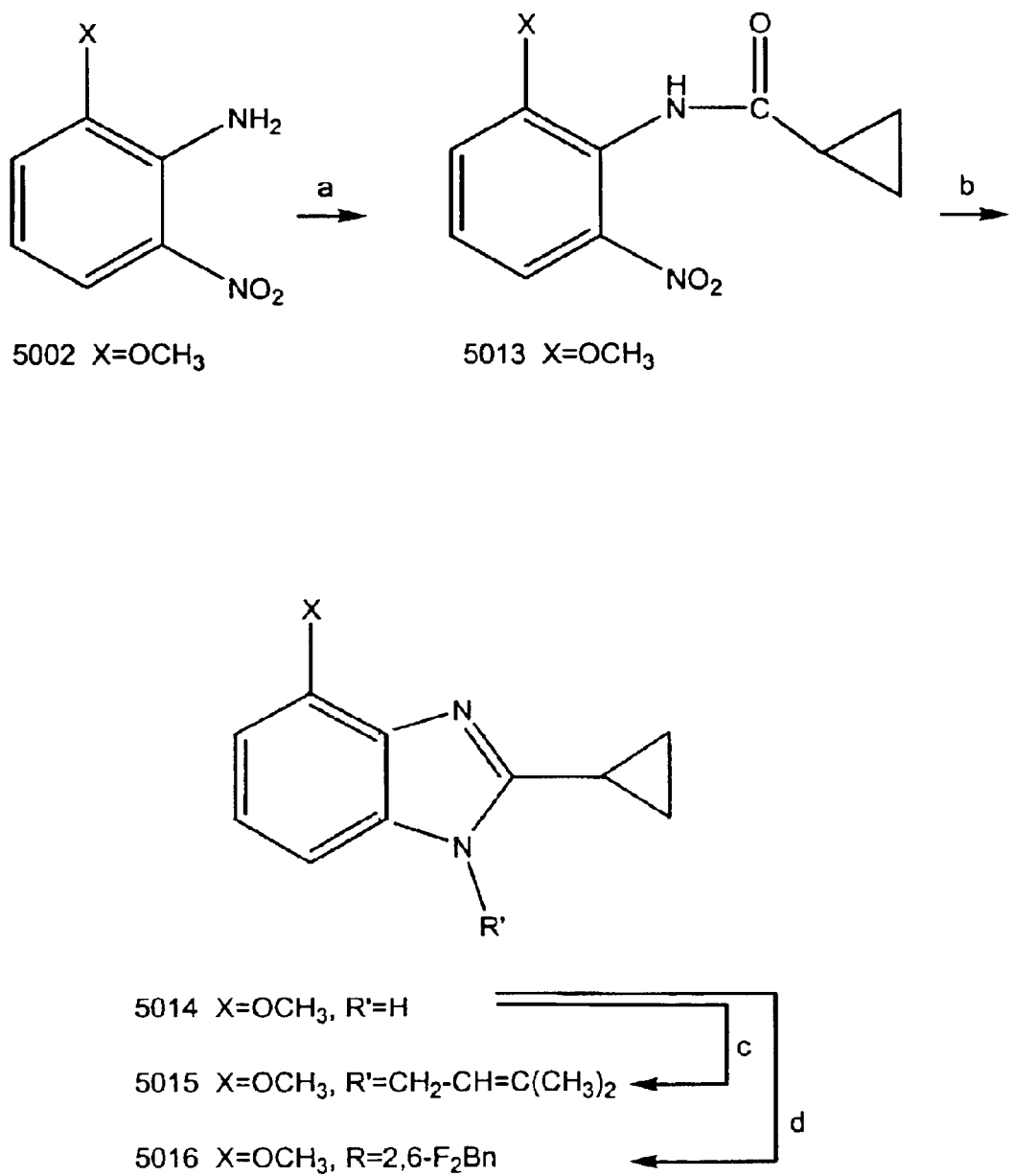
FIG. 19 is a schematic synthesis of N-substituted-2-(cyclopropyl)-4-methoxylbenzimidazoles.
Figure 20:
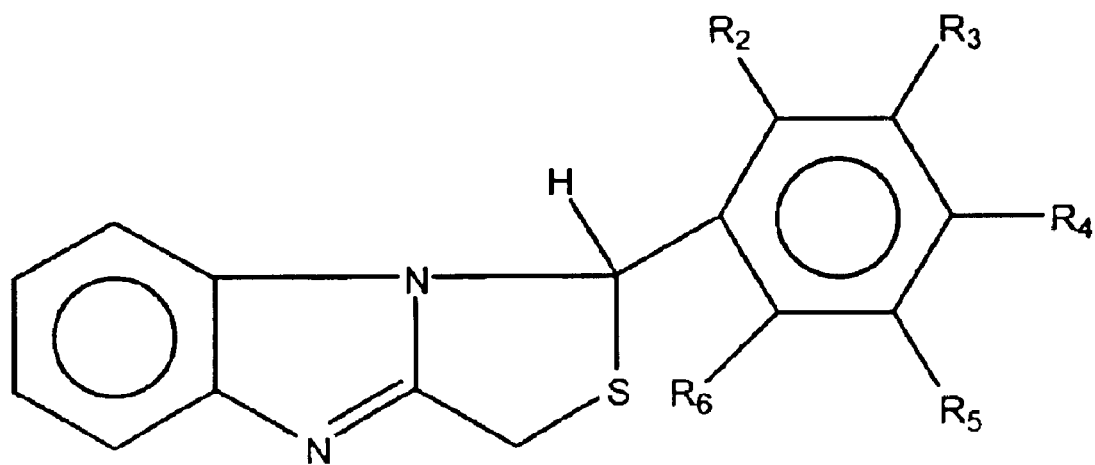
FIG. 20 shows the structure of 1H, 3H-thiazolo[3,4-a] benzimidazoles.

In addition, other substituted benzimidazoles were prepared. For example, FIG. 19 provides a schematic synthesis of 1-(2,6-difluorobenzyl)-2-(cyclopropyl)-4-methoxylbenzimidazole (Example 49). In this Figure, "a" comprises cyclopropanecarbonyl chloride; "b" comprises iron powder; "c" comprises 3,3-dimethylallyl bromide; and "d" comprises 2,6-difluoro-a-bromo-toluene.

The series of compounds synthesized as described above, were analyzed in order to determine whether the position and nature of the substituents on the benzyl ring at N-1, were analogous to those in the TBZ series. Treatment of 2-(2,6-difluorophenyl)benzimidazole (18) or 2-(2,6-difluorophenyl)-4-methylbenzimnidazole (19) with benzyl bromide or its analogs (e.g., 2,6-dichloro-α-bromo-toluene, 2,3,4,5,6-pentafluoro-α-bromo-toluene), gave compounds with hydrogen, chlorine, or multiple fluorines on the N1 benzyl ring, which were compared for their ability to inhibit HIV-1 RT. Since a number of NNRTI contain sulfonyl links (e.g., 2-nitrophenyl phenyl sulfone, and 5-chloro-3-(phenylsufonyl)-indole-2-carboxamide), it was also determined whether a sulfonyl group could replace the methylene linker in 1-(2,6-difluorobenzyl)-2-(2,6-difluorobenzyl)-4-methylbenzimidazole (33). By reacting compounds 18 or 19 with benzenesulfonyl chloride, 1-benzenesulfonyl-2-(2,6-difluorophenyl)benzimidazole (Example 37) and 1-benzenesulfonyl-2-(2,6-difluorophenyl)4-methylbenzimidazole (Example 38) were obtained in good yields. Similarly, treatment of compound 18 with 2,6-difluorobenzoyl chloride provided the N-2,6-difluorobenzoate derivative 1-(2,6-difluorobenzoyl)-2-(2,6-difluorophenyl)benzimidazole (Example 39), allowing the testing of carbonyl as a linker. In addition, introduction of nitrogen into the N1-benzyl ring was investigated. The 3-pyridyl derivative was synthesized via alkylation with α-bromo-methylpyridine, to yield 1-(3-pyridylmethyl)-2-(2, 6-difluorophenyl)-4-methylbenzimidazole (Example 35). In this series, the optimal anti-HIV activity was achieved when the phenyl ring was substituted at the 2 and 6 position with fluorine.

It is not intended that the substituted benzimidazoles be limited to those compounds described above. It is contemplated that 1-(2,6-difluorobenzyl)-2-(2,6-difluorobenzyl) benzimidazoles having 4-methylenethiocyanate (CH$_2$NCS) and 4-methyleneacetylene (CH$_2$CCH) will be used in the compositions and methods of the present invention. The chemical structures of some substituted benzimidazoles of the present invention are shown at Table 13.

TABLE 13

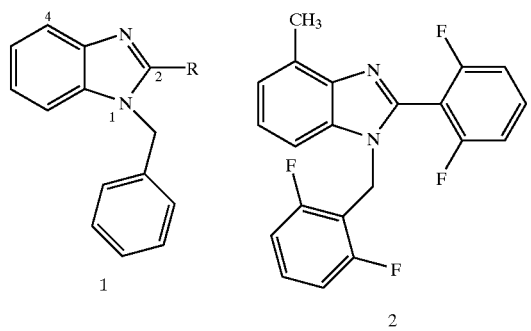

TABLE 13-continued

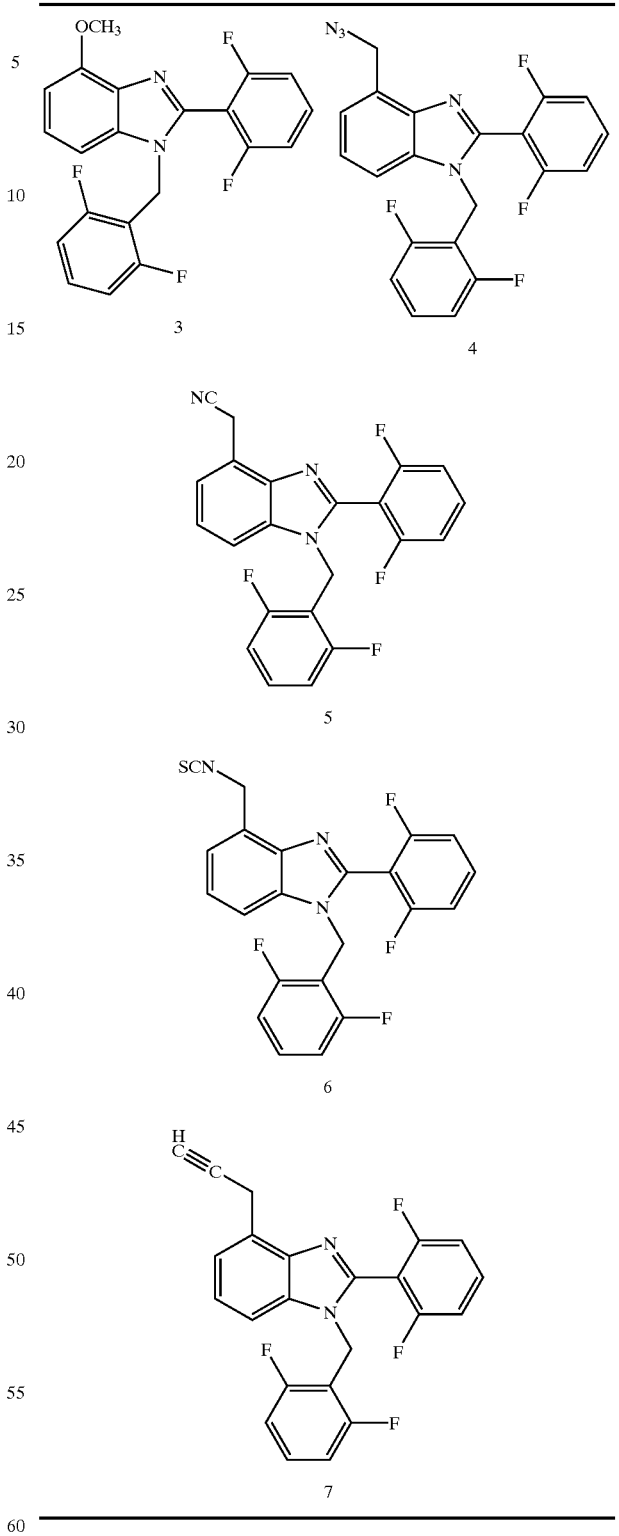

C. Pharmaceutical Compositions

The present invention contemplates using pharmaceutical compositions comprising the substituted benzimidazoles described above. The pharmaceutical compositions are composed of one or more pharmaceutically acceptable diluents, excipients or carriers, and are well-known to those skilled in the art (See e.g., U.S. Pat. No. 5,356,917, supra).

It is not intended that the present invention be limited by the particular nature of the therapeutic preparation. For example, such compositions can be provided together with physiologically tolerable liquid (e.g., saline), gel or solid carriers or vehicles, diluents, adjuvants and excipients, such as pharmaceutical grades of mannitol, lactose, starch, magnesium stearate, sodium saccharin, cellulose, magnesium carbonate, and the like. These compositions typically contain 1%–95% of active ingredient, preferably at least 2%–70%. In addition, the compositions may contain minor amounts of auxiliary substances such as wetting or emulsifying agents, stabilizing or pH buffering agents or preservatives if desired. The therapeutic compositions contemplated by the present invention are physiologically tolerable and compatible. These therapeutic preparations can be administered to humans in a manner similar to other therapeutic agents. In general, the dosage required for therapeutic efficacy will vary according to the type of use and mode of administration, as well as the particularized requirements of individual hosts (e.g., age, gender, weight, etc.). The preferred mode of administration of these preparations depends on several factors, including the stability of the preparation, the bioavailability of the compound following different routes of administration, and the frequency of dosing.

III. Biological Activity of Substituted Benzimidazoles

A. RT Inhibition By 1- And 2-Substituted Benzimidazoles

The testing of the 2-aryl-1-(2,6-diflurobenzyl)-benzimidazoles for their HIV-1 RT inhibition activity indicated that a number of aromatic systems were tolerated at the C2 position. The structure, physical and biological data for 1 and 2-substituted benzimidazoles are shown in Tables 1–3. In these Tables, the $IC_{50}(\mu M)$ column indicates the quantity of drug required to reduce WT RT enzyme activity by 50% ($IC_{50}$).

TABLE 1

| No. | X | R' | formula | mp, °C. | anal. | % inhibn (10 $\mu$M) | $IC_{50}$ ($\mu$M) |
|---|---|---|---|---|---|---|---|
| 39 | H | Ph | $C_{20}H_{14}F_2N_2$ | 127–129 | C, H, N | 77 | 16 |
| 26 | H | 2,6-$F_2$Ph | $C_{20}H_{12}F_4N_2$ | 138–140 | C, H, N | 93 | 0.11 |
| 33 | $CH_3$ | 2,6-$F_2$Ph | $C_{21}H_{14}F_4N_2$ | 182–186 | C, H, N | 92 | 0.20 |
| 36 | H | 2-$CH_3$—Ph | $C_{21}H_{16}F_2N_2$ | 138–140 | C, H, N | 71 | |
| 41 | $CH_3$ | 4-Py | $C_{20}H_{15}F_2N_3$ | 171–172 | C, H, N | 70 | |
| 40 | $CH_3$ | 3-Py | $C_{20}H_{15}F_2N_3$ | 186–188 | C, H, N | 35 | |
| 4007 | $CH_3$ | 4-CN—Ph | $C_{22}H_{15}F_2N_3$ | 207–208 | C, H, N | 26 | |
| 37 | $CH_3$ | 1-Nap | $C_{25}H_{18}F_4N_3$ | 121–123 | C, H, N | 2 | |
| 38 | $CH_3$ | 2-Nap | $C_{25}H_{18}F_4N_3$ | 175–176 | C, H, N | 8 | |
| TZB | | | $C_{15}H_{10}F_2N_2S$ | | | 84 | 0.5 |

TABLE 2

| No. | X | R" | formula | mp, °C. | anal. | % inhibn (10 $\mu$M) | $IC_{50}$ (10 $\mu$M) |
|---|---|---|---|---|---|---|---|
| 26 | H | 2,6-$F_2$Bn | $C_{20}H_{12}F_4N_2$ | 138–140 | C, H, N | 93 | 0.11 |
| 33 | $CH_3$ | 2,6-$F_2$Bn | $C_{21}H_{14}F_4N_2$ | 182–186 | C, H, N | 92 | 0.20 |
| 28 | H | Bn | $C_{20}H_{14}F_2N_2$ | 122–125 | C, H, N | 71 | 18.6 |
| 29 | $CH_3$ | Bn | $C_{21}H_{16}F_2N_2$ | 112–117 | C, H, $N^a$ | 87 | 1.6 |
| 30 | $CH_3$ | 2,6-$Cl_2$Bn | $C_{21}H_{14}Cl_2F_2N_2$ | 202–203 | C, H, N | 58 | |
| 42 | $CH_3$ | 2,3,4,5,6-$F_5$Bn | $C_{21}H_{11}F_7N_2$ | 155–156 | C, H, N | 36 | |
| 43 | $CH_3$ | $CH_2$(3-Py) | $C_{20}H_{15}F_4N_3$ | 131–132 | C, H, N | 43 | |
| 45 | H | $PhSO_2$ | $C_{19}H_{12}F_2N_2SO_2$ | 104–106 | C, H, N | 52 | |
| 46 | $CH_3$ | $PhSO_2$ | $C_{20}H_{14}F_2N_2SO_2$ | 134–135 | C, H, N | 39 | |
| 47 | H | 2,6-$F_2$Bz | $C_{20}H_{10}F_4N_2O$ | 144–146 | C, H, N | 8 | |

TABLE 3

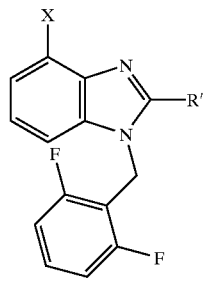

| No. | X | R' | formula | mp, °C. | anal. | % inhibn (10 μM) |
|---|---|---|---|---|---|---|
| 39 | H | Ph | $C_{20}H_{14}F_2N_2$ | 127–129 | C, H, N | 77 |
| 50 | $CH_3$ | CHO | $C_{16}H_{12}F_2N_2O$ | 144–146 | C, H, N | 59 |
| 34 | $CH_3$ | iPr | $C_{18}H_{18}F_2N_2$ | 151–153 | C, H, N | 53 |
| 49 | $CH_3$ | H | $C_{15}H_{12}F_2N_2$ | 98–100 | C, H, N | 40 |
| 35 | H | $CH_3$ | $C_{15}H_{12}F_2N_2$ | 99–100 | C, H, N | 22 |
| 48 | $CH_3$ | $CH_2OH$ | $C_{16}H_{14}F_2N_2O$ | 203–205 | C, H, N | 12 |
| 32 | H | $CH_2O(2,6-F_2Bn)$ | $C_{22}H_{16}F_4N_2O$ | 107–109 | C, H, N | 7 |

As shown in Table 2, the ability to inhibit wild type RT (WTRT) by the hydrogen (50), methyl (35), hydroxymethyl (49), isopropyl (34), formyl (51), phenyl (39), and bis-2,6-difluorobenzyl (32) compounds was measured as the percent inhibition of nucleotide incorporation into an rC-dG template primer at 10 μmolar drug concentration. Except for compound 39 where the C2 was phenyl, all the substituents at the 2 position failed to appreciably inhibit HIV-1 RT. Substitution of the phenyl with fluorine at the 2 and 6 positions (i.e., compound 33) gave the best inhibition with $IC_{50}$=200 nM. The results for TIBO and TBZ in this Table are in contrast with those reported by Pauwels et al. (Pauwels et al., "New Tetrahydroimidazo[4,5,1-jk][1,4]-Benzodiazepin-2(1H)-One and Thione Derivatives are Potent Inhibitors of Human Immunodeficiency Virus type 1 Replication and are Synergistic with 2',3'-Dideoxynucleoside Analogs," *Antimicrob. Agents Chemother.*, 38:2863–2870 [1994]), who reported an $IC_{50}$ for rC:dG of 0.06 μM for TIBO, and Buckheit et al. (Buckheit et al., "Thiazolobenzimidazole: Biological and Biochemical Anti-retroviral Activity of a New Nonnucleoside Reverse Transcriptase Inhibitor," *Antiviral Res.*, 21:247–265 [1993]), who reported an $IC_{50}$ for rC:dG of 0.5 μM for ribosomal RNA.

Although knowledge of the precise mechanism is not necessary to successfully practice the invention, it is contemplated that because the fluorines do not dramatically alter the size of the 2-phenyl ring, the four-fold increase in inhibitory activity observed for compound 26 in comparison with compound 39 (See, Table 1) probably represents some alteration in the aromatic interactions between the 2,6-difluorophenyl ring and the aromatic side chain residues surrounding the NNRTI binding pocket. Less conservative changes, such as the addition of an ortho-methyl to the 2-phenyl ring, led to a two-fold decrease in RT inhibition (See e.g., 36, Table 1). This decrease in RT inhibition led to the examination of other planar aromatic systems. For example, changing the 2-phenyl to the 4-pyridyl resulted in almost no change in the $IC_{50}$ value. (See e.g., compounds 39 and 41, Table 1). These results indicate that some heteroaromatic systems can be introduced at C2 without penalty. However, the 3-pyridyl compound 40 (See, Table 1) showed considerably less activity. While it is again not necessary to understand precise mechanisms in order to use the various embodiments of present invention, it is possible that the lone pair of electrons on the 4-pyridyl system can be accommodated, in contrast to the use of the 3-pyridyl compound, in which unfavorable interactions result. Larger aromatic moieties at C2 (e.g., naphthyl), regardless of orientation, were found to result in complete loss of inhibitory activity, indicating that there was a limit to the size of the inhibitor NNRTI binding pocket can accommodate. These observations led to the development of compounds with $IC_{50}$s in the micromolar range (e.g., as shown in Tables 1 and 2).

Furthermore, benzenesulfonyl and benzoate derivatives (45, 46, and 47) did not show appreciable RT inhibition activity. Substitution on the phenyl ring by a pyridine ring (43) similarly led to lower inhibition. Removal of the fluorine at the 2 and 6 position (28 or 29), or its replacement with chlorine (30) also resulted in a decrease in inhibition. Likewise, addition of more fluorines on the benzyl ring (42) yielded a compound showing greatly decreased inhibition activity. (See, Table 2)

B. Testing of 1-(2,6-difluorobenzyl)-2-(2,6-difluorophenyl)Benzimidazoles Against Reverse Transcriptase The structure, physical and enzyme inhibition data for 1-(2,6-difluorobenzyl)-2-(2,6-difluorophenyl)-benzimidazoles are shown in Tables 5–7 and 11. Testing of the 4,5- and 4,6-di-substituted and mono-substituted benzimidazoles was determined by measuring the relative nucleotide incorporation using an rC-dG template primer at 1 μmol drug concentration (10-fold lower than used above), to the amount of incorporation with no inhibitor present utilizing WT HIV-1 RT.

TABLE 5

| No. | X | formula | mp, °C. | anal. | % inhibn (1 μM) |
|---|---|---|---|---|---|
| 2 | H | $C_{20}H_{12}F_4N_2$ | 138–140 | C, H, N | 50 |
| 1 | 4-$CH_3$ | $C_{21}H_{14}F_4N_2$ | 182–186 | C, H, N | 71 |
| 41 | 5-$CH_3$ | $C_{21}H_{14}F_4N_2$ | 147–149 | C, H, N | 22 |
| 42 | 6-$CH_3$ | $C_{21}H_{14}F_4N_2$ | 172–173 | C, H, N | 42 |
| 43 | 7-$CH_3$ | $C_{21}H_{14}F_4N_2$ | 177–178 | C, H, N | 1 |
| 45 | 4,5-di-$CH_3$ | $C_{22}H_{16}F_4N_2$ | 176–177 | C, H, N | 26 |
| 46 | 4,6-di-$CH_3$ | $C_{22}H_{14}F_4N_2$ | 153–154 | C, H, N | 37 |

% inhibition is average of two experiments done in triplicates

TABLE 6

| No. | X | formula | mp, °C. | anal. | % inhibn (1 μM) |
|---|---|---|---|---|---|
| 54 | 4-Br | $C_{20}H_{11}BrF_4N_2$ | 147–148 | C, H, N | 78 |
| 38 | 5-Br | $C_{20}H_{11}BrF_4N_2$ | 155–156 | C, H, N | 43 |
| 55 | 4-Cl | $C_{20}H_{11}ClF_4N_2$ | 163–164 | C, H, N | 75 |
| 39 | 5-Cl | $C_{20}H_{11}ClF_4N_2$ | 136–137 | C, H, N | 48 |
| 40 | 6-Cl | $C_{20}H_{11}ClF_4N_2$ | 152–153 | C, H, N | 69 |
| 48 | 4-NO$_2$ | $C_{20}H_{11}F_4N_2O_2$ | 168–170 | C, H, N | 51 |
| 49 | 5-NO$_2$ | $C_{20}H_{11}F_4N_3O_2$ | 168–169 | C, H, N | 30 |

% inhibition is average of two experiments done in triplicates

TABLE 7

| No. | R | formula | mp, °C. | anal. | % inhibn (1 μM) | IC$_{50}$ (μM) | EC$_{50}$ (μM) |
|---|---|---|---|---|---|---|---|
| 33 | CH$_3$ | $C_{21}H_{14}F_4N_2$ | 182–186 | C, H, N | 71 | 0.20 | 0.44 |
| 5006 | OCH$_3$ | $C_{21}H_{14}F_4N_2O$ | 154–155 | C, H, N | 85 | 0.0073 | 0.0046 |
| 5011 | NAcCH$_3$ | $C_{23}H_{17}F_4N_3O$ | 155–156 | C, H, N | 77 | 0.32 | 0.02 |
| 4011 | CH$_2$CH$_3$ | $C_{22}H_{16}F_4N_2$ | 165–166 | C, H, N | 50 | 17.5 | 0.82 |
| 3100 | NO$_2$ | $C_{20}H_{11}F_4N_3O$ | 168–170 | C, H, N | 51 | 1.88 | 2.40 |
| 3300 | NH$_2$ | $C_{20}H_{13}F_4N_3$ | 168–170 | C, H, N | 69 | 0.28 | 0.46 |
| 3400 | Br | $C_{20}H_{11}BrF_4N_2$ | 147–148 | C, H, N | 78 | 1.61 | 0.37 |
| 3500 | Cl | $C_{20}H_{11}ClF_4N_2$ | 163–164 | C, H, N | 75 | 2.63 | 0.44 |
| 3600 | NHAc | $C_{22}H_{15}F_4N_3O$ | 194–195 | C, H, N | 24 | 54.7 | 1.48 |
| 5012 | NHCH$_3$ | $C_{21}H_{15}F_4N_3$ | 194–195 | C, H, N | 24 | 4.94 | 1.70 |
| 3700 | N(CH$_3$)$_2$ | $C_{22}H_{17}F_4N_3$ | 155–156 | C, H, N | 77 | 40.0 | 2.37 |

TABLE 11

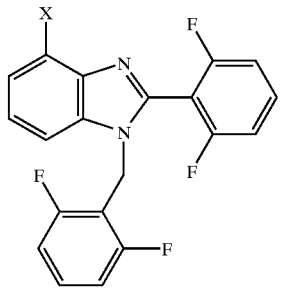

| No. | X | formula | mp, °C. | anal. | IC$_{50}$ ($\mu$M) | EC$_{50}$ ($\mu$M) |
|---|---|---|---|---|---|---|
| 1 | CH$_3$ | C$_{21}$H$_{14}$F$_4$N$_2$ | 182–186 | C, H, N | 0.20 | 0.44 |
| 2 | H | C$_{20}$H$_{12}$F$_4$N$_3$ | 138–140 | C, H, N | 0.11 | 1.70 |
| 44 | OCH$_3$ | C$_{21}$H$_{14}$F$_4$N$_2$O | 154–155 | C, H, N | 0.0073 | 0.06 |
| 57 | NAcCH$_3$ | C$_{23}$H$_{17}$F$_4$N$_2$O | 155–156 | C, H, N | 0.32 | 0.02 |
| 47 | CH$_2$CH$_3$ | C$_{22}$H$_{14}$F$_4$N$_2$ | 165–166 | C, H, N | 17.5 | 0.82 |
| 48 | NO$_2$ | C$_{25}$H$_{11}$F$_4$N$_3$O$_2$ | 168–170 | C, H, N | 1.88 | 2.40 |
| 50 | CO$_2$Me | C$_{22}$H$_{14}$F$_4$N$_2$O$_2$ | 184–186 | C, H, N | ND | NRVC |
| 51 | CH$_2$OAc | C$_{21}$H$_{14}$F$_4$N$_2$O$_2$ | 126–127 | C, H, N | ND | 0.059 |
| 52 | OH | C$_{20}$H$_{12}$F$_4$N$_2$O | 257–259 | C, H, N | ND | 0.65 |
| 53 | NH$_2$ | C$_{20}$H$_{12}$F$_4$N$_3$ | 168–170 | C, H, N | 0.28 | 0.46 |
| 54 | Br | C$_{25}$H$_{11}$BrF$_4$N$_2$ | 147–148 | C, H, N | 1.61 | 0.37 |
| 55 | Cl | C$_{25}$H$_{11}$ClF$_4$N$_2$ | 163–164 | C, H, N | 2.63 | 0.44 |
| 56 | NHAc | C$_{22}$H$_{13}$F$_4$N$_2$O | 194–195 | C, H, N | 54.7 | 1.48 |
| 58 | NHCH$_3$ | C$_{21}$H$_{15}$F$_4$N$_2$ | 194–195 | C, H, N | 4.94 | 1.70 |
| 59 | N(CH$_3$)$_2$ | C$_{22}$H$_{17}$F$_4$N$_3$ | 155–156 | C, H, N | 40.0 | 2.37 |
| 60 | CN | C$_{22}$H$_{18}$F$_4$N$_3$ | 156–157 | C, H, N | ND | 0.43 |
| 61 | CNH(NH$_2$OH) | C$_{21}$H$_{14}$F$_4$N$_4$O | 213–216 | C, H, N | ND | 0.19 |
| 62 | CONH$_2$ | C$_{21}$H$_{13}$F$_4$N$_3$O | 260–261 | C, H, N | ND | 4.90 |
| 63 | CON(CH$_3$)$_2$ | C$_{23}$H$_{17}$F$_4$N$_2$O | 213–214 | C, H, N | ND | NRVC |
| 64 | CO$_2$H | C$_{21}$H$_{13}$F$_4$N$_2$O$_2$ | 179–180 | C, H, N | ND | NRVC |
| 65 | isopro | C$_{25}$H$_{14}$F$_4$N$_2$O | 149–150 | C, H, N | ND | 6.34 |
| 66 | isoprenyl | C$_{23}$H$_{12}$F$_4$N$_2$ | 156–158 | C, H, N | ND | 1.44 |
| 67 | CH$_2$OH | C$_{21}$H$_{10}$F$_4$N$_2$O | 157–158 | C, H, N | ND | 0.023 |
| 68 | CHO | C$_{21}$H$_{12}$F$_4$N$_2$O | 151–153 | C, H, N | ND | 0.12 |
| 69 | CH$_3$Cl | C$_{21}$H$_{12}$ClF$_4$N$_2$ | 143–144 | C, H, N | ND | 0.18 |
| 70 | CH$_2$N$_3$ | C$_{21}$H$_{12}$F$_4$N$_2$ | 150–152 | C, H, N | ND | 0.045 |
| 71 | CH$_2$NH$_2$ | C$_{21}$H$_{15}$F$_4$N$_2$ | 257–260 | C, H, N | ND | 0.037 |
| 72 | CH$_2$NHAc | C$_{12}$H$_{14}$F$_4$N$_2$O | 178–179 | C, H, N | ND | NRVC |
| 73 | CH$_2$NCH$_3$Ac | C$_{25}$H$_{12}$F$_4$N$_2$O | 171–172 | C, H, N | ND | 0.58 |
| 74 | CH$_2$OCH$_3$ | C$_{12}$H$_{12}$F$_4$N$_2$O |  | C, H, N | ND | ND |
|  | neviropine |  |  |  |  | 0.035 |

NRVC, no reduction in viral CPE
CEMSS/NL4-3

As seen in Table 5, most of the methyl derivatives inhibited RT activity in this enzyme based assay. In these tests, the enzyme assay was conducted with WT RT. Although it is not necessary to understand precise mechanisms in order to use the present invention, a change in percent (%) inhibition was noted as the methyl group is moved from the 4 to 7 positions. In the case of the 5- and 7-methyl derivatives, the % inhibition is dramatically decreased from the 4- and 6-methyl derivatives. The observed decrease determined for the 7-methyl might be due to the adoption of a different conformation from the 4-methyl owing to steric interactions between the 7-methyl and the N-1 benzyl group. Since the 5-methyl derivative can assume similar conformations as the 4-methyl and 6-methyl derivatives, the decrease in % inhibition determined for the 5-methyl compound is presumed to be due to differences in inductive effects. In the case of 4,5-dimethyl groups, the significant inhibition of 33 possessing a single methyl at C-4 was dramatically decreased by the presence of the C-5 methyl.

It was also observed that substitution at C-5 led to consistently less inhibition no matter what substituent was examined. A comparison of the inhibitory activities of the 4-, 5-, and 6-chloro compounds in Table 6 shows that the 5-chloro compound has approximately two-fold less activity than either the 4-chloro or 6-chloro benzimidazoles. A similar decrease is found when comparing the 4-bromo with the 5-bromo benzimidazoles, as well as when comparing the 4-nitro with the 5-nitro benzimidazoles. These data led to further examination of the substitution at the C-4 position.

As seen in Table 7, most 1-(2,6-difluorobenzyl)-2-(2,6-difluorophenyl)-benzimidazoles examined were able to inhibit RT in an assay utilizing WT RT enzyme. Three methods for the measurement of the inhibition of HIV-1 WT RT were used: i) the relative inhibition of nucleotide incorporation into a rC-dG template primer at 1 $\mu$mol drug concentration compared with the amount of incorporation with no inhibitor present; ii) the drug concentration required to inhibit 50% of nucleotide incorporation into a rC-dG template primer by HIV-1 WT RT (IC$_{50}$); and iii) the drug concentration required to reduce cell killing or virus production of HIV-1 WT RT by 50% (EC$_{50}$). The most potent inhibitor of HIV-1 WT RT by all three measurements of RT inhibition was the 4-methoxyl (IC$_{50}$=0.0073 $\mu$M and EC$_{50}$=

0.0046 µM). The $IC_{50}$ for the 4-methoxyl was found to be 100-fold more potent than the $IC_{50}$ for TZB and TIBO and is comparable to those determined for 8-Cl TIBO and nevirapine. Although the 4-methyl, 4-amino and 4-N-methylacetamido compounds all have similar $IC_{50}$ values ($IC_{50}$=0.20 µM, 0.28 µM, and 0.32 µM, respectively), the 4-N-methylacetamido compound is 20-fold more potent than the 4-methyl or 4-amino compounds as determined by the cytopathic cell killing assay ($EC_{50}$=0.02 µM).

As illustrated in Tables 5 and 6, the level of inhibitory activity dramatically differs as the regiochemistry of substituents changes from the 4 to 7 position. Substitution at the 4 position enhanced the inhibitory activity relative to the other sites of substitution, regardless of the type of substituent [$CH_3$ (1 vs 41–43), Br (54 vs 38), Cl (55 vs 39–40), $NO_2$ (48 vs 49)]. A combination of a C4 substituent ($CH_3$) with an additional substituent at the 5 or 6 positions (1 vs 45 and 1 vs 46) led to lowered inhibitory activity suggesting a preference for C4 mono-substitution. Substitution at the 7 position with a $CH_3$ (43), however, was completely detrimental to potency. Molecular modeling of the 7-$CH_3$ (43) vs the 4-$CH_3$ (1) suggests an alternative and possibly non-productive conformation for the 7-$CH_3$ (43) NNRTI as a consequence of steric interactions between the C7 substituent and the N1-2,6-difluorobenzyl group.

In light of these results, analogs in Table 11 were synthesized and tested to determine whether the potency enhancement of a C4 group was general for any substituent or related to some chemical or structural property of the substituent. Evaluation of these compounds for the inhibition of HIV-1 was determined as the fifty percent cell culture inhibitory concentration ($CIC_{50}$) in CEMSS cell culture with WT virus (NL4-3). While a variety of C4 substituents [($NH_2$ (53), Br (54), Cl (55), CN (60)] exhibited a modest potency-enhancing effect relative to the unsubstituted (2) or methyl (1) parent compounds, the methoxyl (44) substituent gave the best inhibition resulting in a dramatic 25-fold increase in the inhibitory activity against WT RT ($IC_{50}$=7.3 nM) over our lead compound (1). In contrast, the isosteric ethyl (47) and mono-methyl amino (58) were significantly poorer inhibitors.

Analogs 50, 57–58 and 61–64 were synthesized and tested to determine whether an oxygen in any other type of substituent would exhibit potency-enhancing effects. Placing an N-methyl acetamide (57) at the C4 position significantly enhanced inhibitory potency while other carbonyl groups [$CO_2Me$ (50), CNHNHOH (61), $CONH_2$ (62), CON$(CH_3)_2$ (63), and $CO_2H$ (64)] were clearly detrimental to potency. Synthesis of compounds 65–73 and determination of each analog's $CIC_{50}$ value focused attention on whether hydrophobic or a methylene insert at the C4 position would show similar inhibitory effects as the des-methylene analogs (53–57). These results suggested In addition to obtaining $CIC_{50}$ values against WT virus, the most active compounds were evaluated against MT-4 cells infected with HIV-1 variants containing amino acid substitutions in RT (Table 4). Comparison of the 4-methyl (1)[1] with the methoxyl (44), ethyl (47), nitro (48), amino (53), bromo (54), chloro (55), acetamido (56), and dimethylamino (59) analogs revealed that the potent 4-methoxyl compound (44) retained the best activity against the different RT variants examined in the cytopathic cell killing assay. None of the different amino acid substitutions in RT dramatically decreased the inhibitory activity, except for the K100E and V108I variants. As is common with most NNRTI, the 4-methoxyl compound (44) failed to show any activity against the K103N mutation.

As indicated above, maximum enzyme inhibition is obtained with compounds containing a C4 substituent. Although it is not necessary to understand the mechanism in order to practice the present invention, and it is not intended that the present invention be so limited, it is possible that the small change in $IC_{50}$'s reflects the ability of the NNRTI binding pocket to adjust in a way that maximizes the interaction with compounds having a C4 substituent.

Furthermore, the 1-(2,6-difluorobenzyl)-2-(2,6-difluorophenyl) substituted benzimidazoles of the present invention were compared against the clinically useful drugs (e.g., nevirapine) in Table 11. While nevirapine is active against many HIV-1 variant isolates, the 4-methoxyl compound (44) retains activity comparable with nevirapine while maintaining activity against the clinically important Y181C mutation. Although it is not necessary to understand the mechanism in order to practice the present invention, and it i not intended that the present invention be so limited, it is possible that the ability to inhibit the different HIV-1 virus isolates tested reflects the flexible nature of the 1-(2,6-difluorobenzyl)-2-(2,6-difluorophenyl)-benzimidazole system to better compensate for the different structural changes arising as a consequence of amino acid changes in RT binding pocket.

C. Cytopathic Cell Killing Assay

In depth biological evaluation of the RT inhibitory properties of the most active 4-substituted 1-(2,6-difluorobenzyl)-2-(2.6-difluorophenyl)benzimidazole compounds was determined with cultured MT-4 cells infected with WT and HIV-1 variants containing amino acid substitutions in RT, as described in Example 91 (See, Yang et al., "Characteristics of a Group of Nonnucleoside Reverse Transcriptase Inhibitors with Structural Diversity and Potent Anti-Human Immunodeficiency Virus Activity," *Leukemia* 9:S75–S85 [1995]). The cross-resistance profiles of the different compounds are presented in Tables 4 and 8–10. In these Tables, antiviral data are reported as the quantity of drug in µM required to reduce cell killing or virus production by 50% ($EC_{50}$). The various HIV isolates tested in the Figures are those corresponding to wild-type virus (NL4-3) and the other strains listed by their RT mutations. The three 4×AZT isolates included in the Figures represent AZT drug-resistant variants. For example, the 4×AZT/L100I isolate has five mutations: four mutations confer increased resistance to AZT, and the other mutation is located within the NNRTI binding pocket. TZB and nevir. (nevirapine) are two well-known NNRTIs, included in this experiment for comparison purposes. As shown in Table 4, the 4-methyl derivative 33 was consistently 3- to 4-fold better in the inhibition of the various viral isolates examined than the des-methyl analog 26. The increased inhibition observed for 33 suggested that substituents on the benzimidazole ring can significantly improve binding of this class of compounds to the NNRTI binding pocket residues.

TABLE 4

| Isolate | 33 | 26 | TZB | TIBO |
| --- | --- | --- | --- | --- |
| NL4-3 (WT) | 0.5 | 1.85 | 1.7 | 0.3 |
| L74V | 0.1 | 0.46 | 0.7 | 0.2 |
| A98G | 1.4 | 4.75 | 17.7 | 11 |
| L1001 | 0.3 | 1.36 | 12.2 | 17.4 |

TABLE 4-continued

| Isolate | 33 | 26 | TZB | TIBO |
|---|---|---|---|---|
| K101E | 16.7 | >20 | >20 | 17.4 |
| K103N | 8.1 | 12.9 | >20 | 17.4 |
| V106A | 20 | >20 | >20 | 12.5 |
| V108I | 2.8 | 10.4 | 9.7 | 2.4 |
| V179D | 0.5 | 2.3 | 3.1 | 6.2 |
| Y181C | 6 | 15.2 | 16.3 | 4.2 |
| Y188C | 2.3 | 11.7 | >20 | >17.4 |
| 4xAZT | 0.1 | 0.27 | 1.5 | 0.3 |
| 4xAZT/L1001 | 0.2 | 0.84 | 1.7 | >17.4 |
| 4xAZT/Y181C | 3.5 | >20 | 14.5 | 2.0 |

TABLE 8

Cross Resistance Profile of 4-Substituted 1-(2,6-difluorobenzyl)-2-(2,6-difluorophenyl)benzimidazoles in Cytopathic Cell Killing Assay

| Isolate | $CH_3$ | $OCH_3$ | Et | Cl | $NH_3$ | NHAc | $NAcCH_3$ | $NHCH_3$ | nevir. | TZB |
|---|---|---|---|---|---|---|---|---|---|---|
| NL4-3 | 0.5 | 0.06 | 1.1 | 0.4 | 0.5 | 1.6 | 0.04 | 2.6 | 0.04 | 1.0 |
| L74V | 0.3 | 0.08 | 1.5 | 0.5 | 0.3 | 1.2 | 0.07 | 3.9 | 0.04 | 0.8 |
| A98G | 2.3 | 0.3 | 8.0 | 5.0 | 1.5 | 4.3 | 0.1 | 8.5 | 0.8 | 10 |
| L1001 | 0.3 | 0.1 | 0.6 | 0.2 | 1.3 | 2.1 | 1.7 | 0.4 | 0.2 | 6.6 |
| K101E | >10 | 3.3 | >20 | >20 | >20 | >20 | 0.6 | >20 | 1.1 | >10 |
| K103N | >20 | >20 | >20 | >20 | >20 | >20 | >10 | >20 | >10 | >20 |
| V106A | >10 | 1.4 | >20 | >10 | >20 | >20 | 0.05 | >20 | >10 | >10 |
| V108I | 2.8 | 2.5 | 3.0 | 3.6 | >20 | 5.3 | >10 | >20 | 0.4 | 5.7 |
| V179D | 0.7 | 0.2 | 1.8 | 0.8 | 0.3 | 1.7 | 0.1 | 3.8 | 0.2 | 3.9 |
| Y181C | 4.3 | 0.3 | >10 | 7.3 | 6.0 | >10 | 0.4 | >10 | 4.9 | >10 |
| Y188C | 3.0 | 0.3 | 5.5 | 5.4 | 2.7 | >10 | 0.5 | >20 | >0.5 | >20 |
| 4XAZT | 0.1 | 0.6 | 3.0 | 0.2 | 0.2 | | >10 | >10 | >0.5 | 1.1 |
| 4XAZT/L1001 | 0.2 | | 0.6 | 0.2 | 0.3 | | 1.8 | 1.0 | 0.1 | 1.1 |
| 4XAZT/Y181C | 3.5 | | >20 | >20 | >10 | | >10 | >20 | 3.0 | >10 |

TABLE 9

Cross Resistance Profile of 4-Substituted 1-(2,6-difluorobenzyl)-2-(2,6-difluorophenyl)benzimidazoles in Cytopathic Cell Killing Assay

| Isolate | (X = $CH_3$) R = 2,6-F,Bn | (X = H) R = 2,6-F,Bn | (X = $CH_3$) R = prenyl | TIBO | nevir. | TZB |
|---|---|---|---|---|---|---|
| NL4-3 | 0.5 | 2.2 | 1.3 | 0.3 | 0.04 | 1.0 |
| L74V | 0.3 | 1.9 | | 0.2 | 0.04 | 0.8 |
| A98G | 2.7 | 4.7 | | 11 | 0.8 | 10 |
| L1001 | 0.3 | 1.3 | 0.3 | >10 | 0.2 | 6.6 |
| K101E | >10 | >20 | >20 | >10 | 1.1 | >10 |
| K103N | >20 | >10 | >20 | >10 | >10 | >20 |
| V106A | >10 | >20 | | >10 | >10 | >10 |
| V108I | 2.8 | >10 | >20 | 2.4 | 0.4 | 5.7 |
| V179D | 0.7 | 2.9 | | 6.2 | 0.2 | 3.9 |
| Y181C | 4.3 | 14 | >20 | 4.2 | 4.9 | >10 |
| Y188C | 3.0 | >10 | | >20 | >0.5 | >20 |
| 4XAZT | 0.1 | 0.3 | | 0.3 | >0.5 | 1.1 |
| 4XAZT/L1001 | 0.2 | 0.9 | | >20 | 0.1 | 1.1 |
| 4XAZT/Y181C | 3.5 | >20 | | 2 | 3.0 | >10 |

TABLE 10

Cross Resistance Profile of 1,2-substituted Benzimidazoles Based on Cytopathic Cell Killing Assay (values in $\mu M$).

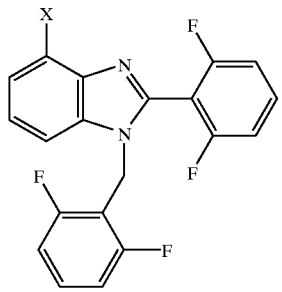

| Isolate | $CH_3$ | $OCH_3$ | Cl | Br | NHAc | $N(CH3)_2$ | $NH_2$ | $NH_2$ | $NO_2$ | Et | TIBO | $CH_2$—$N_3$ |
|---|---|---|---|---|---|---|---|---|---|---|---|---|
| NL4-3 (WT) | 0.5 | 0.165 | 0.5 | 0.5 | 1.97 | 2.88 | 0.68 | 0.4 | 3.13 | 0.9 | 0.3 | 0.045 |
| L100I | 0.3 | 0.16 | 0.3 | 0.5 | 3.25 | 31.6 | 2.46 | 1.2 | 0.83 | 2.48 | 17.4 | 0.06 |
| K101E | 16.7 | 2.82 | >20 | >20 | | | >50 | >20 | >50 | >50 | 17.4 | 0.60 |
| K103N | 8.1 | >50 | 10.2 | >20 | >100 | | >50 | 3.1 | >50 | >50 | 17.4 | 1.48 |
| V108I | 2.8 | 2.82 | 3.2 | 4.2 | | | >50 | 3.3 | >50 | >50 | 2.4 | 0.026 |
| Y181C | 6 | 0.26 | 8.4 | 10.7 | >100 | >100 | 3.99 | 9.2 | >50 | 7.18 | 4.2 | 0.82 |
| M184I | | 0.16 | | | | | | 0.65 | | 3.69 | 0.96 | |
| Y188H | | 0.26 | | | | | >50 | | >50 | 13.2 | | |
| Y188C | 2.3 | | 3.4 | 3.7 | | | | 2 | | | >17.4 | 0.22 |

Table 8 and 10 show the cross-resistance profile with NNRTI-resistant HIV isolates from the cytopathic cell killing assay for a number of 4-substituted compounds (the methyl, methoxyl, ethyl, chloro, bromo, amino, N-acetamido, N-methylacetamido, N-methylamino and N-dimethylamino derivatives, nitro and methylazido), as well as, TZB and nevirapine. The methoxyl, N-methyl acetamido, ethyl, chloro, amino, N-acetamido, and N-methyl amino derivatives were all found to inhibit HIV-1 better than TZB in the cytopathic cell killing assay. In the case of the methoxyl and N-methylacetamido derivative the cross-resistance profile was equal or better against the various variants than nevirapine, the only nonnucleoside inhibitor currently approved by the FDA for the treatment of AIDS. The only variant that showed no inhibition for the different compounds tested was the K103N isolate which also renders TZB and nevirapine ineffective.

Table 9 shows the effect of substitution of the N-1 position on the ability to inhibit some NNRTI-resistant HIV isolates. Substitution of the 2,6-difluorobenzyl group by the prenyl side chain found in TIBO was seen to decrease the inhibitory activity for the V108I and Y181C variants.

Figure 10:
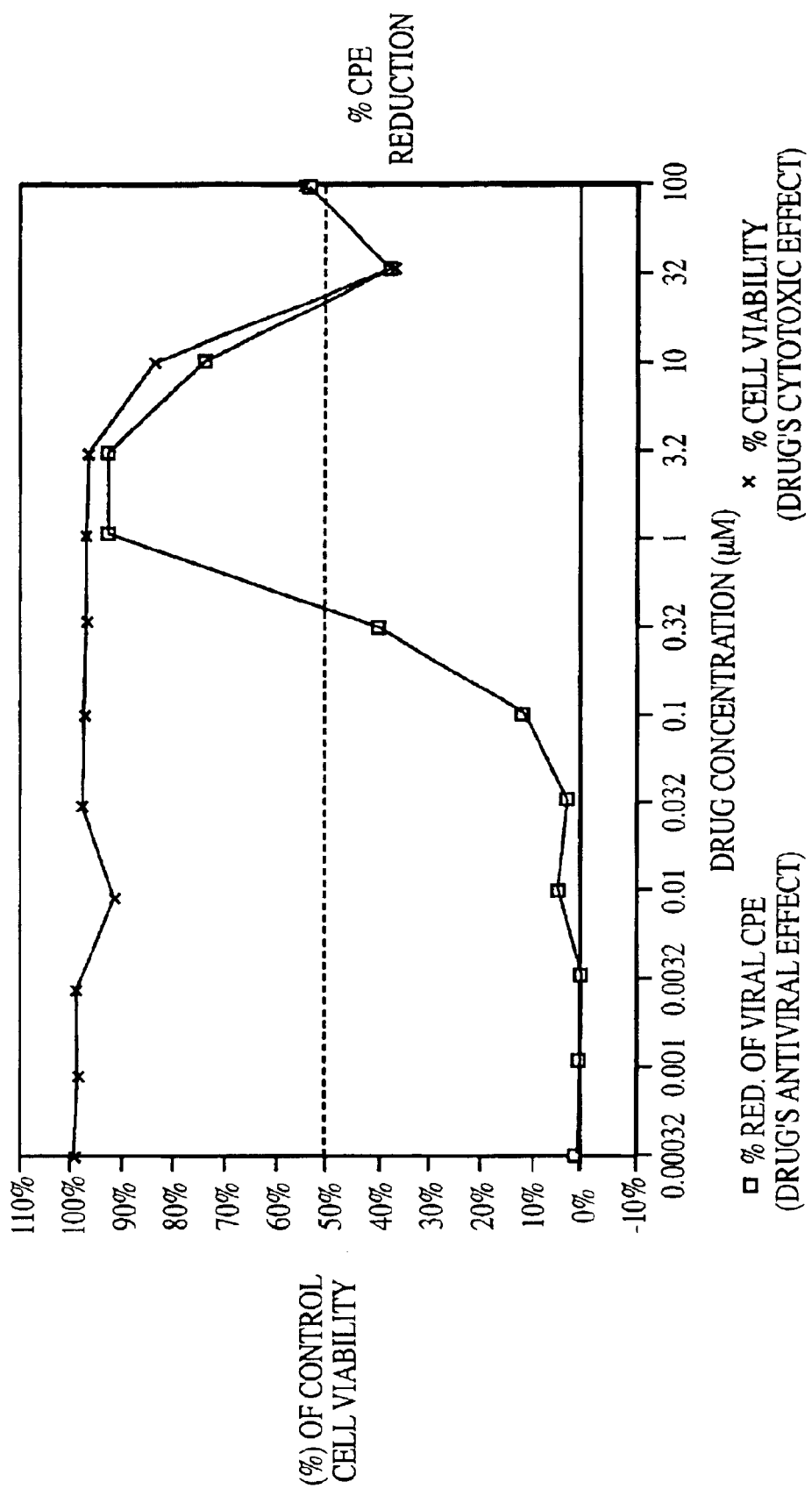
FIG. 10 is a summary graph showing the cytotoxicity and anti-viral effect of compound 33.
Figure 11:
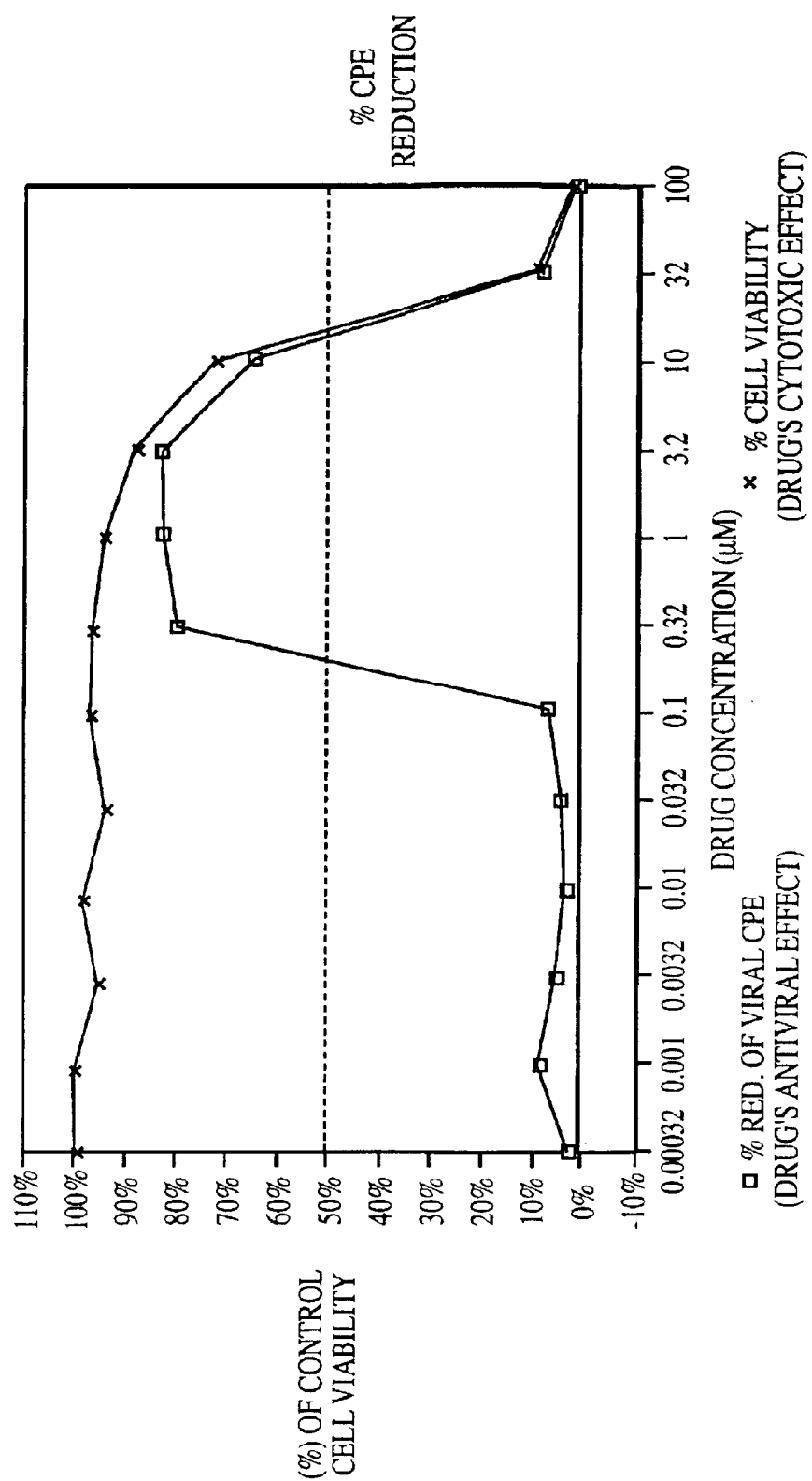
FIG. 11 is a summary graph showing the cytotoxicity and anti-viral effect of compound 34.
Figure 12:
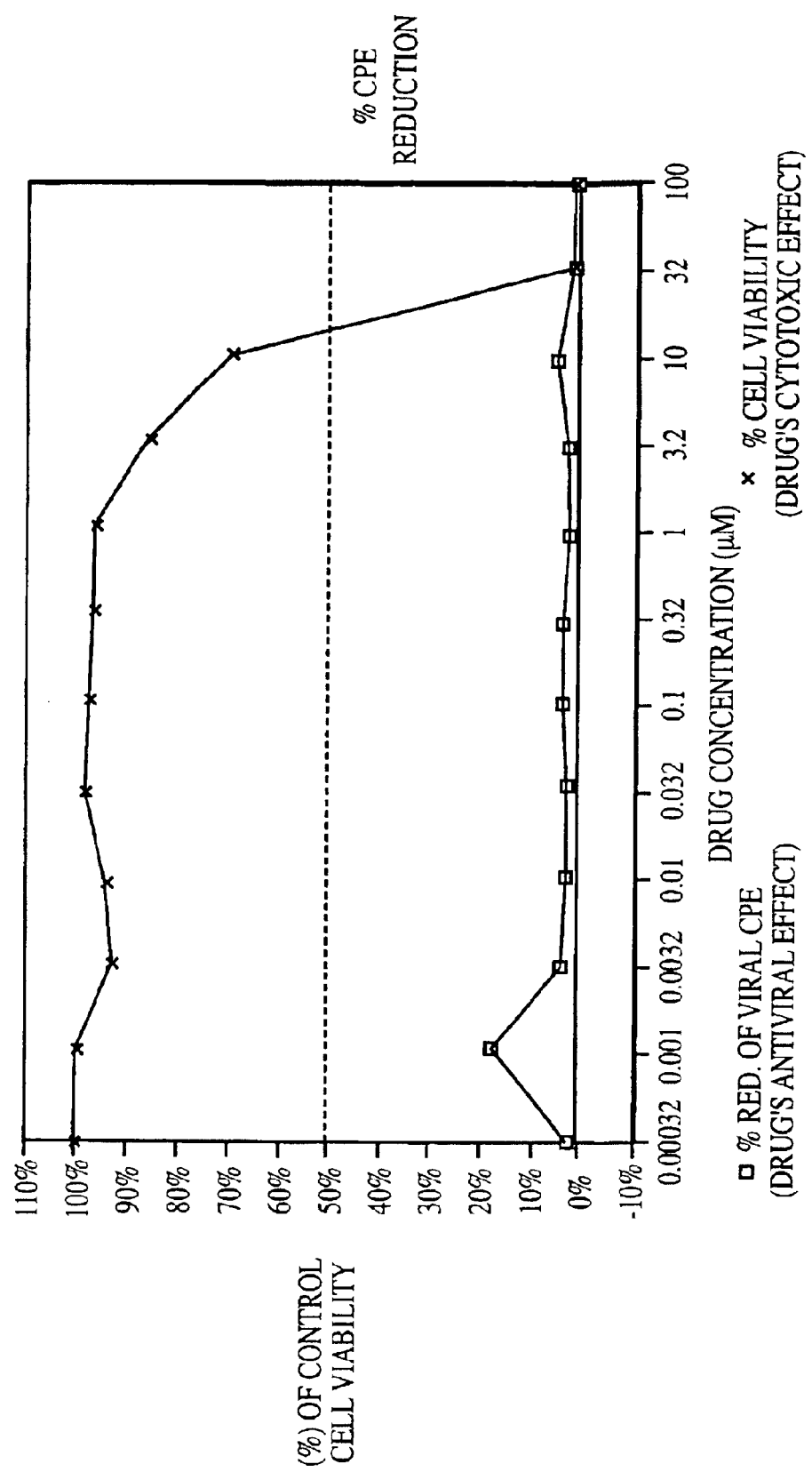
FIG. 12 is a summary graph showing the anti-viral results for inactive compound 2100.

FIGS. 10–12 indicate the therapeutic index for three embodiments of the present invention. The therapeutic index is the difference between efficacy of the drug and cellular toxicity. In the case of 4-methyl derivative (33), the therapeutic index at 50% ($TC_{50}$) was greater than one log in concentration.

In summary, the methoxyl and N-methylacetamido compounds were found to possess the best overall biological profile of this series. These two embodiments were determined to inhibit many of the known clinically relevant non-nucleoside amino acid variants of HIV-1. It is contemplated that other substitutions or different attachment sites may result in further optimization of the compounds of the present invention. The present invention provides significant advantages over drugs such as TZB and nevirapine, as the compositions provided herein retain activity against HIV mutants that have lost sensitivity to these drugs (e.g., the V106A, Y181C, and Y188C isolates).

IV. Geometry Of TBZ And 1-(2,6-Difluorobenzyl)-2-Phenylbenzimidazole

Figure 5:
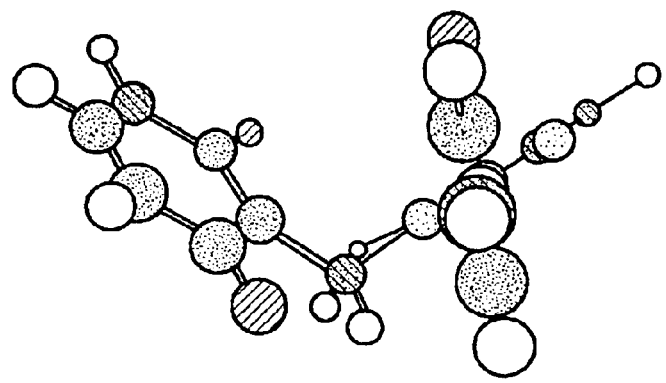
FIG. 5 shows the "butterfly-like" shape of TBZ and 39.
Figure 5:
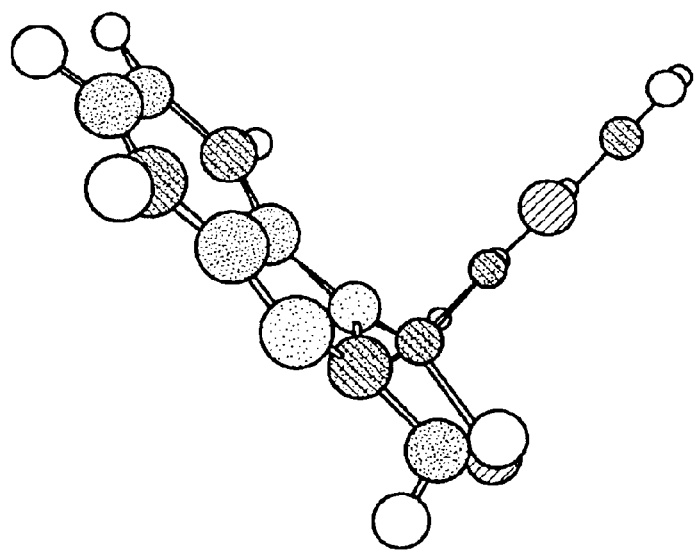

Semi-empirical quantum mechanical minimization at the AM1 level was used to compare the geometry of TBZ and 1-(2,6-difluorobenzyl)-2-phenylbenzimidazole (39). As shown in FIG. 5, considerable similarity was observed between the energy minimized "butterfly-like" shapes of TBZ and 39. For TBZ, the "butterfly-like" shape was previously determined by x-ray and NMR methods. (See, A. Chimirri et al., "Thiazobenzimidazoles as Non-Nucleoside HIV-1 RT Inhibitors," Abst. II Congresso Congiunto Italiano-Spagnolo di Chimica farmaceutica," Ferrara, Italy, Aug. 30–Sep. 3, 1995, ML20). For 39 in contrast to TBZ, more than one "butterfly-like" conformation can be adopted by rotation of the molecule's benzyl side chain. Although the C2 phenyl of the AM1 energy-minimized molecule 39 does not overlap the thiazolo ring of TBZ, at least two higher energy rotational isomers result in almost complete overlap. Although x-ray analysis is required to predict the correct "butterfly-like" orientation of this compound with RT and the NNRTI binding pocket, since some of the predominant contributions to the binding of NNRTI to RT involve $\pi$ stacking and hydrophobic interactions. The extra aromatic ring present in 39 might significantly influence these interactions. This ability of HIV-1 RT to accommodate extra phenyl rings resulted in investigation of additional aromatic moieties.

V. Purity Of The Substituted Benzimidazoles

The active benzimidazole compounds of the present invention were produced at a very high purity level. As shown in Table 12, the carbon, hydrogen and nitrogen analyses (CHN values) of these compounds were very close to the predicted values. CHN analysis (i.e., elemental analysis) as known to those in the art, determines the amount of the elements in accurately weighed samples of the compound, and matches them against the amounts predicted from the elemental formulae. Correspondence of experimental with the predicted values to within 0.3% indicates high levels of purity. Thus, it is clear that the substituted benzimidazoles of the present invention may be produced at very high purity levels.

TABLE 12

| No | formula | calculated | | | found | | |
|---|---|---|---|---|---|---|---|
| | | C | H | N | C | H | N |
| 26 | $C_{20}H_{12}F_4N_2$ | 67.42 | 3.39 | 7.86 | 67.28 | 3.44 | 7.76 |
| 28 | $C_{20}H_{12}F_2N_2 \times 1/8H_2O$ | 74.47 | 4.45 | 8.68 | 74.43 | 4.45 | 8.63 |
| 29 | $C_{21}H_{16}F_2N_2 \times 1/4H_2O$ | 74.43 | 4.91 | 8.27 | 74.81 | 4.90 | 7.85 |
| 30 | $C_{21}H_{14}Cl_2F_2N_2 \times 1/4H_2O$ | 61.86 | 3.58 | 6.87 | 61.64 | 3.65 | 6.80 |
| 32 | $C_{22}H_{16}F_4N_2O \times 1/2H_2O$ | 64.55 | 4.19 | 6.84 | 64.63 | 4.11 | 6.72 |
| 33 | $C_{21}H_{14}F_4N_2$ | 68.11 | 3.81 | 7.56 | 68.17 | 3.90 | 7.54 |
| 34 | $C_{18}H_{18}F_2N_2$ | 71.98 | 6.04 | 9.33 | 72.06 | 6.05 | 9.25 |
| 35 | $C_{15}H_{12}F_2N_2$ | 69.76 | 4.68 | 10.85 | 69.56 | 4.77 | 10.79 |
| 36 | $C_{21}H_{16}F_2N_2$ | 75.44 | 4.82 | 8.38 | 75.16 | 4.89 | 8.29 |
| 37 | $C_{25}H_{18}F_2N_2$ | 78.11 | 4.72 | 7.29 | 78.00 | 4.75 | 7.19 |
| 38 | $C_{25}H_{18}F_2N_2$ | 78.11 | 4.72 | 7.29 | 77.84 | 4.83 | 7.23 |
| 39 | $C_{20}H_{14}F_2N_2 \times 1/4H_2O$ | 73.95 | 4.50 | 8.62 | 73.87 | 4.50 | 8.60 |
| 40 | $C_{20}H_{15}F_2N_3$ | 71.63 | 4.51 | 12.53 | 71.74 | 4.55 | 12.62 |
| 41 | $C_{20}H_{15}F_2N_3$ | 71.63 | 4.51 | 12.53 | 71.72 | 4.55 | 12.58 |
| 42 | $C_{21}H_{11}F_7N_2$ | 59.44 | 2.61 | 6.60 | 59.35 | 2.65 | 6.50 |
| 43 | $C_{20}H_{15}F_2N_3 \times 1/2H_2O$ | 69.76 | 4.68 | 12.20 | 69.59 | 4.38 | 12.29 |
| 45 | $C_{19}H_{12}F_2N_2SO_2$ | 61.62 | 3.27 | 7.56 | 61.68 | 3.34 | 7.60 |
| 46 | $C_{20}H_{14}F_2N_2SO_2$ | 62.49 | 3.67 | 7.29 | 62.50 | 3.71 | 7.24 |
| 47 | $C_{20}H_{10}F_4N_2O$ | 64.87 | 2.72 | 7.56 | 64.88 | 2.77 | 7.46 |
| 48 | $C_{16}H_{14}F_2N_2O$ | 66.66 | 4.89 | 9.72 | 66.74 | 4.94 | 9.71 |
| 49 | $C_{15}H_{12}F_2N_2 \times 1/4H_2O$ | 68.56 | 4.79 | 10.66 | 68.52 | 4.60 | 10.7 |
| 50 | $C_{16}H_{12}F_2N_2O \times 1/5H_2O$ | 66.29 | 4.31 | 9.66 | 66.57 | 4.28 | 9.67 |
| 3100 | $C_{20}H_{13}F_4N_3$ | 64.69 | 3.53 | 11.32 | 64.63 | 3.54 | 11.20 |
| 3400 | $C_{22}H_{15}F_4N_3O$ | 63.92 | 3.66 | 10.17 | 63.94 | 3.62 | 10.10 |
| 3500 | $C_{22}H_{17}F_4N_3$ | 66.16 | 4.29 | 10.52 | 66.24 | 4.24 | 10.47 |
| 3200 | $C_{20}H_{11}BrF_4N_2 \times 1/4H_2O$ | 54.63 | 2.64 | 6.37 | 54.59 | 2.47 | 6.38 |
| 1800 | $C_{20}H_{11}BrF_4N_2 \times 3/4H_2O$ | 53.53 | 2.81 | 6.24 | 53.23 | 2.49 | 6.10 |
| 3300 | $C_{20}H_{11}ClF_4N_2$ | 61.47 | 2.84 | 7.17 | 61.59 | 2.86 | 7.23 |
| 2000 | $C_{20}H_{11}ClF_4N_2$ | 61.47 | 2.84 | 7.17 | 61.37 | 2.90 | 7.15 |
| 2100 | $C_{20}H_{11}ClF_4N_2$ | 61.47 | 2.84 | 7.17 | 61.31 | 2.92 | 7.04 |
| 2200 | $C_{21}H_{14}F_4N_2$ | 68.11 | 3.81 | 7.56 | 68.22 | 3.90 | 7.60 |
| 2300 | $C_{21}H_{14}F_4N_2$ | 68.11 | 3.81 | 7.56 | 67.94 | 3.86 | 7.50 |
| 2400 | $C_{21}H_{14}F_4N_2$ | 68.11 | 3.81 | 7.56 | 68.02 | 3.89 | 7.49 |
| 2800 | $C_{22}H_{16}F_4N_2$ | 68.75 | 4.20 | 7.29 | 68.68 | 4.15 | 7.28 |
| 2900 | $C_{20}H_{11}F_4N_3O_2$ | 59.86 | 2.76 | 10.47 | 59.96 | 2.78 | 10.55 |
| 3000 | $C_{20}H_{11}F_4N_3O_2$ | 59.86 | 2.76 | 10.47 | 60.24 | 2.89 | 10.38 |

Experimental

The following examples are provided in order to demonstrate and further illustrate certain preferred embodiments and aspects of the present invention and are not to be construed as limiting the scope thereof. Although embodiments have been described with some particularity, many modifications and variations of the preferred embodiment are possible without deviating from the invention.

In the experimental disclosure which follows, the following abbreviations apply: PBS (phosphate buffered saline); MTT (3-(4,5-dimethylthiazol-2-yl)-2,5-diphenyl-tetrazolium bromide); EDTA (ethylenedinitrotetraacetic acid disodium salt); HCl (hydrogen chloride); Tris (triphenylphosphine); NaCl (sodium chloride); SDS (sodium dodecyl sulfate); $Na_2S_2O_3$ (sodium thiosulfate); TAE (Tris-Acetate-EDTA); $MeOH/Cl_2Cl_2$ (methanol/dichloromethane); $H_2SO_4$ (sulfuric acid); $FeSO_4$ (ferrous sulfate); $CuSO_4$ (cuprous sulfate); $MgSO_4$ (magnesium sulfate); NaOAc (sodium acetate); DMF (dimethyl formamide); THF (tetrahydrofaran); $NaHCO_3$ (sodium bicarbonate); HBr (hydrogen bromide); KBr (potassium bromide); DMSO (dimethyl sulfoxide); DMSO-$d_6$ (fully deuterated dimethyl sulfoxide); $CHCl_3$ (chloroform); $CDCl_3$ (deuterated chloroform); $NH_3$ (ammonia); Ph (phenyl; $C_6H_5$) Ac (ethanoate group); $Et_2O$ (diethyl ether); EtOAc (ethyl acetate); CPE (cytopathic effect); ppm (parts per million); [α] (specific rotation); μL (microliters); μg (micrograms); mL (milliliters); L (liters); mg (milligrams); g (grams); hr or h (hours); mM (millimolar); M % (mole percent); μM (micromolar); nM (nanomolar); N (normal); nm (nanometers); min (minutes); mm (millimeter); kg (kilograms); δ (chemical shift); J or J (coupling constant); s (singlet); d (doublet); t (triplet); q (quartet); m (multiplet); vs (very strong); s (strong); m (medium); w (weak); vw (very weak); v (variable); mp (melting point); c (optical path length); NMR (Nuclear Magnetic Resonance); IR (Infrared Spectroscopy); MHz (megahertz); Hz (hertz); cm$^{-1}$ (wavenumbers); eq (equivalents); M (Molar); μM (micromolar); N (Normal); mol (moles); mmol (millimoles); μmol (micromoles); nmol (nanomoles); g (grams); mg (milligrams); μg (micrograms); ng (nanograms); 1 or L (liters); ml (milliliters); μl (microliters); cm (centimeters); mm (millimeters); μm (micrometers); nm (nanometers); ° C. (degrees Centigrade); Ci (Curies); mCi (milliCuries); mp (melting point); TBZ (1-(2,6-difluorophenyl)-1H,3H-thiazolo[3,4-a]benzimidazole; RT (reverse transcriptase); WT (wild type); AZT (3'-azido-3'-deoxythymidine); NNRT (non-nucleoside reverse transcriptase); NNRTI (non-nucleoside reverse transcriptase inhibitors); BSA (bovine serum albumin); Et (ethyl); CHAPS (3-[(3-cholamidopropyl)dimethylammonio]-1-propane-sulfonate); ddC (2',3'-dideoxycytidine); TIBO (4,5,6,7-tetrahydro-5-methylimidazo[4,5,1-jk][1,4]benzodiazepin-2(1H)-one; THF (tetrahydrofuran); t-(tert);BDMSCl (t-butyldimethylsilylchloride); TBDMS (t-butyldimethylsilyl); IC$_{50}$ (inhibitory concentration, 50%); EC$_{50}$ (median effective concentration); Varian (Varian Analytical Instruments, San Fernando, Calif.); Sigma (Sigma Chemical Co., St. Louis, Mo.); and (Aldrich Chemical Company, Inc., Milwaukee, Wis.).

Unless otherwise indicated, all chemicals and reagents were obtained from commercially available sources, such as Sigma and Aldrich. Where analyses are indicated by symbols of the elements, the observed results were within 0.4% of the theoretical values. Melting points were determined on an electrothermal apparatus using the supplied, stem-corrected thermometer and read, per methods known in the art. NMR spectra were recorded on a Varian 200 or 300 MHz spectrometer, with Me$_4$Si as the internal standard. Merck silica gel (70–230 mesh and 230–400 mesh) were used for gravity and flash chromatography, respectively. Primes used in NMR assignments are defined by R' and R" in the structures shown in FIG. 3.

Examples 1–4 show the preparation of 2-hydroxymethyl benzimidazole derivatives with reagent and other substitutions as indicated.

EXAMPLE 1

Preparation of 2-Hydroxymethylbenzimidazole

In this Example, 2-hydroxymethylbenzimidazole (2) was prepared by stirring o-phenylenediamine (1) (1.3 g, 12 mmol), and 85% glycolic acid (2.74 g, 36 mmol, 300 M %), in 4 N HCl (40 mL), under reflux for 4 hours. After cooling to room temperature, the pH was adjusted to 7, with NaOH. The resulting crystals were filtered, washed with water and dried in vacuo (0.71 g, 4.8 mmol, 40% yield). $^1$H-NMR (300 MHz, DMSO-$d_6$): δ 7.48 (m, 2H, H$_{4,7}$), 7.13 (m, 2H, H$_{5,6}$), 5.67 (t, J=5.5 Hz, 1H, OH), 4.68 (d, J=5.5 Hz, 2H, CH$_2$).

EXAMPLE 2

Preparation of 2-Hydroxymethyl-4-Methylbenzimidazole

In this Example, 2-hydroxymethyl-4-methylbenzimidazole (4) was prepared by stirring 2,3-diaminotoluene (3) (2.65 g 21.7 mmol), and 85% glycolic acid (8.20 g, 107.8 mmol, 500 M %) in 4 N HCl (80 mL), under reflux for 2 hours. After cooling to room temperature, the pH was adjusted to 7 with NaOH. The resulting brown precipitate was filtered, washed with water, and dried in vacuo (2.97 g, 18.3 mmol, 84% yield). $^1$H-NMR (200 MHz, DMSO-$d_6$): δ 7.28 (br d, 1H, $H_7$), 6.98 (dd, J=8.0, 7.3 Hz, 1H, $H_6$), 6.90 (m, 1H, $H_5$), 4.67 (s, 2H, $CH_2$), 2.49 (s, 3H, $CH_3$).

EXAMPLE 3

Preparation of 2-(t-Butyldimethylsilyloxymethyl)-4-Methylbenzimidazole

In this Example, 2-(t-Butyldimethylsilyloxymethyl)-4-Methylbenzimidazole (5) was prepared by dissolving 2-hydroxymethyl-4-methylbenzimidazole (4) (1.50 g, 9.24 mmol) in pyridine (30 mL). To this mixture, t-BDMSCl (2.35 g, 15.6 mmol, 170 M %) was added. After 4 hours at room temperature, the reaction was concentrated to dryness. The residue was redissolved in $CH_2Cl_2$, and washed with $NaHCO_3$ (sat. aq.), and NaCl (sat. aq.). The combined washings were dried with $Na_2SO_4$, filtered and concentrated. The crude product was purified by flash chromatography eluting with 4% MeOH/$CH_2Cl_2$, and then re-crystallized from hexane (2.15 g, 7.78 mmol, 84% yield), yielding white powders of 2-(t-Butyldimethylsilyloxymethyl)-4-methylbenzimidazole. $^1$H-NMR (300 MHz, $CD_3OD$): δ 7.36 (br d, J=11.1 Hz, 1H, $H_7$), 7.11 (dd, J=11.1, 10.4 Hz, 1H, $H_6$), 7.01 (br d, J=10.4 Hz, 1H, $H_5$), 4.94 (s, 2H, $CH_2O$), 2.55 (s, 3H, $CH_3$), 0.95 (s, 9H, Sit-Bu), 0.14 (s, 6H, Si($CH_3$)$_2$).

EXAMPLE 4

Preparation of 2-Isopropyl-4-Methylbenzimidazole

In this Example, 2-isopropyl-4-methylbenzimidazole (6) was prepared by dissolving 2,3-diaminotoluene (3) (1.00 g, 8.19 mmol), and isobutyric acid (4.0 mL, 43.1 mmol, 525 M %), in 4 N HCl (90 mL). After 2 hours at reflux, the reaction was cooled in an ice bath, and the pH adjusted to 7 with NaOH. The resulting precipitate was filtered and washed with water. $^1$H-NMR (200 MHz, DMSO-$d_6$): δ 12.02 (br, 1H, NH), 7.26 (br, 1H, $H_7$), 6.99 (dd, J=7.4, 7.7 Hz, 1H, $H_6$), 6.87 (ddt, J=0.8, 1.1, 7.4 Hz, 1H, $H_5$), 3.14 (sep, J=7.0 Hz, 1H, iPr), 2.48 (s, 3H, $CH_3$), 1.34 (d, J=7.0 Hz, 6H, iPr).

EXAMPLE 5

Preparation of N-(2,6-Difluorobenzoyl)-2-Nitroanilide

In this Example, N-(2,6-difluorobenzoyl)-2-nitroanilide (10) was prepared using "Method A." First, 2-nitroaniline (8) (1.1 g, 8.0 mmol) was dissolved in THF (10 mL) and pyridine (2 mL). Then, 2,6-difluorobenzoyl chloride (1.11 mL, 8.8 mmol, 110 M %) dissolved in THF (15 mL) was added to the first mixture. After stirring for 5 hours at room temperature, the reaction was concentrated to dryness. The residue was redissolved in ethylacetate, and washed with $NaHSO_4$ (5% solution), $NaHCO_3$ (sat. aq.), and NaCl (sat. aq.). The organic layer was dried under $Na_2SO_4$, filtered, and concentrated under reduced pressure. The residue was recrystallized from ethylacetate/hexane, to produce crystals that were slightly yellow (1.7 g, 6.1 mmol, 76%). M.p. 139° C. $^1$H-NMR (300 MHz, $CD_2Cl_2$): δ 10.77 (s, 1H, NH), 8.89 (dd, J=1.2, 8.5 Hz, 1H, $H_3$), 8.26 (dd, J=1.5, 8.5 Hz, 1H, $H_6$), 7.75 (ddd, J=1.2, 7.9, 8.5 Hz, 1H, $H_5$), 7.50 (m, 1H, $H_4$), 7.29 (ddd, J=1.5, 7.9, 8.5 Hz, 1H, $H_4$), 7.07 (m, 2H, $H_{3',5'}$).

EXAMPLE 6

Preparation of N-(2,6-Difluorobenzoyl)-2-Methyl-6-Nitroanilide

In this Example, N-(2,6-difluorobenzoyl)-2-methyl-6-nitroanilide (11) was prepared using Method A. 2-methyl-6-nitroaniline (9) (2.25 g, 14.8 mmol) and 2,6-difluorobenzoyl chloride (7) (1.9 mL, 15 mmol, 100 M %) were mixed and stirred overnight. The solution was purified by gravity chromatography, and eluted with $CH_2Cl_2$/hexane/diethylether (380-120-10), yielding slightly yellow crystals of N-(2,6-difluorobenzoyl)-2-methyl-6-nitroanilide (2.36 g, 8.1 mmol, 55% yield). $^1$H-NMR (300 MHz, $CD_2Cl_2$): δ 8.55 (s, 1H, NH), 7.87 (dd, J=8.2, 0.92 Hz, 1H, $H_5$), 7.61 (d, J=7.4 Hz, 1H, $H_3$), 7.48 (m, 1H, $H_4$), 7.38 (dd, J=7.4, 8.2 Hz, 1H, $H_4$) 7.05 (m, 2H, $H_{3',5'}$), 2.43 (s, 3H, $CH_3$).

EXAMPLE 7

Preparation of N-isonicotinoyl-2-Methyl-6-Nitroanilide

In this Example, N-isonicotinoyl-2-methyl-6-nitroanilide (12) was prepared using Method A. 2-methyl-6-nitroaniline (9) (1.52 g, 10.0 mmol), and isonicotinoyl chloride hydrochloride (2.95 g, 19.7 mmol, 200 M %) were stirred together for 4 hours. A second addition of isonicotinoyl chloride hydrochloride (1.05 g, 5.90 mmol, 60 M %) was added, and the solution was stirred overnight. The preparation was re-crystallized from diethylether/hexane (3:1), to produce 1.61 g (6.26 mmol, 53% yield) of white powder. $^1$H-NMR (300 MHz, $CD_2Cl_2$): δ 9.06 (br, 1H, NH), 8.82 (m, 2H, $H_{2',6'}$) 7.93 (br d, 7.9 Hz, 1H, $H_6$), 7.77 (m, 2H, $H_{3',5'}$), 7.63 (br d, J=8.0 Hz, 1H, $H_3$), 7.40 (dd, J=7.9, 8.0 Hz, 1H, $H_4$).

EXAMPLE 8

Preparation of N-(2-Methylbenzoyl)-2-Nitroanilide

In This Example, N-(2-methylbenzoyl)-2-nitroanilide (13) was prepared by Method A, by mixing 2-nitroaniline (8) (1.28 g, 9.3 mmol) and o-toluoyl chloride (1.52 mL, 11.6 mmol, 125 M %). Recrystallization of the crude product from ether/hexane (1:1) produced yellow crystals of N-(2-methylbenzoyl)-2-nitroanilide (2.2 g, 8.6 mmol, 92% yield). $^1$H-NMR (300 MHz, $CD_2Cl_2$): δ 10.75 (s, 1H, NH), 8.98 (d, J=8.5 Hz, 1H, $H_3$), 8.27 (d, J=8.5 Hz, 1H, $H_6$), 7.72 (dd, J=8.5, 7.4 Hz, 1H, $H_5$), 7.61 (d, J=8.4 Hz, 1H, $H_6$), 7.41 (dd, J=8.5, 7.4 Hz, 1H, $H_4$), 7.32 (t, J=7.4 Hz, 1H, $H_4$), 7.31 (d, J=7.4 Hz, 1H, $H_3$), 7.23 (dd, J=8.4, 7.4 Hz, 1H, $H_5$), 2.56 (s, 3H, $CH_3$).

EXAMPLE 9

Preparation of N-(1-Naphthoyl)-2-Methyl-6-Nitroanilide

In this Example, N-(1-naphthoyl)-2-methyl-6-nitroanilide was prepared by Method A, by mixing 2-methyl-6-nitroaniline (9) (1.52 g, 10.0 mmol) and 1-naphthoyl chloride (2.00 mL, 13.3 mmol, 130 M %). After one hour of stirring at room temp, a second volume of 1-naphthoyl chloride (1.0 mL, 6.65 mmol, 66 M %) was added. The mixture was stirred for 6 hours. The crude product was recrystallized from ethyl acetate, yielding white powders of N-(1-naphthoyl)-2-methyl-6-nitroanilide (2.79 g, 9.11 mmol, 91% yield). $^1$H-NMR (200 MHz, $CD_2Cl_2$): δ 8.09–7.99 (m, 2H), 7.77 (m, (m, 1H), 7.66–7.41 (m, 5H), 7.23 (d, J=8.3 Hz, 1H), 7.24 (dd, J=7.3 Hz, 1H), 2.77 (s, 3H, $CH_3$).

EXAMPLE 10

Preparation of N-(2-Naphthoyl)-2-Methyl-6-Nitroanilide

In this Example, N-(2-naphthoyl)-2-methyl-6-nitroanilide was prepared according to Method A, by mixing 2-methyl-6-nitroaniline (9)(1.52 g, 10.0 mmol) and 2-naphthoyl chloride (2.00 mL, 13.3 mmol, 130 M %). After 1 hour of stirring, a second volume of 2-naphthoyl chloride (1.0 mL, 6.65 mmol, 66 M %) was added. The mixture was stirred for 6 hours. The crude product was recrystallized from methyl acetate to produce white powders of N-(2-Naphthoyl)-2-Methyl-6-Nitroanilide (2.29 g, 7.48 mmol, 75% yield). $^1$H-NMR (300 MHz, $CD_2Cl_2$): δ 9.15 (br s, 1H, NH), 8.49 (s, 1H, $H_1$), 8.06–7.86 (m, 5H, nap & $H_5$), 7.72–7.45 (m, 3H, nap & $H_3$),7.37 (dd, J=7.73 Hz, 1H, $H_4$), 2.43 (s, 3H, $CH_3$).

EXAMPLE 11

Preparation of N-Nicotinoyl-2-Methyl-6-Nitroanilide

In this Example, N-Nicotinoyl-2-methyl-6-nitroanilide (16) was prepared by Method A, by mixing 2-methyl-6-nitroaniline (9) (1.52 g, 10.0 mmol) and nicotinoyl chloride hydrochloride (2.67 g, 15.0 mmol, 150 M %), and stirring the reaction overnight. Recrystallization of the crude product from diethylether/hexane (3:1) yielded N-nicotinyl-2-methyl-6-nitroanilide (1.41 g, 5.49 mmol, 55% yield). $^1$H-NMR (300 MHz, $CD_2Cl_2$): δ 9.16 (dd, J=0.8, 2.2 Hz, 1H, $H_2$), 9.01 (br, 1H, NH), 8.80 (dd, J=1.7, 4.8 Hz, 1H, $H_6$), 8.23 (ddd, J=1.7, 2.2, 8.0 Hz, 1H, $H_4$), 7.92 (m, 1H, $H_5$), 7.62 (br d, J=7.5 Hz, 1H, $H_3$), 7.48 (ddd, J=0.8, 4.8, 8.0 Hz, 1H, $H_5$), 7.39 (dd=7.5, 8.5 Hz, 1H, $H_4$), 2.39 (s, 3H, $CH_3$).

EXAMPLE 12

Preparation of 2-(2,6-Difluorophenyl)benzimidazole

In this Example, 2-(2,6-difluorophenyl)benzimidazole (18) was prepared using Method B. The basic method of "Method B" was used in subsequent Examples, as indicated below, with reagent and other substitutions made as indicated.

First, 2-methyl-6-nitroaniline (9) (9.31 g, 31.9 mmol) was dissolved in glacial acetic acid (100 mL). Iron powder (17) (4.95 g) was then added. After 30 min at reflux, the reaction was concentrated to dryness, eluting with ethylacetate and washed with $NaHCO_3$. The aqueous layer was back extracted with ethylacetate and the combined organic solution was washed with $NaHCO_3$ (sat. aq.) and NaCl (sat. aq.). The combined washings were dried ($Na_2SO_4$), filtered and concentrated. The crude product was recrystallized from ethylacetate to yield white powders of 2-(2,6-Difluorophenyl)benzimidazole (6.24 g, 27.1 mmol, 85% yield). $^1$H-NMR (300 MHz, $CD_2Cl_2$): δ 9.92 (br, 1H, NH), 7.69 (br, 1H, $H_{4,7}$), 7.45 (m, 1H, H..), 7.31 (ddd, J=3.2, 4.0, 6.0 Hz, $H_{5,6}$), 7.11 (m, 2H, $H_{3',5'}$).

EXAMPLE 13

Preparation of 2-(2,6-Difluorophenyl)-4-Methylbenzimidazole

In this Example, 2-(2,6-difluorophenyl)-4-methylbenzimidazole (19) was produced using Method B. N-(2,6-difluorobenzoyl)-2-methyl-6-nitroanilide (11) (1.35 g, 4.62 mmol) and iron powder (17) (1.3 g) were mixed as described for Method B. Recrystallization of the crude product from diethylether/hexane (3/1) yielded colorless crystals of 2-(2,6-difluorophenyl)-4-methylbenzimidazole (1.1 g, 4.48 mmol, 97%). M.p. 148° C. $^1$H-NMR (300 MHz, DMSO-$d_6$): δ 12.86 (s, 1H, NH), 7.66 (m, 1H, $H_4$), 7.33 (m, 2H, $H_{3',5'}$), 7.27–7.18 (m, 1H, $H_7$), 7.15 (dd, J=8.0, 7.2 Hz, 1H, $H_6$), 7.05 (d, J=7.2 Hz, 1H, $H_5$), 2.55 (s, 3H, $CH_3$).

EXAMPLE 14

Preparation of 2-(2-Methylphenyl)Benzimidazole

In this Example, 2-(2-methylphenyl)benzimidazole (20) was produced using Method B. N-(2-methylbenzoyl)-2-nitroanilide (13) (1.9 g, 7.4 mmol) and iron powder (17) (1.2 g) were mixed. Recrystallization of the crude product from diethylether/hexane (3/1) yielded colorless crystals of 2-(2-methylphenyl)benzimidazole 1.2 g (5.76 mmol, 78%). M.p. 215° C. $^1$H-NMR (300 MHz, $CD_2Cl_2$): δ 7.63 (m, 1H, $H_6$), 7.58 (dd, J=6.1, 3.2 Hz, 2H, $H_{4,\,7}$), 7.39–7.21 (m, 3H, $H_{3',4',5'}$), 7.25 (dd, J=6.1, 3.2 Hz, 2H, $H_{5,\,6}$) 2.58 (s, 3H, $CH_3$).

EXAMPLE 15

Preparation of 2-(1-Naphthyl)-4-Methylbenzimidazole

In this Example, 2-(1-naphthyl)-4-methylbenzimidazole (21) was produced using Method B. The 1-naphthyl derivative shown as compound 14 (FIG. 3) (2.60 g, 11.7 mmol) and iron powder (17) (2.00 g) were reacted. Purification of the crude product by flash chromatography, eluting with 4% MeOH/$CH_2Cl_2$, and recrystallization from diethylether/ hexane (3:1) yielded white powders of 2-(1-naphthyl)-4-methylbenzimidazole (1.63 g, 6.31 mmol, 54% yield). $^1$H-NMR (200 MHz, $CD_2Cl_2$): δ 9.71 (br, 1H, NH), 8.80 (m, 1H), 8.01–7.89 (m, 2H), 7.81 (dd, J=1.3, 7.3 Hz, 1H), 7.61–7.47 (m, 4H), 7.21 (dd, J=7.3, 7.6 Hz, 1H), 7.11 (m, 1H), 2.66 (s, 3H, $CH_3$).

EXAMPLE 16

Preparation of 2-(2-Naphthyl)-4-Methylbenzimidazole

In this Example, 2-(2-naphthyl)-4-methylbenzimidazole (22), using Method B. The compound shown as compound 15 (FIG. 3) (2.25 g, 7.34 mmol) and iron powder (17) (1.60 g) were reacted. The crude product was purified by flash chromatography eluting with 4% MeOH/$CH_2Cl_2$, and recrystallization from diethylether/hexane (3:1), yielding white powders of 2-(2-naphthyl)-4-methylbenzimidazole (1.00 g, 3.88 mmol, 53% yield). $^1$H-NMR (300 MHz, $CD_2Cl_2$): δ 8.70 (br, 1H, NH), 8.34 (dd, J=1.7, 8.6 Hz, 1H), 7.99–7.87 (m, 3H), 7.57–7.51 (m, 2H), 7.50–7.43 (m, 1H), 7.15 (dd, J=7.3, 7.5 Hz, 1H, $H_6$), 7.04 (m, 1H, $H_5$) 2.67 (s, 3H, $CH_3$).

EXAMPLE 17

Preparation of 2-(3-Pyridyl)-4-Methylbenzimidazole

In this Example, 2-(3-pyridyl)-4-methylbenzimidazole (23) was produced using Method B. N-Nicotinoyl-2-methyl- 6-nitroanilide (Example 7) (1.00 g, 3.89 mmol) and iron (0.75 g) were mixed for 30 minutes. Additional iron powder (0.75 g) was then added, and the mixture prepared as described for Method B. Recrystallization of the crude product from ethylacetate yielded white powders of 2-(3-pyridyl)-4-methylbenzimidazole (0.72 g, 3.44 mmol, 88% yield). $^1$H-NMR (300 MHz, DMSO-d$_6$): δ 9.38 (dd, J=2.3, 0.9 Hz, 1H, H$_{2'}$), 8.67 (dd, J=1.7, 4.8 Hz, 1H, H$_{6'}$), 8.53 (ddd, J=1.7, 2.3, 8.0 Hz, 1H, H$_{4'}$), 7.58 (ddd, J=0.9, 4.8, 8.0 Hz, 1H, H$_{5'}$), 7.44 (dd, J=0.9, 8.1 Hz, H$_7$), 7.12 (dd, J=7.3, 8.1 Hz, 1H, H$_6$), 7.02 (ddt, J=0.2, 0.9, 7.3 Hz, 1H, H$_5$), 2.59 (s, 3H, CH$_3$).

EXAMPLE 18

Preparation of 2-(4-Pyridyl)-4-Methylbenzimidazole

In this Example, 2-(4-pyridyl)-4-metlhylbenzimidazole (24) was produced using Method B. N-Isonicotinoyl-2-methyl-6-nitroanilide (Example 7) (1.02 g, 3.97 mmol) and iron powder (1.10 g) were mixed as described for Method B. Recrystallization of the crude product from ethylacetate yielded white powders of 2-(4-pyridyl)-4-methylbenzimidazole (0.70 g, 3.34 mmol, 84% yield). $^1$H-NMR (300 MHz, DMSO-d$_6$): δ 8.75 (m, 2H, H$_{2',6'}$), 8.14 (m, 2H, H$_{2',5'}$), 7.46 (dd, J=0.9, 8.1 Hz, 1H, H$_7$), 7.15 (dd, J=7.3, 8.1 Hz, 1H, H$_6$), 7.05 (ddt, J=0.8, 0.9, 7.3 Hz, 1H, H$_5$), 2.59 (s, 3H, CH$_3$).

EXAMPLE 19

Preparation of 1-(2,6-Difluorobenzyl)-2-(2,6-Difluorophenyl)Benzimidazole

In this Example, 1-(2,6-difluorobenzyl)-2-(2,6-difluorophenyl)benzimidazole (26) was prepared using Method C. The basic method of "Method C" was used in subsequent Examples, as indicated below, with reagent and other substitutions made as indicated.

2-(2,6-difluorophenyl)benzimidazole (Example 12) (2.00 g, 8.70 mmol) and 2,6-difluoro-α-bromo-toluene (25) (2.85 g, 160 M %), were dissolved in THF (20 mL). To this mixture, NaH (0.75 g, 215 M %) was added. After mixing for 2 hours, the reaction was quenched with MeOH and concentrated. The residue was redissolved in ethylacetate, and washed with NaHCO$_3$ (sat. aq.) and NaCl (sat. aq.). The combined washings were dried (Na$_2$SO$_4$), filtered and concentrated. The crude product was recrystallized from ethylacetate/hexane (1:1) yielding white powders of 1-(2,6-difluorobenzyl)-2-(2,6-difluorophenyl)benzimidazole (2.62 g, 0.35 mmol, 85% yield. M.p. 145° C. $^1$H-NMR (300 MHz, CD$_2$Cl$_2$): δ 7.77 (m, 1H, H$_4$), 7.54 (m, 1H, H$_{4'}$), 7.49m, 1H, H$_7$), 7.29 (m, 2H, H$_{5,6}$), 7.24 (m, 1H, H$_{4''}$), 7.08 (m, 2H, H$_{3',5'}$), 5.82 (m, 2H, H$_{3'',5''}$), 5.30 (s, 2H, CH$_2$PhF$_2$).

EXAMPLE 20

Preparation of 1-Benzyl-2-(2,6-Difluorophenyl) Benzimidazole

In this Example, 1-benzyl-2-(2,6-difluorophenyl) benzimidazole (28) was produced using Method C. 2-(2,6-difluorophenyl)benzimidazole (Example 12) (100 mg, 0.43 mmol) and benzylbromide (27) (66.4 μl, 0.56 mmol) were mixed as indicated for Method C. Recrystallization of the crude product from diethylether/hexane (3:1) yielded colorless crystals of 1-benzyl-2-(2,6-difluorophenyl) benzimidazole (77 mg, 0.24 mmol, 56%). M.p. 124° C. $^1$H-NMR (300 MHz, CDCl$_3$): δ 7.88 (d, J=7.7 Hz, 1H, H$_4$), 7.47 (m, 1H, H$_{4'}$), 7.34–7.22 (m, 6H, H$_{5,6,7,2'',4'',6''}$), 7.07–6.99 (m, 4H, H$_{3'5',3'',5''}$), 5.28 (s, 2H, CH$_2$).

EXAMPLE 21

Preparation of 1-Benzyl-2-(2,6-Difluorophenyl)-4-Methylbenzimidazole

In this Example, 1-benzyl-2-(2,6-difluorophenyl)-4-methylbenzimidazole (29) was produced according to Method C. 2-(2,6-difluorophenyl)-4-methylbenzimidazole (Example 13) (88 mg, 0.33 mmol) and benzylbromide (27) (51 μL, 0.43 mmol) were reacted. Recrystallization of the crude product from diethylether/hexane (3:1) yielded colorless crystals of 1-benzyl-2-(2,6-difluorophenyl)-4-methylbenzimidazole (67 mg, 0.20 mmol, 61%). M.p. 112–117° C. $^1$H-NMR (300 MHz, CDCl$_3$): δ 7.46 (m, 1H, H$_{4'}$), 7.26–7.22 (m, 3H, H$_{7,3'',5''}$), 7.18–6.98 (m, 7H, H$_{5,6,3',5',2'',4'',6''}$), 5.25 (s, 2H, CH$_2$), 2.74 (s, 3H, CH$_3$). Anal. (C$_{21}$H$_{16}$F$_2$N$_2$x1/4H$_2$O) calcd. C,H,N 74.43, 4.91, 8.27; found C,H,N 74.81, 4.90, 7.85. HRMS 334.1281 (calcd) 334.1266 (found) δ ppm 4.6.

EXAMPLE 22

Preparation of 1-(2,6-Dichlorobenzyl)-2-(2,6-Difluorophenyl)-4-Methylbenzimidazole In this Example, 1-(2,6-dichlorobenzyl)-2-(2,6-difluorophenyl)-4-methylbenzimidazole (30) was produced using Method C. In this Example, 2-(2,6-difluorophenyl)-4-methylbenzimidazole (Example 13) (0.50 g, 2.05 mmol) and 2,6-dichloro-α-bromo-toluene (0.74 g, 3.08 mmol, 150 M %) were reacted for 2 hours. The crude product was purified by flash chromatography, eluted with 4% MeOH/CH$_2$Cl$_2$, and recrystallized from diethylether/hexane (3:1), yielding white powders of 1-(2,6-dichlorobenzyl)-2-(2,6-difluorophenyl)-4-methylbenzimidazole (0.70 g, 1.74 mmol, 85% yield). M.p. 202–203° C. $^1$H-NMR (300 MHz, CD$_2$Cl$_2$): δ 7.48 (m, 1H, H$_4$), 7.26 (m, 2H, H$_{5,7}$), 7.19 (dd, J=8.0, 8.2 Hz, 1H, H$_6$), 7.14–6.98 (m, 5H, H$_{3',5',3'',4'',5''}$), 5.56 (s, 2H, CH$_2$PhCl$_2$), 2.64 (s, 3H, CH$_3$).

EXAMPLE 23

Preparation of 1-(2,6-Difluorobenzyl)-2-t-Butyldimethylsilyloxymethyl-4-Methylbenzimidazole In this Example, 1-(2,6-difluorobenzyl)-2-t-butyldimethylsilyloxymethyl-4-methylbenzimidazole (31) was produced using Method C. In this Example, 2-(t-Butyldimethylsilyloxymethyl)-4-Methylbenzimidazole (Example 3) (3.25 g, 11.76 mmol) and 2,6-difluoro-α-bromo-toluene (25) (3.65 g, 150 M %) were reacted for 4 h. The crude product was purified by flash chromatography eluting with ethylacetate:hexane (1:4), yielding white powders of 1-(2,6-difluorobenzyl)-2-t-butyldimethylsilyloxymethyl-4-methylbenzimidazole (4.41 g, 10.96 mmol, 93% yield). $^1$H-NMR (300 MHz, CD$_2$Cl$_2$): δ 7.32 (m, 1H, H$_{4''}$), 7.17 (br d, J=8.2 Hz, 1H, H$_7$), 7.08 (dd, J=7.3, 8.2 Hz, 1H, H$_6$), 7.00 (br d, J=7.3 Hz, 1H, H$_5$), 6.95 (m, 2H, H$_{3'',5''}$), 5.63 (s, 2H, CH$_2$PhF$_2$), 5.13 (s, 2H, CH$_2$O), 2.59 (s, 3H, CH$_3$), 0.94 (s, 9H, Si-tert-Bu), 0.14 (s, 6H, Si(CH$_3$)$_2$).

EXAMPLE 24

Preparation of 1-(2,6-Difluorobenzyl)-2-(2,6-Difluorobenzyloxymethyl)Benzimidazole In this Example, 1-(2,6-difluorobenzyl)-2-(2,6-difluorobenzyloxymethyl)benzimidazole (32) was produced using Method C. In this Example, 2-hydroxymethylbenzimidazole (Example 1) (92 mg, 0.62 mmol) and 2,6-difluoro-α-bromo-toluene (334 mg, 1.61 mmol, 260 M %) were reacted. Recrystallization of the crude product from diethylether/hexane (3:1) yielded colorless crystals of 1-(2,6-difluorobenzyl)-2-(2,6-difluorobenzyloxymethyl)benzimidazole (66 mg, 0.165 mmol, 27%). M.p. 109° C. $^1$H-NMR (300 MHz, CDCl$_3$): δ 7.73 (m, 1H, H$_4$), 7.38 (m, 1H, H$_7$), 7.36–7.18 (m, 4H, H$_{5,6,4'4''}$), 6.98–6.82 (m, 4H, H$_{3',5'3'',5''}$), 5.58 (s, 2H, NCH$_2$PhF$_2$), 5.07 (s, 2H, OCH$_2$), 4.70 (s, 2H, OCH$_2$PhF$_2$).

EXAMPLE 25

Preparation of 1-(2,6-Difluorobenzyl)-2-(2,6-Difluorophenyl)-4-Methylbenzimidazole In this Example, 1-(2,6-difluorobenzyl)-2-(2,6-difluorophenyl)-4-methylbenzimidazole (33) was produced using Method C. 2-(2,6-difluorophenyl)-4-methylbenzimidazole (Example 13) (400 mg, 1.63 mmol) and 2,6-difluoro-α-bromo-toluene (1.87 mmol, 388 mg) were mixed and stirred overnight. Recrystallization of the crude product from diethylether/hexane (3:1) yielded white powders of 1-(2,6-difluorobenzyl)-2-(2,6-difluorophenyl)-4-methylbenzimidazole (453 mg, 1.22 mmol, 75% yield). M.p. 182–186° C. $^1$H-NMR (300 MHz, CDCl$_3$): δ 7.48 (m, 1H, H$_4$), 7.32 (d, J=8.1 Hz, H$_7$), 7.20 (m, 1H, H$_{4''}$), 7.19 (dd, J=8.1, 7.2 Hz, 1H, H$_6$), 7.09 (d, J=7.2 Hz, 1H, H$_5$), 7.04 (m, 2H, H$_{3',5'}$), 6.79 (m, 2H, H$_{3'',5''}$), 5.33 (s, 2H, CH$_2$), 2.70 (s, 3H, CH$_3$).

EXAMPLE 26

Preparation of 1-(2,6-Difluorobenzyl)-2-Isopropyl-4-Methylbenzimidazole

In this Example, 1-(2,6-difluorobenzyl)-2-isopropyl-4-methylbenzimidazole (34) was prepared according to Method C. 2-isopropyl-4-methylbenzimidazole (Example 4) (0.20 g 1.15 mmol) and 2,6-difluoro-α-bromo-toluene (0.36 g, 1.74 mmol, 150 M %) were stirred for 5 h. The crude product was purified by flash chromatography eluting with 4% MeOH/CH$_2$C$_2$, and recrystallized from diethylether/hexane (3:1), yielding white powders of 1-(2,6-difluorobenzyl)-2-isopropyl-4-methylbenzimidazole (0.20 g, 0.67 mmol, 58% yield). M.p. 151–153° C. $^1$H-NMR (200 MHz CD$_2$Cl$_2$): δ 7.30 (m, 1H, H$_{4''}$), 7.15 (br d, J=7.7 Hz, 1H, H$_7$), 7.04 (dd, J=7.3, 7.7 Hz, 1H, H$_6$), 6.96 (br, d J=7.3 Hz, 1H, H$_5$), 6.82 (m, 2H, H$_{3'',5''}$), 5.38 (s, 2H, CH$_2$PhF$_2$), 3.40 (sep, j=6.8 Hz, 1H, iPr), 2.57 (s, 3H, CH$_3$), 1.38 (d, J=6.8 Hz, 6H, iPr).

EXAMPLE 27

Preparation of 1-(2,6-Difluorobenzyl)-2-Methylbenzimidazole

In this Example, 1-(2,6-difluorobenzyl)-2-methylbenzimidazole (35) was prepared according to Method C. 2-methylbenzimidazole (204 mg, 1.54 mmol) and 2,6-difluoro-α-bromo-toluene (351 mg, 1.70 mmol) were reacted. The crude product was purified by recrystallization from diethylether:hexane (3:1), yielding colorless crystals of 1-(2,6-difluorobenzyl)-2-methylbenzimidazole (290 mg, 1.12 mmol, 73%). M.p. 99° C. $^1$H-NMR (300 MHz, CDCl$_3$): δ 7.66 (m, J=8.0, 1.1, 0.6 Hz, 1H, H$_4$), 7.37 (m, J=0.6, 1.1, 8.2 Hz, H$_7$), 7.30 (m, 1H, H$_{4''}$), 7.20 (m, J=8.0, 1.1, 7.3, H$_5$), 7.19 (m, J=8.2, 7.3, 1.1 Hz, 1H, H$_6$), 6.92 (m, 2H, H$_{3'',5''}$) 5.35 (s, 2H, CH$_2$), 2.71 (s, 3H, CH$_3$).

EXAMPLE 28

Preparation of 1-(2,6-Difluorobenzyl)-2-(2-Methylphenyl)Benzimidazole

In this Example, 1-(2,6-difluorobenzyl)-2-(2-methylphenyl)benzimidazole (36) was produced according to Method C. 2-(2-methylphenyl)benzimidazole (Example 14) (0.10 g, 0.48 mmol) was reacted with 2,6-difluoro-α-bromo-toluene (0.15 g, 0.73 mmol, 150 M %). The crude product was purified using flash chromatography eluting with 2% MeOH/CH$_2$Cl$_2$, and recrystallization with diethyl ether/hexane (3:1), yielding colorless crystals of 1-(2,6-difluorobenzyl)-2-(2-methylphenyl)benzimidazole (109 mg, 0.33 mmol, 68%). M.p. 139° C. $^1$H-NMR (300 MHz, CDCl$_3$): δ 7.80 (m, 1H, H$_4$), 7.43–7.23 (m, 7H, H$_{5,6,7,3',4'5,6'}$), 7.21 (m, 1H, H$_{4''}$), 6.79 (m, 2H, H$_{3'',5''}$), 5.31 (s, 2H, CH$_2$), 2.23 (s, 3H, CH$_3$).

EXAMPLE 29

Preparation of 1-(2,6-Difluorobenzyl)-2-(l1-Naphthyl)-4-Methylbenzimidazole

In this Example, 1-(2,6-difluorobenzyl)-2-(1-naphthyl)-4-methylbenzimidazole (37) was produced according to Method C. 2-(1-naphthyl)-4-methylbenzimidazole (Example 15) (0.30 g, 1.16 mmol) and 2,6-difluoro-α-bromo-toluene (25) (0.54 g, 2.60 mmol, 225 M %) were reacted with stirring overnight. The crude product was purified by flash chromatography eluting with ethylacetate/hexane (1:4) and recrystallization from diethylether/hexane (3:1), yielding white powders of 1-(2,6-difluorobenzyl)-2-(1-naphthyl)-4-methylbenzimidazole (0.32 g, 0.83 mmol, 72% yield). M.p. 121–123° C. $^1$H-NMR (300 MHz, CD$_2$Cl$_2$): δ 8.00 (d, J=8.1 Hz, 1H), 7.96 (d, J=8.1 Hz, 1H), 7.66 (d, J=6.3 Hz, 1H), 7.60 (t, J=7.5 Hz, 1H), 7.53 (dt, J=1.3, 7.5 Hz, 1H), 7.43 (dt, J=1.3, 7.6 Hz, 1H), 7.28 (d, J=8.1 Hz, 1H), 7.19 (t, J=7.5 Hz, 1H), 7.11 (m, 2H), 6.67 (m, 2H), 5.28 (s, 2H, CH$_2$PhF$_2$), 2.68 (s, 3H, CH$_3$).

EXAMPLE 30

Preparation of 1-(2,6-Difluorobenzyl)-2-(2-Naphthyl)-4-Methylbenzimidazole

In this Example, 1-(2,6-difluorobenzyl)-2-(2-naphthyl)-4-methylbenzimidazole (38) was produced according to Method C. 2-(2-naphthyl)-4-methylbenzimidazole (Example 16) (0.30 g, 1.16 mmol) was reacted with a first addition of 2,6-difluoro-α-bromo-toluene (0.36 g, 1.74 mmol, 150 M %), followed by a second addition of 2,6-difluoro-α-bromo-toluene (0.18 g, 0.87 mmol, 75 M %) after 2 hours of stirring. The reaction mixture was stirred overnight. The crude product was purified by flash chromatography eluting with ethylacetate/hexane (1:4), and recrystallized from diethylether/hexane (3:1), yielding white powders of 1-(2,6-difluorobenzyl)-2-(2-naphthyl)-4-methylbenzimidazole (0.35 g, 0.91 mmol, 78% yield). M.p. 175–176° C. $^1$H-NMR (300 MHz, CD$_2$Cl$_2$): δ 8.28(d, J=1.6 Hz, 1H), 8.02 (d, J=8.5 Hz, 1H), 7.96 (m, 2H), 7.83 (dd, J=1.7, 8.5 Hz, 1H), 7.59 (m, 2H), 7.20(m, 2H), 7.12 (m, 1H), 7.06 (m, 1H), 6.80 (m, 2H), 5.60 (s, 2H, CH$_2$PhF$_2$), 2.66 (s, 3H, CH$_3$).

EXAMPLE 31

Preparation of 1-(2,6-Difluorobenzyl)-2-Phenylbenzimidazole

In this Example, 1-(2,6-difluorobenzyl)-2-phenylbenzimidazole (39) was produced according to Method C. 2-phenylbenzimidazole (300 mg, 1.54 mmol) and 2,6-difluoro-α-bromo-toluene were reacted (1.70 mmol, 110 M %). The crude product was recrystallized from diethylether:hexane (3:1), yielding colorless crystals of 1-(2, 6-difluorobenzyl)-2-phenylbenzimidazole (300 mg, 0.94 mmol, 63% yield). M.p. 163° C. $^1$H-NMR (300 MHz, CDCl$_3$): δ 7.82 (d, J=8.3 Hz, 1H, H$_4$), 7.75 (m, 2H 2H$_{3',5'}$), 7.53 (m, 3H, H$_{2', 4',6'}$), 7.33 (d, J=8.3 Hz, 1H, H$_7$), 7.25 (m, 3H, H$_{5,6,4''}$), 6.81 (m, 2H, H$_{3'',5''}$), 5.55 (s, 2H, CH$_2$).

EXAMPLE 32

Preparation of 1-(2,6-Difluorobenzyl)-2-(3-Pyridyl)-4-Methylbenzimidazole

In this Example, 1-(2,6-difluorobenzyl)-2-(3-pyridyl)-4-methylbenzimidazole (40) was produced according to Method C. 2-(3-pyridyl)-4-methylbenzimidazole (Example 17) (0:30 g, 1.43 mmol) and 2,6-difluoro-α-bromo-toluene (0.49 g, 2.37 mmol, 165 M %) were reacted and stirred overnight. The crude product was purified by flash chromatography eluting with 4% MeOH/CH$_2$Cl$_2$, and recrystallization from diethylether/hexane (3:1), yielding white powders of 1-(2,6-difluorobenzyl)-2-(3-pyridyl)-4-methylbenzimidazole (0.34 g, 1.02 mmol, 71% yield). M.p. 186–188° C. $^1$H-NMR (300 MHz, CD$_2$Cl$_2$): δ 8.92 (dd, J=0.9, 2.3 Hz, 1H, H$_{2''}$), 8.74 (dd, J=1.7, 4.9 Hz, 1H, H$_6$), 8.05 (dt, J=2.0, 7.8 Hz, 1H, H$_{4'}$), 7.48 (ddd, J=0.9, 4.9, 7.8, 1H, H$_5$), 7.24 (m, 1H, H$_{4''}$), 7.22 (br d, J=7.7 Hz 1H, H$_7$), 7.15 (dd, J=7.7, 7.2, 1H, H$_6$), 7.07 (dt, J=1.0, 7.2 Hz 1H H$_5$), 6.83 (m, 2H, H$_{3''5''}$), 5.51 (s, 2H, CH$_2$PhF$_2$), 2.64 (s,3H, CH$_3$).

EXAMPLE 33

Preparation of 1-(2,6-Difluorobenzyl)-2-(4-Pyridyl)-4-Methylbenzimidazole

In this Example, 1-(2,6-difluorobenzyl)-2-(4-pyridyl)-4-methylbenzimidazole (41) was produced according to Method C. 2-(4-pyridyl)-4-methylbenzimidazole (Example 18) (0.30 g, 1.43 mmol) and 2,6-difluoro-α-bromo-toluene (0.45 g, 2.17 mmol, 150 M %) were reacted and stirred overnight. The crude product was purified by flash chromatography eluting with 4% MeOH/CH$_2$Cl$_2$, and recrystallization from diethylether/hexane (3:1), yielding white powders of 1-(2,6-difluorobenzyl)-2-(4-pyridyl)-4-methylbenzimidazole (0.29 g, 0.86 mmol, 60% yield). M.p. 171–172° C. $^1$H-NMR (300 MHz, CD$_2$Cl$_2$): δ 8.77 (dd, J=1.6, 4.4 Hz, 2H, H$_{2',6'}$), 7.66 (dt, J=1.4, 4.4 Hz, 2H, H$_{3',5'}$), 7.24 (m, 1H, H$_{4''}$), 7.22 (dd, J=0.8, 8.1 Hz, 1H, H$_7$), 7:15 (dd, J=7.5, 8.1 Hz, 1H, H$_6$), 7.07 (ddq, J=0.4, 0.8, 7.5 Hz, 1H, H$_5$), 6.82 (m, 2H, H$_{3'', 5''}$), 5.54 (s, 2H, CH$_2$PhF$_2$), 2.63 (s, 3H, CH$_3$).

EXAMPLE 34

Preparation of 1-(2,3,4,5,6-Pentafluorobenzyl)-2-(2,6-Difluorophenyl)-4-Methylbenzimidazole In this Example, 1-(2,3,4,5,6-pentafluorobenzyl)-2-(2,6-difluorophenyl)-4-methylbenzimidazole (42) was prepared according to Method C. 2-(2,6-difluorophenyl)-4-methylbenzimidazole (Example 13) (0.31 g, 1.27 mmol) and 2,3,4,5,6-pentafluoro-α-bromo-toluene (0.30 mL, 1.99 mmol, 155 M %) were reacted and stirred for 4 h. The crude product was purified by flash chromatography eluting with 4% MeOH/CH$_2$Cl$_2$, and recrystallization from diethylether/hexane (3:1), yielding white powders of 1-(2,3,4,5,6-pentafluorobenzyl)-2-(2,6-difluorophenyl)-4-methylbenzimidazole (0.33 g, 0.77 mmol, 61% yield). M.p. 155–156° C. $^1$H-NMR (200 MHz, CD$_2$Cl$_2$); δ 7.57 (m, 1H, H$_6$), 7.29–7.23 (m, 2H, H$_{6,7}$), 7.19–7.05 (m, 3H, H$_{5,3',5'}$), 5.35 (s, 2H, CH$_2$PhF$_5$), 2.64 (s, 3H, CH$_3$).

EXAMPLE 35

Preparation of 1-(3-Pyridylmethyl)-2-(2,6-Difluorophenyl)-4-Methylbenzimidazole

In this Example, 1-(3-pyridylmethyl)-2-(2,6-difluorophenyl)-4-methylbenzimidazole (43) was produced according to Method C. 2-(2,6-difluorophenyl)-4-methylbenzimidazole (Example 13) (0.21 g, 0.86 mmol) and α-bromo-methylpyridine (0.22 g, 1.28 mmol, 150 M %) were reacted and stirred for 1 h. The crude product was purified by flash chromatography eluting with ethylacetate/hexane (1:1) increasing to ethylacetate (100%), and recrystallization from diethyl ether:hexane (3:1), yielding white powders of 1-(3-pyridylmethyl)-2-(2,6-difluorophenyl)-4-methylbenzimidazole (0.24 g (0.73 mmol, 85% yield). M.p. 131–132° C. $^1$H-NMR (300 MHz, CD$_2$Cl$_2$): δ 8.45 (d, J=3.4 Hz, 1H, H$_{6''}$), 8.32 (s, 1H, H$_{2''}$), 7.53 (m, 1H, H$_{4'}$), 7.25–7.03 (m, 7H, H$_{5,6,7,3',5'4'',5''}$), 5.26 (s, 2H, CH$_2$Py), 2.67 (s, 3H, CH$_3$—Ar).

EXAMPLE 36

Preparation of 1-(3,3-Dimethylallyl)-2-(Cyclopropyl)-4-Methoxylbenzimidazole

In this Example, 1-(3,3-Dimethylallyl)-2-(cyclopropyl)-4-methoxylbenzimidazole was produced using Method C, by reacting 2-(Cyclopropyl)-4-methoxylbenzimidazole (5014, Example 49) (1.00 g, 5.32 mmol) and 3,3-dimethylallyl bromide (0.70 mL, 6.07 mmol, 115 M %). The crude product was purified by flash chromatography eluting with 2% MeOH/CH$_2$Cl$_2$ and recrystallization from diethylether/hexane (3:1), yielding white crystals of 1-(3,3-dimethylallyl)-2-cyclopropyl-4-methoxylbenzimidazole (1.08 g, 4.21 mmol, 80% yield). M.p. 41–42° C. $^1$H-NMR (200 MHz, CD$_2$Cl$_2$) δ 7.09 (dd, J=8.1, 7.9 Hz, 1H, H$_6$), 6.89 (dd, J=8.1, 0.9 Hz, 1H, H$_5$), 6.61 (dd, J=7.9, 0.9 Hz, 1H, H$_7$), 5.26 (m, 1H), 4.81 (d, J=6.7 Hz, 2H), (3.94, s, 3H, OCH$_3$), 1.96 (m, 1H), 1.86 (s, 3H, CH$_3$), 1.74 (d, J=1.2 Hz, 3H, CH$_3$), 1.21–0.98 (m, 4H).

EXAMPLE 37

Preparation of 1-Benzenesulfonyl-2-(2,6-Difluorophenyl)benzimidazole

In this Example, 1-benzenesulfonyl-2-(2,6-difluorophenyl)benzimidazole (45) was produced according to Method D. The basic method of "Method D" was used in subsequent Examples, as indicated below, with reagent and other substitutions made as indicated.

2-(2,6-difluorophenyl)benzimidazole (Example 12) (0.31 g, 1.34 mmol) dissolved in THF (5 mL) was added to NaH (0.10 g, 190 M %). After 5 min, benzenesulfonyl chloride (0.25 mL, 0.35 g, 2.00 mmol, 150 M %) was added. After stirring for 2 h, the reaction was dissolved in ethylacetate, and washed with NaHCO$_3$ (sat. aq.) and NaCl (sat. aq.). The combined washings were dried (Na$_2$SO$_4$), filtered, and concentrated. The product was purified by flash chromatography eluting with 2% MeOH/CH$_2$Cl$_2$ and then recrystallized from diethylether/hexane (3:1), to yield white powders of 1-benzenesulfonyl-2-(2,6-difluorophenyl)benzimidazole (0.41 g, (1.10 mmol, 83% yield). M.p. 104–106° C. ¹H-NMR (300 MHz, CD₂Cl₂): δ 8.09 (m, 1H, PhSO₂), 7.77 (m, 1H, PhSO₂), 7.69 (m, 2H, PhSO₂), 7.66–7.53 (m, 2H, H$_{4,7}$), 7.51–7.39 (m, 4H, PhSO₂, H$_{3,5}$), 7.07 (m, 2H, H$_{3',5'}$).

EXAMPLE 38

Preparation of 1-Benzenesulfonyl-2-(2,6-Difluorophenyl)-4-Methylbenzimidazole

In this Example, 1-benzenesulfonyl-2-(2,6-difluorophenyl)-4-methylbenzimidazole (46) was produced according to Method D, by reacting 2-(2,6-difluorophenyl)-4-methylbenzimidazole (Example 13) (0.20 g, 0.82 mmol) and benzenesulfonyl chloride (0.20 mL, 0.28 g. 1.58 mmol, 190 M %). The crude product was purified by flash chromatography eluting with 2% MeOH/CH₂Cl₂ and recrystallized from diethylether/hexane (3:1), to produce white powders of 1-benzenesulfonyl-2-(2,6-difluorophenyl)-4-methylbenzimidazole (0.24 g, 0.02 mmol, 76% yield). M.p. 134–135° C. ¹H-NMR (200 MHz, CD₂Cl₂): δ 7.89 (br d, J=8.2 Hz, 1H), 7.73–7.38 (m, 6H), 7.34 (dd, J=7.4, 8.1 Hz, 1H, H₆), 7.2 (br d, J=7.4 Hz, 1H, H₅), 7.07 (m, 2H, H$_{3',5'}$), 2.59 (s, 3H, CH₃).

EXAMPLE 39

Preparation of 1-(2,6-Difluorobenzoyl)-2-(2,6-Difluorophenyl)Benzimidazole

In this Example, 1-(2,6-difluorobenzoyl)-2-(2,6-difluorophenyl)benzimidazole (47) was produced according to Method D. To 2-(2,6-difluorophenyl)benzimidazole (Example 12) (30 mg, 0.13 mmol) dissolved in pyridine (0.5 mL) and chloroform (1.2 mL) was added 2,6-difluorobenzoyl chloride (20 μl, 0.16 mmol, 120 M %). The mixture was stirred at room temperature for 5 h, diluted with chloroform, and washed with NaHSO₄ (2% solution). The organic layer was dried (Na₂SO₄), filtered, and evaporated. The solid was recrystallized from diethylether/hexane to produce, 19 mg of colorless crystals (40% yield). M.p. 145° C. ¹H-NMR (300 MHz, CDCl₃): δ 8.14 (m, 1H, H₄), 7.89 (m, 1H, H₇), 7.48 (m, 2H, H$_{5,6}$), 7.31–7.18 (m, 2H, H$_{4',4''}$), 6.77 (m, 4H, H$_{3',5',3'',5''}$).

EXAMPLE 40

Preparation of 1-(2,6-Difluorobenzyl)-2-Hydroxymethyl-4-Methylbenzimidazole

In this Example, 1-(2,6-difluorobenzyl)-2-hydroxymethyl-4-methylbenzimidazole (48) was prepared according to Method D. To 1-(2,6-difluorobenzyl)-2-t-butyldimethylsilyloxymethyl-4-methylbenzimidazole (Example 23) (1.82 g, 4.52 mmol) dissolved in THF (20 mL) was added tetrabutyl ammonium fluoride (1.45 g, 4.60 mmol, 100 M %). After stirring for 30 min at room temperature, the reaction was concentrated to dryness. The residue was suspended in water, filtered, and washed with water to produce 1.28 g, (4.44 mmol, 98% yield) of white powder. ¹H-NMR (300 MHz, CD₃OD): δ 7.39(m, 1H, H$_{4''}$), 7.18 (br d, J=8.3 Hz, 1H, H₇), 7.09 (dd, J=7.4, 8.3 Hz, 1H, H₆), 7.05–6.97 (m, 3H, H$_{3'',5'',5}$), 5.68 (s, 2H, CH₂PhF₂), 4.99 (s, 2H, CH₂O), 2.57 (s, 3H, CH₃).

EXAMPLE 41

Preparation of 1-(2,6-Difluorobenzyl)-4-Methylbenzimidazole

In this Example, 1-(2,6-difluorobenzyl)-4-methylbenzimidazole (49) was prepared according to Method D. To 1-(2,6-difluorobenzyl)-2-hydroxymethyl-4-methylbenzimidazole (Example 40) (1.82 g, 4.52 mmol) dissolved in 1.5 M H₂SO₄ (40 mL) was added KMnO₄ (1.50 g, 9.49 mmol, 160 M %). After 1 h at room temperature, the reaction mixture was filtered and washed with water. The brown solid was collected, suspended in acetone/methanol and filtered. The filtrate was collected and purified by flash chromatography eluting with 10% MeOH/CH₂Cl₂ increasing to 50% MeOH/CH₂Cl₂ to produce 1.42 g (4.70 mmol, 80% yield) of white powder. ¹H-NMR (200 MHz, CD₂Cl₂): δ 7.99 (br s, 1H, H₂), 7.37 (br d, J=7.9 Hz, 1H, H₇), 7.32 (m, 1H, H$_{4''}$), 7.17 (dd, J=7.3, 7.9 Hz, 1H, H₆), 7.03 (d, J=7.3 Hz, 1H, H₅), 6.96 (m, 2H, H$_{3'',5''}$), 5.40 (s, 2H, CH₂PhF₂), 2.59 (s, 3H, CH₃).

EXAMPLE 42

Preparation of 1-(2,6-Difluorobenzyl)-2-Formyl-4-Methylbenzimidazole

In this Example, 1-(2,6-difluorobenzyl)-2-formyl-4-methylbenzimidazole (50) was prepared according to Method D. Pyridine (3.4 mL) dissolved in CH₂Cl₂ (50 mL) was added to CrO₃ (2.20 g). After 15 min., 1-(2,6-difluorobenzyl)-2-hydroxymethyl-4-methylbenzimidazole (Example 40) dissolved in DMF was added to the mixture and stirred. After 20 m, the organic solution was decanted from a tarry black deposit. The organic solution was washed with 5% NaOH, 5% HCl, NaHCO₃ and NaCl, dried (Na₂SO₄), filtered, and concentrated. Purification by flash chromatography eluting with 2% MeOH/CH₂Cl₂ gave 0.55 g (1.92 mmol. 44% yield) of 1-(2,6-difluorobenzyl)-2-formyl-4-methylbenzimidazole (50) and 0.17 g (0.66 mmol, 15% yield) of 1-(2,6-difluorobenzyl)-4-methylbenzimidazole (49). ¹H-NMR (200 MHz, CD₃OD): δ 10.13 (s, 1H, CHO), 7.36–7.10 (cm, 4H, H$_{5,6,7,4''}$), 6.90 (m, 2H, H$_{3'',5''}$), 6.05 (s, 2H, Ch₂PhF₂), 2.66 (s, 3H, CH₃).

EXAMPLE 43

Figure 13:
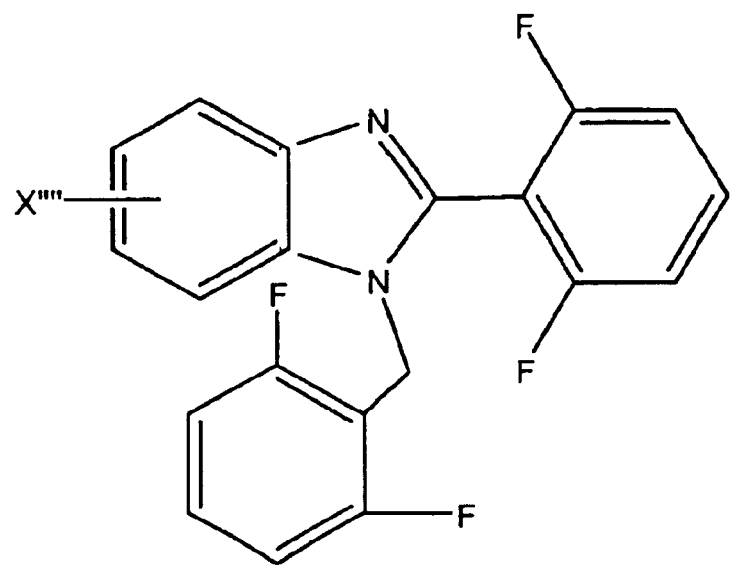
FIG. 13 shows the structure of substituted benzimidazoles of the present invention. Panel A describes 4-, 5-, 6-, or 7-substituted-1-(2,6-difluorobenzyl)-2-(2,6-difluorophenyl)benzimidazoles, while Panel B shows 4-substituted 1-(2,6-difluorobenzyl)-2-(2,6-difluorophenyl)benzimidazoles of the present invention.
Figure 13:
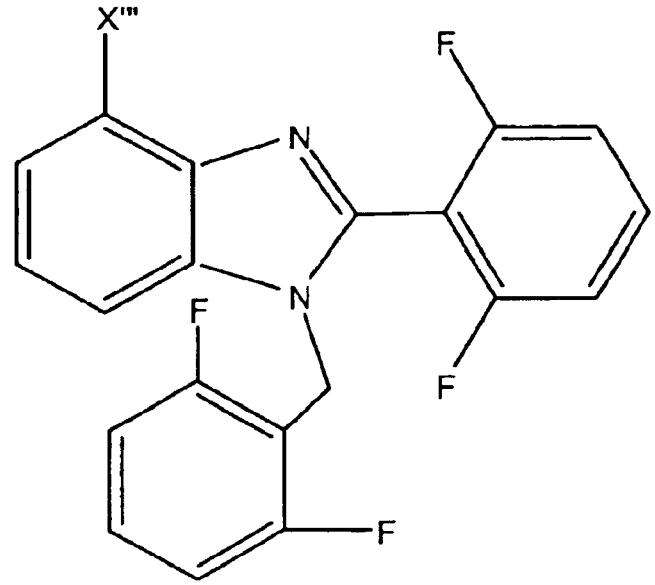

Preparation of 1-(2,6-Difluorobenzyl)-2-(2,6-Difluorophenyl)-4-cyanobenzimidazole This Example, and subsequent Examples provide 1-(2,6-difluorobenzyl)-2-(2,6-difluorophenyl)benzimidazole compositions with general structure of FIG. 13B.

In this example, 1-(2,6-difluorobenzyl)-2-(2,6-difluorophenyl)-4-cyanobenzimidazole (4007) was prepared in five steps from methyl N,N-bis(2,6-difluorobenzoyl)-6-nitro-2-anilidecarboxylate (4002). To methyl 2-amino-6-nitrobenzoate (4001) (12.75 g, 65.0 mmol) dissolved in THF:pyridine (1:1) (300 mL) was added 2,6-difluorobenzoyl chloride (18.0 mL, 142.7 mmol, 220 M %). After a second addition at 7 h of 2,6-difluorobenzoyl chloride (8.0 mL, 64 mmol, 100 M %) and stirring overnight at room temperature, the reaction was concentrated. The residue was suspended in water and filtered. The filtrate was then suspended in boiling methanol and filtered, yielding methyl N,N-bis(2,6-difluorobenzoyl)-6-nitro-2-anilidecarboxylate (4002) (28.26 g, 59.3 mmol, 91% yield): ¹H-NMR (200 MHz, DMSO-d₆) δ 8.41 (dd, J=1.5, 8.2 Hz, 1H, H₅), 8.29 (dd, J=1.5, 8.0 Hz, 1H, H₃), 7.86 (dd, J=8.0, 8.2 Hz, 1H, H₄), 7.55 (m, 2H, H$_{4',4''}$), 7.13 (m, 4H, H$_{3',5',3'5'}$),3.86 (s, 3H, CO₂Me).

To methyl N,N-bis(2,6-difluorobenzoyl)-6-nitro-2-anilidecarboxylate (4002) (28.20 g, 59.2 mmol) suspended in pyridine (300 mL) was added hydrazine (3.0 mL, 61.7 mmol, 105 M %). After 6 h at room temperature, the reaction was concentrated and the residue was redissolved in $CH_2Cl_2$, and washed with $NaHCO_3$ (sat. aq.), and NaCl (sat. aq.). The combined washings were dried ($Na_2SO_4$), filtered, and evaporated. Recrystallization of the crude product from MeOH yielded methyl N-(2,6-difluorobenzoyl)-6-nitro-2-anilidecarboxylate (4003) (18.31 g, 54.5 mmol, 92% yield): $^1$H-NMR (200 MHz,$CD_2Cl_2$) δ 10.81 (br, 1H, NH), 8.22 (dd, J=1.7, 8.1 Hz, 1H, $H_5$), 8.15 (dd, J=1.7, 8.1 Hz, 1H, $H_3$), 7.50 (m, 1H, $H_{4'}$), 7.42 (dd, J=8.1, 8.1 Hz, 1H, $H_4$), 7.05 (m, 2H, $H_{3',5'}$), 3.94 (s, 3H, $CO_2Me$).

Methyl N-(2,6-difluorobenzoyl)-6-nitro-2-anilidecarboxylate (4003) (19.33 g, 57.5 mmol) and iron powder (19.3 g) were reacted for 1 h. Recrystallization of the crude product from MeOH, yielded white solids of methyl 2-(2,6-difluorophenyl)benzimidazole-2-carboxylate (4004) (14.67 g, 50.9 mmol, 89% yield). $^1$H-NMR (300 MHz, $CD_2Cl_2$) δ 10.92 (br, 1H, NH), 8.06 (d, J=8.1 Hz,1H, $H_5$), 7.97 (1H, dd, J=1.0, 7.6 Hz, 1H, $H_7$), 7.49 (m, 1H, $H_{4'}$), 7.37 (dd, J=8.1, 7.6 Hz, 1H, $H_6$), 7.14 (m, 2H, $H_{3',5'}$), 4.01 (s, 3H, $CH_3$).

Methyl 2-(2,6-difluorophenyl)benzimidazole-2-carboxylate (4004) (16.15 g, 56.0 mmol) was reacted with 2,6-difluoro-a-bromo-toluene (14.67 g, 70.86 mmol, 125 M %). The crude product was purified by flash chromatography eluting with 2% MeOH/$CH_2Cl_2$, and recrystallization from diethylether, yielding white crystals of methyl 1-(2,6-difluorobenzyl)-2-(2,6-difluorophenyl)benzimidazole-2-carboxylate (4005) (17.63 g, 42.55 mmol, 76% yield). M.p. 185–186° C. $^1$H-NMR (200 MHz, $CD_2Cl_2$) δ 7.94 (dd, J=1.1, 7.6 Hz, 1H, $H_5$), 7.72 (dd, J=1.1, 8.2 Hz, 1H, $H_7$), 7.56 (m, 1H, $H_{4'}$), 7.37 (dd, J=7.6, 8.2 Hz, 1H, $H_6$), 7.26 (m, 1H, $H_{4''}$),7.09 (m,2H, $H_{3',5'}$), 6.82 (m, 2H, $H_{3'',5''}$), 5.39 (s, 2H, $CH_2PhF_2$), 3.95 (s, 3H, $CO_2CH_3$).

To methyl 1-(2,6-difluorobenzyl)-2-(2,6-difluorophenyl)benzimidazole-2-carboxylate (4005) (1.02 g, 2.46 mmol) dissolved in methanol (20 mL) was added barium hydroxide (1.20 g). After 2 h, acetic acid was added and the reaction concentrated. The residue was redissolved in $CH_2Cl_2$ and washed with $NaHCO_3$ (sat. aq.) and NaCl (sat. aq.). The combined washings were dried ($Na_2SO_4$), filtered and concentrated. The product was purified by flash chromatography eluting with 8% MeOH/$CH_2Cl_2$ and recrystallization from diethylether/hexane (3:1) gave white crystals of 1-(2, 6-difluorobenzyl)-2-(2,6-difluorophenyl)benzimidazole-2-carboxylate (4006) (0.71 g, 1.77 mmol, 72% yield). M.p. 179–180° C. $^1$H-NMR (200 MHz, $CD_2Cl_2$) δ 8.06 (d, J=7.8 Hz, 1H, $H_5$), 7.76 (d, J=8.1 Hz, 1H, $H_7$), 7.62 (m, 1H $H_{4'}$), 7.47 (dd, J=7.8, 8.1 Hz, 1H, $H_6$), 7.29 (m, 1H, $H_{4'}$), 7.14 (m,2H, $H_{3',5'}$), 6.85 (m, 2H, $H_{3'',5''}$), 5.45 (s, 2H, $CH_2PhF_2$).

To methyl 1-(2,6-difluorobenzyl)-2-(2,6-difluorophenyl)benzimidazole-2-carboxylate (4006) (2.00 g, 4.83 mmol) suspended in xylene (50 mL) was added a freshly prepared 1.0 M solution of $AlMe_2NH_2$ (7 mL, 7.00 mmol, 145 M %). After 45 min at reflux, the reaction was concentrated and then redissolved in $CH_2Cl_2$. The organic solution was washed with $NaHSO_4$ (10% solution, slow addition), $NaHCO_3$ (sat. aq) and NaCl (sat. aq). The combined washings were dried ($Na_2SO_4$), filtered and concentrated. The product was purified by flash chromatography eluting with 1% methanol/$CH_2Cl_2$ and recrystallization from diethylether, to produce white crystals of 1-(2,6-difluorobenzyl)-2-(2,6-difluorophenyl)-4-cyanobenzimidazole (4007) (1.50 g, 3.93 mmol, 81% yield). M.p. 153–155° C. $^1$H-NMR (200 MHz, $CD_2Cl_2$) δ 7.76 (dd, J=1.1, 8.6 Hz, 1H, $H_5$), 7.63 (dd, J=1.0, 7.6 Hz, 1H, $H_7$), 7.58 (m, 1H, $H_{4'}$),7.37 (dd, J=7.6, 8.6 Hz, 1H, $H_6$), 7.28 (m, 1H, $H_{4''}$), 7.11(m, 2H, $H_{3',5'}$), 6.83 (m, 2H, $H_{3'',5''}$), 5.40 (s, 2H, $CH_2PhF_2$).

EXAMPLE 44

Preparation of 1-(2,6-difluorobenzyl)-2-(2,6-difluorophenyl)-4-(propan-2-ol)benzimidazole To methyl 1-(2,6-difluorobenzyl)-2-(2,6-difluorophenyl) benzimidazole-2-carboxylate (4006, Example 43) (1.00 g, 2.41 mmol) dissolved in THF (20 mL) was added 3M methyl magnesium bromide (3.00 mL, 9.00 mmol). After 1 h, the reaction was concentrated. The residue was redissolved in $CH_2Cl_2$, and washed with $NaHCO_3$ (sat. aq.) and NaCl (sat. aq.). The combined washings were dried ($Na_2SO_4$), filtered and concentrated. The product was purified by flash chromatography eluting with 2% MeOH/$CH_2Cl_2$ and recrystallization from diethylether/hexane (3:1), yielding white crystals (0.95 g, 2.29 mmol, 95% yield). M.p. 149–150°C.; $^1$H-NMR (200 MHz, $CD_2Cl_2$) δ 7.55 (m, 1H, H4'), 7.40 (d, J=8.1 Hz, 1H, $H_5$), 7.25 (m, 2H, $H_{4'',6}$), 7.16 (dd, J=1.1, 7.6 Hz, 1H, $H_7$), 7.10 (m, 2H, $H_{3',5'}$), 6.82 (m, 2H, $H_{3'',5''}$), 5.82 (s, 1H, OH), 5.37 (s, 2H, $CH_2PhF_2$), 1.67 (s, 6H, iPr).

EXAMPLE 45

Preparation of 1-(2,6-difluorobenzyl)-2-(2,6-difluorophenyl)-4-(isopropenyl)benzimidazole To concentrated $H_2SO_4$ (1.00 mL) at room temperature was added 1-(2,6-difluorobenzyl)-2-(2,6-difluorophenyl)-4-(propan-2-ol)benzimidazole (Example 44) (0.45 g, 1.09 mmol). After 15 min, the reaction was diluted with ethylacetate. The organic solution was washed with $NaHCO_3$ (sat. aq.) and NaCl (sat. aq.). The combined washings were dried ($Na_2SO_4$), filtered and concentrated. The product was purified by flash chromatography eluting with 1% MeOH/$CH_2Cl_2$ and recrystallization from diethylether/hexane (3:1) to produce 0.11 g (0.28 mmol, 30% yield) of white crystals. M.p. 156–158°C. $^1$H-NMR (200 MHz, $CD_2Cl_2$) δ 7.53 (m, 1H, $H_{4'}$), 7.44–16 (m, 4H, $H_{4'',5,6,7}$), 7.07 (m, 2H, $H_{3',5'}$), 6.81 (m, 2H, $H_{3'',5''}$), 6.03 (dq, J=0.9, 2.4 Hz, 1H, vinyl), 5.36 (dq, J=1.5, 2.4 Hz, 1H, vinyl), 5.35 (s, 2H, $CH_2PhF_2$), 2.33 (dd, J=0.8, 1.5 Hz, 3H, $CH_3$).

EXAMPLE 46

Preparation of 1-(2,6-Difluorobenzyl)-2-(2,6-Difluorophenyl)-4-methoxylbenzimidazole In this Example, 1-(2,6-difluorobenzyl)-2-(2,6-difluorophenyl)-4-methoxylbenzimidazole (5006) was prepared in four steps from 2-methoxyl-6-nitroaniline (5002). To 2-amino-3-nitrophenol (5001) (2.00 g, 12.98 mmol) dissolved in acetone (20 mL) was added $K_2CO_3$ (2.15 g), and methyl iodide (1.00 mL). After stirring overnight, the reaction was concentrated. The residue was redissolved in ethylacetate, and washed with water, $NaHSO_4$(10% solution), NaCl (sat. aq.). The combined washings were dried ($Na_2SO_4$), filtered, and concentrated. The crude product was purified by flash chromatography eluting with (1:4) ethylacetate/hexane, yielding white crystals of 2-methoxyl-6-nitroaniline (5002) (1.79 g, 10.65 mmol, 82% yield). $^1$H-NMR (300 MHz, $CD_2Cl_2$) δ 7.69 (dd, J=1.4, 8.9 Hz, 1H, $H_5$), 6.92 (dd, J=1.4, 7.8 Hz, 1H, $H_3$), 6.62 (dd, J=8.9, 7.8 Hz, 1H, $H_4$), 6.42 (br, 2H, $NH_2$), 3.91 (s, 3H, $OCH_3$).

To 2-methoxyl-6-nitroaniline (5002) (13.75 g, 81.8 mmol) dissolved in THF:pyridine (1:1) (300 mL) was added 2,6-difluorobenzoyl chloride (22.0 mL, 174.4 mmol, 215 M %. After stirring the reaction mixture overnight at room temperature, the reaction was concentrated to dryness. The residue was redissolved in $CH_2Cl_2$, washed with $NaHCO_3$ (sat. aq.) and NaCl (sat. aq.). The combined washings were dried ($Na_2SO_4$), filtered and concentrated. The product was recrystallized from methanol to give white crystals of N,N-Bis-(2,6-difluorobenzoyl)-2-methoxyl-6-nitroanilide (5003) (33.7 g, 75.2 mmol, 92% yield). $^1$H-NMR (300 MHz, $CD_2Cl_2$) δ 7.70 (dd, J=1.4, 8.4 Hz, 1H, $H_5$), 7.48 (dd, J=8.4, 8.4 Hz, 1H, $H_4$), 7.35 (2H, m, $H_{4',4'}$), 7.15 (dd, J=1.4, 8.4 Hz, 1H, $H_3$), 6.87 (m, 4H, $H_{3',5',3',5'}$), 3.85 (s, 3H, $OCH_3$).

To N,N-bis-(2,6-difluorobenzoyl)-2-methoxyl-6-nitroanilide (5003) (33.7 g, 75.2 mmol) dissolved in pyridine (500 mL) was added hydrazine (4.50 mL, 92.6 mmol, 120 M %). After stirring overnight at room temperature, the reaction was concentrated. The residue was redissolved in $CH_2Cl_2$, and washed with $NaHCO_3$ (sat. aq.) and NaCl (sat. aq.). The combined washings were dried ($Na_2SO_4$), filtered, evaporated. The crude product was recrystallized from methanol, yielding white solids of N-(2,6-difluorobenzoyl)-2-methoxyl-6-nitroanilide (5004) (22.39 g, 72.6 mmol, 96% yield). $^1$H-NMR (200 MHz, $CD_2Cl_2$): δ 8.82 (br, 1H, NH), 7.51 (dd, J=1.6, 8.1 Hz, 1H, $H_5$), 7.45 (m, 1H, $H_4$), 7.35 (dd, J=8.2, 8.3 Hz, 1H, $H_4$), 7.12 (dd, J=8.3, 1.6 Hz, 1H, $H_3$), 7.01 (m, 2H, $H_{3',5'}$), 3.92 (s, 3H, OMe).

N-(2,6-difluorobenzoyl)-2-methoxyl-6-nitroanilide (5004) (2.20 g, 7.15 mmol) and iron powder (2.20 g) were reacted for 1 h. The crude product was purified by flash chromatography with 2% $MeOH/CH_2Cl_2$, yielding white crystals of 2-(2,6-difluorophenyl)-4-methoxylbenzimidazole (5005) (1.68 g, 6.18 mmol, 86% yield). $^1$H-NMR (300 MHz, $CD_2Cl_2$): δ 10.07 (br d, J=36 Hz, 1H, NH), 7.40 (cm, 1H), 7.29–7.00 (cm, 4H), 6.75 (dd, J=8.0, 13.8 Hz, 1H), 4.00 (d, J=4.2 Hz, 3H, $OCH_3$).

2-(2,6-Difluorophenyl)-4-methoxylbenzimidazole (5005) (1.25 g, 4.80 mmol) was reacted with 2,6-difluoro-a-bromotoluene (1.30 g, 6.28 mmol, 130 M %). The crude product was purified by flash chromatography eluting with 2% $MeOH/CH_2Cl_2$ and recrystallization from diethylether/hexane (3:1), yielding white crystals of 1-(2,6-difluorobenzyl)-2-(2,6-difluorophenyl)-4-methoxylbenzimidazole (5006) (1.68 g, 4.35 mmol, 91% yield). M.p. 154–155° C. $^1$H-NMR (200 MHz, $CD_2Cl_2$): δ 7.52 (m, 1H, $H_4$), 7.25 (m, 1H, $H_{4''}$), 7.19 (dd, J=7.8, 1.0 Hz, 1H, $H_5$), 7.13–7.00 (m, 3H, $H_{3',5',6}$), 6.81 (m, 2H, $H_{3'',5''}$), 6.72 (dd, J=7.8, 1.0 Hz, $H_7$), 5.33 (s, 2H, $CH_2PhF_2$), 4.00 (s, 3H, $OCH_3$).

EXAMPLE 47

Preparation of 1-(2,6-Difluorobenzyl)-2-(2,6-Difluorophenyl)-4-ethylbenzimidazole In this Example, 1-(2,6-difluorobenzyl)-2-(2,6-difluorophenyl)-4-ethylbenzimidazole (4011) was prepared in two steps from N-(2,6-difluorobenzoyl)-2-ethyl-6-nitroanilide (4009). 2-Ethyl-6-nitroaniline (4008) (3.10 g, 18.65 mmol) was reacted with 2,6-difluorobenzoyl chloride (3.50 mL, 27.83 mmol, 150 M %), and the reaction mixture was stirred overnight at room temperature. The crude product was purified by flash chromatography with 2% MeOH/$CH_2Cl_2$ and recrystallization from ethylacetate/hexane (1:4), yielding N-(2,6-difluorobenzoyl)-2-ethyl-6-nitroanilide (2.34 g, 7.64 mmol, 41% yield). $^1$H-NMR (200 MHz, $CD_2Cl_2$) δ 8.25 (br, 1H, NH), 7.85 (dd, J=1.7, 8.1 Hz, 1H, $H_5$), 7.66 (dd, J=1.7, 7.9 Hz, 1H, $H_3$), 7.49 (m, 1H, $H_4$), 7.45 (dd, J=7.9, 8.1 Hz, 1H, $H_4$), 7.06 (m, 2H, $H_{3',5'}$), 2.81 (q, J=7.6 Hz, 2H, $CH_2$), 1.29 (t, J=7.6 Hz, 3H, $CH_3$).

N-(2,6-Difluorobenzoyl)-2-ethyl-6-nitroanilide (4009) (2.00 g, 6.53 mmol) was reacted with iron powder (2.00 g) for 0.5 h at room temperature. The crude product was purified by flash chromatography eluting with 2% MeOH/$CH_2Cl_2$, and recrystallization from $CH_2Cl_2$, yielding white crystals of 2-(2,6-difluorophenyl)-4-ethylbenzimidazole (4010) (1.65 g, 6.39 mmol, 98% yield). $^1$H-NMR (200 MHz, $CD_2Cl_2$): δ 9.78 (br, 1H, NH), 7.46 (br, 1H, $H_5$), 7.45 (m, 1H, $H_4$), 7.23 (dd, J=7.4, 7.9 Hz, 1H, $H_6$), 7.17–7.04 (m, 3H, $H_{3',5',7}$), 3.03 (br, 2H, $CH_2$), 1.39 (t, J=7.7 Hz, 3H, $CH_3$).

2-(2,6-Difluorophenyl)-4-ethylbenzimidazole (4010) (0.70 g, 2.71 mmol) was reacted with 2,6-difluoro-a-bromotoluene (0.72 g, 3.48 mmol, 130 M %). The crude product was purified by flash chromatography eluting with 2% MeOH/$CH_2Cl_2$ and recrystallization from diethylether/hexane (3:1), yielding white crystals of 1-(2,6-Difluorobenzyl)-2-(2,6-difluorophenyl)-4-ethylbenzimidazole (4011) (0.79 g, 2.06 mmol, 76% yield). M.p. 165–166° C. $^1$H-NMR (200 MHz, $CD_2Cl_2$): δ 7.53 (m, 1H, $H_4$), 7.32 (d, J=8.2 Hz, 1H, $H_5$), 7.29–7.16 (m, 2H, $H_{6,4''}$), 7.14–7.01 (m, 1H, $H_7$), 7.07 (m, 2H, $H_{3'',5''}$), 6.81 (m, 2H, $H_{3'',5''}$), 5.33 (s, 2H, $CH_2$), 3.07 (q, J=7.6 Hz, 2H, $CH_2$), 1.35 (t, J=7.6 Hz, 3H, $CH_3$).

EXAMPLE 48

Preparation of 1-(2,6-Difluorobenzyl)-2-(2,6-Difluorophenyl)-4-(N-methylamino)benzimidazole First, 1-(2,6-difluorobenzyl)-2-(2,6-difluorophenyl)-4-(N-methylacetamido)benzimidazole (4005) was prepared (Example 88). To 1-(2,6-difluorobenzyl)-2-(2,6-difluorophenyl)-4-acetamido)benzimidazole (2.44 g, 5.90 mmol) and methyl iodide (0.60 mL, 9.69 mmol) dissolved in THF (30 mL) was added excess NaH. After stirring overnight, the solution was concentrated to dryness, diluted with $CH_2Cl_2$, and washed with water, $NaHSO_4$ (10% solution) and NaCl (sat. aq.). The combined washings were dried ($Na_2SO_4$), filtered, concentrated and purified by flash chromatography eluting with 2% methanol in $CH_2Cl_2$ to give 1-(2,6-difluorobenzyl)-2-(2,6-difluorophenyl)-4-(N-methylacetamido)benzimidazole (0.89 g, 2.08 mmol, 63% yield). M.p. 155–156° C. $^1$H-NMR (200 MHz, $CD_2Cl_2$) δ 7.55 (m, 1H, $H_4$), 7.48 (br d, J=7.4 Hz, 1H, $H_5$), 7.31 (dd, J=7.4, 7.7 Hz, 1H, $H_6$), 7.27 (m, 1H, $H_{4''}$), 7.14 (dd, J=1.1, 7.7 Hz, 1H, $H_7$), 7.09 (m, 2H, $H_{3',5'}$), 6.84 (m, 2H, $H_{3'',5''}$), 5.38 (s, 2H, $CH_2PhF_2$), 3.34 (s, 3H, $NCH_3$), 1.83 (s, 3H, NAc).

To 1-(2,6-difluorobenzyl)-2-(2,6-difluorophenyl)-4-(N-methylacetamido)benzimidazole (4005) (0.50 g, 1.17 mmol) suspended in water (9.0 mL) was added HCl (1.0 mL). After 3 h at reflux, the solution was concentrated to dryness, diluted with ethylacetate, and washed with $NaHCO_3$ (sat. aq.) and NaCl (sat. aq.). The combined washings were dried ($Na_2SO_4$), filtered, concentrated. The crude product was purified by flash chromatography eluting with 2% methanol in $CH_2Cl_2$, yielding 1-(2,6-difluorobenzyl)-2-(2,6-difluorophenyl)-4-(N-methylamino)benzimidazole (4006) (0.35 g, 78% yield):. M.p. 194–195° C. $^1$H-NMR (200 MHz, $CD_2Cl_2$) δ 7.52 (m, 1H, $H_4$), 7.23 (m, 1H, $H_{4''}$), 7.13 (dd, J=8.3, 8.0 Hz, 1H, $H_6$), 7.07 (m, 2H, $H_{3',5'}$), 6.80 (m, 2H, $H_{3'',5''}$), 6.76 (d, J=8.3 Hz, 1H, $H_5$), 6.36 (d, J=8.0 Hz, 1H, $H_7$), 5.29 (s, 2H, $CH_2PhF_2$), 2.96 (s, 3H, $NCH_3$).

EXAMPLE 49

Preparation of 1-(2,6-Difluorobenzyl)-2-(Cyclopropyl)-4-Methoxylbenzimidazole

In this Example, 1-(2,6-difluorobenzyl)-2-(cyclopropyl)-4-methoxylbenzimidazole (5016) was prepared in two steps from cyclopropanecarboxylic acid (2-methoxy-6-nitrophenyl)-amide (5013). To 2-methoxyl-6-nitroaniline (5002) (4.15 g, 24.7 mmol) dissolved in THF:pyridine (1:1) (100 mL) was added cyclopropanecarbonyl chloride (2.7 mL, 29.8 mmol, 120 M %). After stirring at room temperature for 4 h, the reaction was concentrated to dryness and the residue was redissolved in $CH_2Cl_2$, and washed with $NaHSO_4$ (10% solution), $NaHCO_3$ (sat. aq) and NaCl (sat. aq.). The combined washings were dried ($Na_2SO_4$), filtered and concentrated. Cyclopropanecarboxylic acid (2-methoxyl-6-nitrophenyl)-amide (5013) was recrystallized from methanol (4.90 g, 20.8 mmol, 84% yield of white crystals). $^1$H-NMR (200 MHz, $CD_2Cl_2$): δ 7.82 (br, 1H, NH), 7.44 (dd, J=1.6, 8.1 Hz, 1H, $H_5$), 7.25 (dd, J=8.2, 8.1 Hz, 1H, $H_4$), 7.16 (dd, J=1.7, 8.2 Hz, 1H, $H_3$), 3.95 (s, 3H, $OCH_3$), 1.65 (m, 1H), 0.94 (m, 4H).

Cyclopropanecarboxylic acid (2-methoxy-6-nitrophenyl)-amide (5013) (7.80 g, 33.1 mmol) and iron powder (7.60 g) were suspended in acetic acid (200 mL) for 25 min at reflux. The reaction was concentrated and redissolved in ethyl acetate, and washed with $NaHCO_3$ (sat. aq) and NaCl (sat. aq). The combined washings were dried ($Na_2SO_4$), filtered and concentrated. The crude product was purified by flash chromatography with 2% $MeOH/CH_2Cl_2$ and recrystallization from diethyl ether/hexane (3:1), yielding white crystals of 2-(cyclopropyl)-4-methoxylbenzimidazole (5014) (4.90 g, 26.1 mmol, 79% yield). $^1$H-NMR (200 MHz, $CD_2Cl_2$:) δ 7.07 (cm, 2H), 6.65 (cm, 1H), 3.90 (s, 3H, $OCH_3$), 2.17–2.03 (m, 1H), 1.22–0.96 (m, 4H).

2-(Cyclopropyl)-4-methoxylbenzimidazole (1.00 g, 5.32 mmol) (5014) was reacted with 2,6-difluoro-a-bromotoluene (1.30 g, 6.28 mmol, 130 M %). The crude product was purified by flash chromatography eluting with 2% methanol/$CH_2Cl_2$ and recrystallization from diethylether/hexane (3:1), yielding white crystals of 1-(2,6-Difluorobenzyl)-2-(cyclopropyl)-4-methoxylbenzimidazole (5016) (1.54 g, 4.90 mmol, 92% yield). M.p. 136–139° C. $^1$H-NMR (200 MHz, $CD_2Cl_2$) δ 7.31 (m, 1H, $H_{4'}$), 7.07 (dd, J=8.0, 7.8 Hz, 1H, $H_6$), 6.94 (m, 3H, $H_{3',5',5}$), 6.61 (dd, J=7.8, 1.0 Hz, $H_7$), 5.46 (s, 2H, $CH_2PhF_2$), 3.95 (s, 3H, $OCH_3$), 2.20×2.03 (m, 1H), 1.18–0.97 (m, 4H).

EXAMPLE 50

Preparation of 1-(2,6-Difluorobenzyl)-2-(2-Fluoro-6-Methoxylphenyl)-4-Nitrobenzimidazole First, 2-(2,6-difluorophenyl)-4-nitrobenzimidazole was prepared. N-(2,6-difluorobenzoyl)-2-amino-3-nitroanilide (Example 5) was dissolved in acetic acid (150 mL) and heated to reflux. After heating overnight, the reaction mixture was cooled to room temperature, and concentrated. The residue was redissolved in methylene chloride, washed with $NaHCO_3$ (sat. soln.). The combined washings were dried with $Na_2SO_4$, filtered and evaporated. The crude product was purified by flash chromatography eluting with ethylacetate/hexane (1:1), and recrystallized from ethylacetate/hexane (1:4), yielding the 2-(2,6-difluorophenyl)-4-nitrobenzimidazole (7.90 g, 2.87 mmol, 72%). $^1$H NMR (300 MHz, $CD_2Cl_2$): 11.00 (s, 1H, NH), 8.23 (dd, J=8.2, 0.8 Hz, 1H, $H_5$), 8.21 (dd, J=8.0, 0.8 Hz, 1H, $H_7$), 7.54 (m, 1H, $H_4$), 7.45 (dd, J=8.0, 8.2 Hz, 1H, $H_6$), 7.13 (m, 2H, $H_{3',5'}$).

2-(2,6-difluorophenyl)-4-nitrobenzimidazole (7.7 g, 28 mmol) was reacted with 2,6-difluorobenzylbromide (6.95 g, 33.6 mmol). The crude product was purified by recrystallization from diethylether:hexane (3:1), 9.8 g (24.4 mmol, 87%), yielding white crystals 1-(2,6-difluorobenzyl)-2-(2,6-difluorophenyl)-4-nitrobenzimidazole. M.p. 168–170° C. $^1$H-NMR (300 MHz, $CD_2Cl_2$): δ 8.13 (dd, J=8.1, 0.9 Hz, 1H, $H_5$), 7.86 (dd, J=8.1, 0.9 Hz, 1H, $H_7$), 7.59 (m, 1H, $H_{4'}$), 7.43 (dd, J=8.1 Hz, $H_6$), 7.28 (m, 1H, $H_{4''}$), 7.12 (m, 2H, $H_{3'',5''}$), 6.84 (m, 2H, $H_{3'',5''}$), 5.44 (s, 2H, $CH_2$).

To 1-(2,6-difluorobenzyl)-2-(2,6-difluorophenyl)-4-nitrobenzimidazole (2.00 g, 8 mmol)was added 2,6-difluorobenzylbromide (2.0.2 g, 9.76 mmol, 130 M %) dissolved in THF (20 mL) was added NaH (0.84 g, 21 mmol, 290 M %). After 8 h, the reaction was quenched with m ethanol and concentrated. The residue was dissolved in $CH_2Cl_2$, and washed with water and NaCl (sat. aq.). The combined washings were dried ($Na_2SO_4$), filtered, concentrated. The crude product was purified by flash chromatography eluting with ethylacetate:hexane (1:1) (2.33 g, 5.64 mmol, 78%). M.p. 189–192° C. $^1$H-NMR (200 MHz, $CD_2Cl_2$) δ 8.11 (dd, J=8.1, 1.0 Hz, 1H, $H_5$), 7.84 (dd, J=8.1, 1.0 Hz, 1H, $H_7$), 7.52 (m, 1H, $H_{4'}$), 7.40 (dd, J=8.1 Hz, 1H, $H_6$), 7.26 (m, 1H, $H_{4''}$), 6.89–6.74 (m, 4H, $H_{3',5',3'',5''}$), 5.36 (d, J=3.4 Hz, 2H, $CH_2PhF_2$ (rotamers)), 3.73 (s, 3H, $OCH_3$).

EXAMPLE 51

Preparation of 1-(2,6-Difluorobenzyl)-2-(2-Fluoro-4-Methoxylphenyl)-4-Aminobenzimidazole To 1-(2,6-difluorobenzyl)-2-(2-fluoro-4-methoxylphenyl)-4-nitrobenzimidazole (Example 50) (2.00 g, 4.98 mmol) dissolved in acetic acid (20 mL) was added $SnCl_2x2H_2O$ (9.02 g) dissolved in concentrated HCl (8 mL). After stirring for 30 min at room temperature, the mixture was concentrated. The residue was diluted with $CH_2Cl_2$ and washed with $NaHCO_3$ (sat. aq.) and NaCl (sat. aq.). The combined washings were dried ($Na_2SO_4$), filtered, and evaporated. The crude product was recrystallized from methanol to give 3.26 g of white crystals, (8.78 mmol, 70% yield). M.p. 200–202° C. $^1$H-NMR (200 MHz, $CD_2Cl_2$) δ 7.45 (m, 1H, $H_{4'}$), 7.22 (m, 1H, $H_{4''}$), 7.05 (dd, J=7.8, 7.6 Hz, 1H, $H_6$), 6.85–6.72 (m, 5H, $H_{3'',5''}$), 6.50 (dd, J=7.7, 1.0 Hz, 1H, $H_5$), 5.21 (d, J=5.4 Hz, 2H, $CH_2PhF_2$ (rotamers)), 4.34 (br, 2H, $NH_2$), 3.72 (s, 3H, $OCH_3$).

EXAMPLE 52

Preparation of 1-Benzyl-2-(2,6-Difluorophenyl)-4-Methoxylbenzimidazole 2-(2,6-Difluorophenyl)-4-methoxylbenzimidazole (5005, Example 46) (2.02 g, 7.77 mmol) was reacted with benzyl bromide (1.20 mL, 10.1 mmol, 130 M %). The crude product was purified by flash chromatography eluting with 2% MeOH/ $CH_2Cl_2$ and recrystallization from diethylether/hexane (3:1), yielding white crystals of 1-benzyl-2-(2.6-difluorophenyl)-4-methoxylbenzimidazole (2.47 g, 7.05 mmol, 90% yield). M.p. 139–141° C. $^1$H-NMR (200 MHz, $CD_2Cl_2$) δ 7.48 (m, 1H, $H_{4'}$), 7.25–6.96 (m, 8H), 6.86 (dd, J=0.8, 8.3 Hz, 1H, $H_5$), 6.72 (dd, J=8.0, 0.8 Hz, 1H, $H_7$), 5.24 (s, 2H, $CH_2Ph$), 4.01 (s, 3H, $OCH_3$).

EXAMPLE 53

Preparation of 1-(Ethylbenzyl)-2-(2,6-Difluorophenyl)-4-methoxylbenzimidazole 2-(2,6-Difluorophenyl)-4-methoxylbenzimidazole (5005, Example 46) (0.10 g, 0.38 mmol) was reacted with (1-bromoethyl)benzene (0.28 mL). The crude product was purified by flash chromatography eluting with 2% MeOH/

$CH_2Cl_2$ and recrystallization from diethylether/hexane (3:1), yielding white crystals of 1-(ethylbenzyl)-2-(2,6-difluorophenyl)-4-methoxylbenzimidazole (0.12 g, 0.33 mmol, 86% yield). M.p. 139–141° C. $^1$H-NMR (200 MHz, $CD_2Cl_2$) δ 7.51 (m, 1H, $H_{4''}$), 7.25 (dd, J=8.0, 8.1 Hz, 1H, $H_6$), 7.17 (m, 3H, Ph), 7.06 (m, 2H, $H_{3'',5''}$), 7.04 (dd, J=8.1 Hz, 0.8 Hz, 1H, $H_5$), 6.91 (m, 2H, Ph), 6.74 (dd, J=0.8, 8.0 Hz, $H_7$), 4.27 (t, J=7.5 Hz, 2H), 4.03 (s, 3H, $OCH_3$), 3.00 (t, J=7.5 Hz, $CH_2Ph$).

EXAMPLE 54

Preparation of 1-(3,3-Dimethylallyl)-2-(2,6-Difluorophenyl)-4-Methoxylbenzimidazole To 2-(2,6-difluorophenyl)-4-methoxylbenzimidazole (5005, Example 46) (0.28 g, 1.08 mmol) and 3,3-dimethylallyl bromide (0.20 mL, 0.26 mmol, 160 M %) dissolved in THF (3 mL) was added NaH (60% dispersion in mineral oil) (0.15 g, 3.75 mmol, 350 M %). After 4 h, the reaction was quenched with MeOH and concentrated. The residue was redissolved in dichloromethane, washed with water and NaCl (sat. aq.), dried ($Na_2SO_4$), filtered and concentrated. The product was purified by flash chromatography eluting with 2% $MeOH/CH_2Cl_2$ and recrystallized from hexane to give white powders of 1-(3,3-dimethylallyl)-2-(2,6-difluorophenyl)-4-methoxyl-benzimidazole (0.30 g, 0.91 mmol, 84% yield). M.p. 101–103° C. $^1$H-NMR (200 MHz, $CD_2Cl_2$): 7.52 (m, 1H, $H_{4''}$), 7.24 (dd, J=7.9, 8.2 Hz, 1H, $H_6$), 7.08 (m, 2H, $H_{3'',5''}$), 7.02 (dd, J=0.9, 8.2 Hz, 1H, $H_5$), 6.73 (dd, J=0.9, 7.9 Hz, 1H, $H_7$), 5.19 (t, J=7.0 Hz, 1H, $H_{2'}$), 4.02 (s, 3H, $OCH_3$), 4.62 (d, J=7.0 Hz, 2H, $H_{1'}$), 1.64 (s, 3H, $CH_3$), 1.58 (s, 3H, $CH_3$).

EXAMPLE 55

Preparation of 1-(3,3-Dimethylallyl)-2-(2,6-difluorophenyl)-4-methylbenzimidazole To 2-(2,6-difluorophenyl)-4-methylbenzimidazole (Example 13) (0.50 g, 2.05 mmol) and 3,3-dimethylallyl bromide (0.50 mL, 4.34 mmol, 210 M %) dissolved in THF (10 mL) was added NaH (60% dispersion in mineral oil) (0.17 g, 4.25 mmol, 200 M %). After 4 h, the reaction was quenched with MeOH and concentrated. The residue was redissolved in dichloromethane, washed with water and NaCl (sat. aq.), dried ($Na_2SO_4$), filtered and concentrated. The product was purified by flash chromatography eluting with 2% $MeOH/CH_2Cl_2$ and recrystallized from hexane to yield white powders of 1-(3,3-dimethylallyl)-2-(2,6-difluorophenyl)-4-methylbenzimidazole (0.40 g, 1.28 mmol, 63% yield). M.p. 78–79° C. $^1$H-NMR (200 MHz, $CD_2Cl_2$): 7.52 (m, 1H, $H_{4''}$), 7.26–7.02 (m, 5H, $H_{5,6,7,3'',5''}$), 5.18 (t, J=6.8 Hz, 1H, $H_{2'}$), 4.62 (d, J=6.8 Hz, 2H, $H_{1'}$), 2.64 (s, 3H, $CH_3$), 1.64 (s, 3H, $CH_3$), 1.57 (s, 3H, $CH_3$).

EXAMPLE 56

Preparation of 1-(3,3-Dimethylallyl)-2-(2,6-difluorophenyl)-4-nitrobenzimidazole To 2-(2,6-difluorophenyl)-4-nitrobenzimidazole (Example 50) (2.50 g, 9.08 mmol) and 3,3-dimethylallyl bromide (2.00 mL, 17.35 mmol, 190 M %) dissolved in THF (25 mL) was added NaH (60% dispersion in mineral oil) (0.70 g, 17.5 mmol, 190 M %). After stirring overnight at room temperature, the reaction was quenched with MeOH and concentrated. The residue was redissolved in dichloromethane, washed with water and NaCl (sat. aq.), dried ($Na_2SO_4$), filtered and concentrated. The product was purified by flash chromatography eluting with ethylacetate/hexane (1:1) and recrystallized from hexane (2.88 g, 8.39 mmol, 92% yield of white powder). mp 130–132° C.; $^1$H-NMR (200 MHz, $CD_2Cl_2$): 8.15 (dd, J=1.0, 8.1 Hz, 1H, $H_5$), 7.77 (dd, J=1.0, 8.2 Hz, 1H, $H_7$), 7.59 (m, 1H, $H_{4''}$), 7.44 (dd, J=8.1, 8.2 Hz, 1H, $H_6$), 7.14 (m, 2H, $H_{3'',5''}$), 5.19 (t, J=6.8 Hz, 1H, $H_{2'}$), 4.73 (d, J=7.0 Hz, 2H, $H_{1'}$), 1.68 (s, 3H, $CH_3$), 1.62 (s, 3H, $CH_3$).

EXAMPLE 57

Preparation of 1-(3,3-Dimethylallyl)-2-(2,6-difluorophenyl)-4-aminobenzimidazole To 1-(3,3-dimethylallyl)-2-(2,6-difluorophenyl)-4-nitrobenzimidazole (Example 56) (2.00 g, 5.83 mmol) dissolved in glacial acetic acid (20 mL) was added iron powder (8.89 g). After 30 min at reflux, the reaction was concentrated to dryness, diluted with ethyl acetate and washed with $NaHCO_3$. The aqueous layer was back extracted with ethyl acetate, and the combined organic solution was washed with $NaHCO_3$ (sat. aq.) and NaCl (sat. aq.), dried ($Na_2SO_4$), filtered and concentrated. The product was purified by flash chromatography eluting with 4% $MeOH/CH_2Cl_2$ and recrystallized from hexane (1.73 g, 5.52 mmol, 95% yield of white powder). M.p. 107–108° C. $^1$H-NMR (200 MHz, $CD_2Cl_2$): 7.54 (m, 1H, $H_{4''}$), 7.16–7.05 (m, 3H, $H_{6,3'',5''}$), 6.80 (dd, J=1.0, 8.2 Hz, 1H, $H_7$), 6.55 (dd, J=1.0, 7.6 Hz, 1H, $H_5$), 5.20 (t, J=6.8 Hz, 1H, $H_{2'}$), 4.60 (d, J=6.8 Hz, 2H, $H_{1'}$), 4.40 (br, 2H, $NH_2$), 1.66 (s, 3H, $CH_3$), 1.58 (s, 3H, $CH_3$).

EXAMPLE 58

Preparation of N,N-Bis-(2,6-Difluorobenzoyl)-4-Chloro-2-Nitroanilide

In this Example, N,N-bis-(2,6-difluorobenzoyl)-4-chloro-2-nitroanilide (400) was prepared. First, 4-chloro-2-nitroaniline (1.05 g, 6.08 mmol) was dissolved in THF:pyridine (1:1) (20 mL), and 2,6-difluorobenzoyl chloride (7) was added (1.9 mL, 15.1 mmol, 250 M %). After 6 hours of mixing, a second aliquot of 2,6-difluorobenzoyl chloride (0.6 mL, 4.77 mmol, 78 M %) was added. After stirring overnight at room temperature, the reaction was concentrated to dryness. The residue was redissolved in $CH_2Cl_2$, washed with $NaHCO_3$ (sat. aq.) and NaCl (sat. aq.). The combined washings were dried ($Na_2SO_4$), filtered and concentrated. The product was recrystallized from ethylacetate (2.67 g, 5.90 mmol, 97% yield) to produce white crystals. $^1$H-NMR (300 MHz, $CD_2Cl_2$): δ 8.15 (d, J=2.4 Hz, 1H, $H_3$), 7.67 (dd, J=2.4, 8.5 Hz, 1H, $H_5$), 7.51 (d, J=8.5 Hz, 1H, $H_6$), 7.36 (m, 2H, $H_{4',4''}$), 6.89 (m, 4H, $H_{3',5',3'',5''}$).

EXAMPLE 59

Preparation of N-(2,6-Difluorobenzoyl)-4-Chloro-2-Nitroanilide

In this Example, N-(2,6-difluorobenzoyl)-4-chloro-2-nitroanilide (500) was prepared. First, N,N-bis-(2,6-difluorobenzoyl)-4-chloro-2-nitroanilide (Example 58) (1.00 g, 4.42 mmol) was dissolved in methanol/dioxane (1:1) (40 mL), and sodium hydroxide (0.27 g, 6.75 mmol, 150 M %) was then added to the mixture. After stirring for 30 minutes at room temperature, the reaction was quenched with $NaHSO_4$, diluted with $CH_2Cl_2$, and washed with $NaHCO_3$ (sat aq) and NaCl (sat aq). The combined washings were dried ($Na_2SO_4$), filtered and concentrated. The product (1.28 g, 4.09 mmol, 93% yield) was recrystallized from ethylene oxide/hexane (3:1). $^1$H-NMR (300 MHz, CD$_2$Cl$_2$): δ 10.72 (s, 1H, NH), 8.91 (d, J=9.1 Hz, 1H, H$_6$), 8.27 (d, J=2.5 Hz, 1H, H$_3$), 7.71 (dd, J=9.1, 2.5 Hz, 1H, H$_5$), 7.52 (m, 1H, H$_{4'}$), 7.08 (m, 2H, H$_{3',5'}$).

EXAMPLE 60

Preparation of N,N-Bis-(2,6-Difluorobenzoyl)-5-Chloro-2-Nitroanilide

In this Example, N,N-bis-(2,6-difluorobenzoyl)-5-chloro-2-nitroanilide (600) was prepared. First, 5-chloro-2-nitroaniline (1.02 g, 5.91 mmol) was dissolved in pyridine/THF (1:1) (20 mL), and 2,6-difluorobenzoyl chloride (7) (1.50 mL, 11.9 mmol, 200 M %) was then added. After stirring overnight at room temperature, the reaction was concentrated to dryness. The residue was redissolved in CH$_2$Cl$_2$, and washed with NaHCO$_3$ (sat. aq.) and NaCl (sat. aq.). The combined washings were dried (Na$_2$SO$_4$), filtered, and concentrated. The product was recrystallized from ethylacetate (2.50 g, 5.52 mmol, 93% yield of white crystals). $^1$H-NMR (300 MHz, CD$_2$Cl$_2$): δ 8.12 (dd, J=8.5, 1.1 Hz, 1H, H$_3$), 7.58 (AB, J=2.4, 1.1 Hz, 1H, H$_6$), 7.57 (AB, J=2.4, 8.4 Hz, 1H, H$_4$), 7.36 (m, 2H, H$_{4',4''}$), 6.89 (m, 4), H$_{3'5',3'',5''}$).

EXAMPLE 61

Preparation of N-(2,6-Difluorobenzoyl)-5-Chloro-2-Nitroanilide

In this Example, N-(2,6-difluorobenzoyl)-5-chloro-2-nitroanilide (700) was prepared. First, N,N-bis-(2,6-difluorobenzoyl)-5-chloro-2-nitroanilide (Example 60) (1.00 g, 2.20 mmol) was dissolved in methanol/dioxane (1:1) (20 mL), and then sodium hydroxide (92 mg, 2.30 mmol, 105 M %) was added. After stirring for 30 minutes at room temperature, additional sodium hydroxide (92 mg, 2.30 mmol, 105 M %) was added. After an additional 15 minutes the reaction was quenched with NaHSO$_4$, diluted with CH$_2$Cl$_2$, and washed with NaHCO$_3$ (sat aq.) and NaCl (sat aq.). The combined washings were dried (Na$_2$SO$_4$), filtered and concentrated. The product was recrystallized from ethylene oxide/hexane (3:1) to produce 0.55 g, (1.85 mmol, 84% yield) of white crystals. $^1$H-NMR (200 MHz, CD$_2$Cl$_2$): δ 10.91 (s, 1H, NH), 9.04 (d, J=2.3 Hz, 1H, H$_6$), 8.23 (d, J=9.0 Hz, 1H, H$_4$), 7.52 (cm, 1H, H$_{4'}$), 7.26 (dd, J=2.3, 9.0 Hz, 1H, H$_4$), 7.08 (m, 1H, H$_{3',5'}$).

EXAMPLE 62

Preparation of N-(2,6-Difluorobenzoyl)-2-Amino-3-Nitroanilide

In this Example, N-(2,6-difluorobenzoyl)-2-amino-3-nitroanilide (800) was prepared according to Method A, described above, with the changes to the starting materials, notable variations, and/or additions to the method indicated as needed. Method A was also used to produce the compounds described in subsequent Examples, as indicated.

3-nitro-1,2-phenylenediamine (13.3 g, 86.85 mmol) and 2,6-difluorobenzoyl chloride (15.33 g, 10.95 mL, 86.85 mmol) were mixed and stirred overnight. The crude product was recrystallized from ethylacetate/hexane to produce 12 g (41 mmol, 48% yield) of yellow crystals. $^1$H-NMR (300 MHz, DMSO-d$_6$): δ 10.23 (s, 1H, NH), 7.99 (dd, J=8.7, 1.4 Hz, 1H, H$_4$), 7.71 (dd, J=7.6 Hz, 1.4 Hz, 1H, H$_6$), 7.62 (m, 1H, H$_{4'}$), 7.28 (m, 2H, H$_{3',5'}$), 6.91 (s, 2H, NH$_2$), 6.76 (dd, J=8.7, 7.6 Hz, 1H, H$_5$).

EXAMPLE 63

Preparation of N-(2,6-Difluorobenzoyl)-2,3-Dimethyl-6-Nitroanilide

In this Example, N-(2,6-difluorobenzoyl)-2,3-dimethyl-6-nitroanilide (900) was prepared according to Method A, using 2,3-dimethyl-6-nitroaniline (2.00 g, 12.04 mmol) and 2,6-difluorobenzoyl chloride (7) (1.50 mL, 13.93 mmol, 115 M %). After 3 hours of mixing, an additional (7) (0.50 mL, 4.64 mmol, 40 M %) was added to the mixture. After an additional 5 hours of mixing, the compound was recrystallized from ethylacetate/hexane (1:4) to produce 2.71 g (8.85 mmol, 74% yield) of yellow crystals. $^1$H-NMR (300 MHz, CD$_2$Cl$_2$): δ 8.67 (s, 1H, NH), 7.81(d, J=8.4 Hz, 1H, H$_6$), 7.48 (m, 1H, H$_{4'}$), 7.28 (d, J=8.4 Hz, 1H, H$_5$), 7.05 (m, 2H, H$_{3',5'}$), 2.44 (s, 3H, CH$_3$), 2.31 (s, 3H, CH$_3$).

EXAMPLE 64

Preparation of N-(2,6-Difluorobenzoyl)-3-Methyl-6-Nitroanilide

In this Example, N-(2,6-difluorobenzoyl)-3-methyl-6-nitroanilide (1000) was prepared according to Method A. First, 5-methyl-2-nitroaniline (4.95 g, 32.5 mmol) was mixed with 2,6-difluorobenzoyl chloride (4.50 mL, 41.8 mmol, 130 M %), as described. After recrystallization from ethylacetate, 8.71 g (29.8 mmol, 92% yield) of yellow crystals were produced. $^1$H-NMR (300 MHz, CD$_2$Cl$_2$): δ 10.85 (s, 1H, NH), 8.75 (s, 1H, H$_2$), 8.16 (d, J=8.6, 1H, H$_5$), 7.50 (m, 1H, H$_{4'}$), 7.48 (d, J=8.6, 1H, H$_4$), 7.06 (m, 2H, H$_3$), 2.50 (s, 3H, CH$_3$).

EXAMPLE 65

Preparation of N-(2,6-Difluorobenzoyl)-4-Methyl-2-Nitroanilide

In this Example, N-(2,6-difluorobenzoyl)-4-methyl-2-nitroanilide (1100) was prepared according to Method A. First, 4-methyl-2-nitroaniline (4.95 g, 32.5 mmol) was mixed with 2,6-difluorobenzoyl chloride (7) (4.50 mL, 41.8 mmol, 130 M %), as described. After recrystallization from ethylacetate, 6.69 g (22.9 mmol, 70% yield) of yellow crystals were produced. $^1$H-NMR (300 MHz, CD$_2$Cl$_2$): δ 10.64 (s, 1H, NH), 8.75 (d, J=8.6, 1H, H$_6$), 8.06 (s, 1H, H$_3$), 7.52 (m, 1H, H$_{4'}$), 7.48 (d, J=8.6, 1H, H$_5$), 7.06 (m, 2H, H$_{3',5'}$), 2.42 (s, 3H, CH$_3$).

EXAMPLE 66

Preparation of N-(2,6-Difluorobenzoyl)-4-Bromo-2-Nitroanilide

In this Example, N-(2,6-difluorobenzoyl)-4-bromo-2-nitroanilide (1200) was prepared according to Method A. First, N-(2,6-difluorobenzoyl)-2-nitroanilide (Example 5) (1.20 g, 8.69 mmol) was suspended in 10 mL pyridine/THF (1:1). Bromine (0.5 mL) dissolved in acetic acid (0.5 mL) was then added to the mixture. After stirring for 1 hour at room temperature, the reaction was quenched with NaHCO$_3$ (sat. aq.). The solution was extracted with CH$_2$Cl$_2$, and the organic extract was washed with NaCl (sat. aq.). The combined washings were dried (Na$_2$SO$_4$), filtered and concentrated. The product was recrystallized from ethylacetate to produce 1.55 g, (4.34 mmol, 50% yield) of yellow crystals. $^1$H-NMR (200 MHz, CD$_2$Cl$_2$): δ 10.72 (br s, 1H, NH), 8.85 (d J=9.1 Hz, 1H, H$_5$), 8.42 (d J=2.4 Hz, 1H, H$_3$), 7.84 (ddd, J=0.5, 2.4, 9.1 Hz, 1H, H$_6$), 7.52 (m, 1H, H$_{4'}$), 7.07 (m, 2H, H$_{3',5'}$).

EXAMPLE 67

Preparation of N-(2,6-Difluorobenzoyl)-N-(2,6-Difluorobenzyl)-4-Bromo-2-Nitroanilide In this Example, N-(2,6-difluorobenzoyl)-N-(2,6-difluorobenzyl)-4-bromo-2-nitroanilide (1400) was prepared according to Method E. Method E was also used to produce the compounds described in subsequent Examples, with the changes to the starting materials, notable variations, and/or additions to the method indicated as needed.

N-(2,6-difluorobenzoyl)-4-bromo-2-nitroanilide (Example 66) (0.26 g, 0.73 mmol) and 2,6-difluoro-α-bromo-toluene (0.27 g, 1.30 mmol, 180 M %) were dissolved in THF (2 mL), to which NaH (0.15 g, 500 M %) was added. After 6 hours, the reaction was quenched with methanol and concentrated. The residue was redissolved in $CH_2Cl_2$, and washed with $NaHCO_3$ (sat. aq.) and NaCl (sat. aq.). The combined washings were dried ($Na_2SO_4$), filtered and concentrated. The product was purified by flash chromatography eluting with ethylacetate/hexane (1:4), and recrystallized from diethyl ether: hexane (3:1) to produce 0.26 g, (0.54 mmol, 74% yield) of white crystals. $^1$H-NMR (200 MHz, DMSO $d_6$) (rotamers): δ 8.30 (d, J=2.3 Hz, 1H, $H_3$, rotamer 1), 8.25 (d, J=2.3 Hz, 1H, $H_3$, rotamer 2), 8.02 (dd, J=2.3, 8.5 Hz, 1H, $H_5$, rotamer 1), 7.85 (dd, J=2.3, 8.5 Hz, 1H, $H_5$, rotamer 2), 7.68 (m, 1H, $H_{4'}$, rotamer 1), 7.54–7.27 (m, 5H, $H_{6,4''}$rotamers 1 & $H_{6,4'',4''}$ rotamer 2), 7.16–6.94 (m, $H_{3',5',3'',5''}$ rotamers 1&2), 5.63 (d, J=14.3 Hz, 1H, $CH_2PhF_2$, rotamer 2), 4.99 (br 1H, $CH_2PhF_2$, rotamer 1), 4.87 (br, 1H, $CH_2PhF_2$, rotamer 1), 4.86 (d, J=14.3 Hz, 1H, $CH_2Ph$, rotamer 2).

EXAMPLE 68

Preparation of N-(2,6-Difluorobenzoyl)-N-(2,6-Difluorobenzyl)-4-Chloro-2-Nitroanilide In this Example, N-(2,6-difluorobenzoyl)-N-(2,6-difluorobenzyl)-4-chloro-2-nitroanilide (1500) was prepared according to Method E, using N-(2,6-difluorobenzoyl)-4-chloro-2-nitroanilide (Example 59) (600 mg, 1.92 mmol) mixed with 2,6-difluoro-α-bromo-toluene (1300) (478 mg, 2.3 mmol). After recrystallization from diethyl ether/hexane (3:1), 620 mg (1.41 mmol, 74%) of white crystals was produced. $^1$H-NMR (300 MHz, $CD_2Cl_2$) (rotamers): δ 8.02 (d, J=2.4 Hz, 1H, $H_3$, rotamer 1), 7.95 (d, J=2.4 Hz, 1H, $H_3$, rotamer 2), 7.57 (dd, J=8.6, 2.4 Hz, 1H, $H_5$, rotamer 1), 7.50 (m, 1H, $H_{4''}$, rotamer 1), 7.30 (dd, J=8.4, 2.4 Hz, 1H, $H_5$, rotamer 2), 7.35–7.03 (m, 5H, $H_{4''}$ rotamer 2 & $H_{6,4'}$ rotamer 1&2), 6.94–6.68 (m, 8H, $H_{3',5',3'',5''}$, rotamer 1 & 2), 5.84 (d, J=14.4, 1H, $CH_2PhF_2$, rotamer 2), 4.94 (br s, 2H, $CH_2PhF_2$, rotamer 1), 4.82 (d, J=14.4 Hz, 1H, $CH_2PhF_2$, rotamer 2).

EXAMPLE 69

Preparation of N-(2,6-Difluorobenzoyl)-N-(2,6-Difluorobenzyl)-5-Chloro-2-Nitroanilide In this Example, N-(2,6-difluorobenzoyl)-N-(2,6-difluorobenzyl)-5-chloro-2-nitroanilide (1600) was prepared according to Method E. First, N-(2,6-difluorobenzoyl)-5-chloro-2-nitroanilide (Example 61) (1.95 g, 6.24 mmol) and 2,6-difluoro-α-bromo-toluene (1.40 g, 6.76 mmol, 110 M %) were mixed for 2 hours. Then, an additional volume of 2,6-difluoro-α-bromo-toluene (1.30 g, 100 M % ) was added. After 5 hours of mixing, an additional volume of 2,6-difluoro-α-bromo-toluene was added (0.75 g, 60 M %) was added. After mixing for 8 hours, purification by flash chromatography, elution with ethyl acetate/hexane (1:4) to produce 2.06 g (4.69 mmol, 75% yield) of white crystals. $^1$H-NMR (200 MHz, DMSO-$d_6$) (rotamers): δ 8.08 (d, J=9.4 Hz, 1H, $H_6$, rotamer 1), 8.03 (d, J=8.8 Hz, 1H, $H_6$, rotamer 2), 7.79–6.91 (m, 16H, $H_{3,4,3',4',5',3'',4'',5''}$ rotamer 1&2), 5.55 (d, J=14.7, 1H, $CH_2PhF_2$, rotamer 2), 5.12 (br, 1H, $CH_2PhF_2$, rotamer 1), 4.99 (d, J=14.7 Hz, 1H, $CH_2PhF_2$, rotamer 2), 4.87 (br, 1H, $CH_2PhF_2$, rotamer 1).

EXAMPLE 70

Preparation of N-(2,6-Difluorobenzoyl)-N-(2,6-Difluorobenzyl)-4-Methyl-2-Nitroanilide In this Example, N-(2,6-difluorobenzoyl)-N-(2,6-difluorobenzyl)-4-methyl-2-nitroanilide (1700) was prepared according to Method E. N-(2,6-difluorobenzoyl)-4-methyl-2-nitroanilide (Example 65) (2.00 g, 6.84 mmol) and 2,6-difluoro-α-bromo-toluene (2.12 g, 10.2 mmol, 150 M %) were mixed for 3 hours, and recrystallized from diethyl ether/hexane (3:1) to produce 2.80 g (6.69 mmol, 98% yield) of white crystals. $^1$H-NMR (300 MHz, DMSO-$d_6$) (rotamers): δ 7.89 (dd, J=2.0, 0.9 Hz, 1H, $H_3$ rotamer 1), 7.87 (dd, J=2.0, 0.8 Hz, 1H, $H_3$ rotamer 2), 7.66 (m, 1H, $H_{4'}$ rotamer b 1), 7.56 (ddd, J=8.2, 2.0, 0.9 Hz, 1H, $H_5$ rotamer 1), 7.43 (m, 1H, $H_{4'}$ rotamer 2), 7.37–7.27 (m, 5H, $H_5$ rotamer 2, $H_{3',5'}$ rotamer 1, $H_{4''}$ rotamer 1&2) 7.21 (d, J=8.2 Hz, 1H, $H_6$ rotamer 1), 7.07 (m, 2H, $H_{3',5'}$ rotamer 2), 7.01–6.90 (m, 4H, $H_{3'',5''}$ rotamer 1&2), 6.83 (br d, J=7.7 Hz, 1H, $H_6$ rotamer 2), 5.71 (d, J=14.4 Hz, 1H, $CHPhF_2$rotamer 2), 4.97 (d, J=14.4 Hz, 1H, $CHPhF_2$rotamer 1), 4.83 (d, J=14.4 Hz, 1H, $CHPhF_2$rotamer 1), 4.78 (d, J=14.4 Hz, 1H, $CHPhF_2$rotamer 2), 2.41 (s, 3H, $CH_3$ rotamer 1), 2.27 (s, 3H, $CH_3$ rotamer 2).

EXAMPLE 71

Preparation of N-(2,6-Difluorobenzoyl)-N-(2,6-Difluorobenzyl)-5-Methyl-2-Nitroanilide In this Example, N-(2,6-difluorobenzoyl)-N-(2,6-difluorobenzyl)-5-methyl-2-nitroanilide (1800) was prepared according to Method E. N-(2,6-difluorobenzoyl)-3-methyl-6-nitroanilide (Example 64) (2.00 g, 6.84 mmol) and 2,6-difluoro-α-bromo-toluene (2.12 g, 10.2 mmol, 150 M %) were mixed for 3 hours. After recrystallization from diethyl ether/hexane (3:1), 1.92 g (4.59 mmol, 67% yield) of white crystals were produced. $^1$H-NMR (200 MHz, $CD_3OD$) (rotamers): δ 7.92 (d, J=8.5 Hz, 1H, $H_6$, rotamer 1), 7.89 (d, J=8.5, 1H, $H_6$, rotamer 2), 7.60 (m, 1H, $H_{4'}$, rotamer 1), 7.44–6.72 (m, 15H, $H_{3,4,3',5',3'',4'',5''}$ rotamers 1 & $H_{3,4,3',4',5',3'',4'',5''}$ rotamer 2), 5.86 (d, J=14.3 Hz, 1H, $CH_2PhF_2$, rotamer 2), 4.98 (br, 2H, $CH_2PhF_2$, rotamer 1), 4.88 (d, J=14.3 Hz, 1H, $CH_2PhF_2$, rotamer 2), 2.35 (s, 3H, $CH_3$, rotamer 1), 2.35 (s, 3H, $CH_3$, rotamer 2).

EXAMPLE 72

Preparation of N-(2,6-Difluorobenzoyl)-N-(2,6-Difluorobenzyl)-2-Methyl-6-Nitroanilide In this Example, N-(2,6-difluorobenzoyl)-N-(2,6-difluorobenzyl)-2-methyl-6-nitroanilide (1900) was prepared according to Method E. First, 2,6-difluorobenzoyl-2-methyl-6-nitroanilide (Example 6) (450 mg, 1.54 mmol) and 2,6-difluoro-α-bromo-toluene (351 mg, 1.69 mmol) were mixed. After recrystallization from diethylether/methanol 490 mg (1.17 mmol, 76% yield) of colorless crystals was produced. $^1$H-NMR (300 MHz, $CD_2Cl_2$): δ 7.82 (dd, J=8.0, 1.5 Hz, 1H, $H_5$), 7.52 (m, 1H, $H_{4bz}$), 7.51 (dd, 1H, J=7.9, 1.6 Hz, 1H, $H_3$), 7.42 (t, 1H, J=7.9 Hz, $H_4$), 7.25 (m, 1H, $H_{4bn}$), 7.12 (m, 2H, $H_{3bz,5bz}$), 6.74 (m, 2H, $H_{3bn,5bn}$), 4.80 (s, 2H, $CH_2$), 2.17 (s, 3H, $CH_3$).

EXAMPLE 73

Preparation of 1-(2,6-Difluorobenzyl)-2-(2,6-Difluorophenyl)-5-Bromobenzimidazole In this Example, 1-(2,6-Difluorobenzyl)-2-(2,6-difluorophenyl)-5-bromobenzimidazole (2100) was prepared according to Method F. Method F was also used to produce the compounds described in subsequent Examples, with the changes to the starting materials, notable variations, and/or additions to the method indicated as needed.

First, 2,6-difluoro-α-bromo-toluene (0.26 g, 0.54 mmol) was dissolved in glacial acetic acid (5 mL), followed by addition of iron powder (0.55 g) to the mixture. After 30 min, the reaction was concentrated to dryness, diluted with ethyl acetate, and adjusted to pH 7 with $NaHCO_3$ (sat. aq.). The organic solution was collected and washed with $NaHCO_3$ and NaCl, dried ($Na_2SO_4$), filtered, and concentrated. The product was purified by flash chromatography eluting with 2% $MeOH/CH_2Cl_2$ and then recrystallized from 3:1 diethyl ether/hexane to produce 0.14 g (0.33 mmol, 62% yield) of white crystals. $^1$H-NMR (300 MHz, $CD_2Cl_2$): δ 8.11 (dd, J=0.6, 1.9 Hz, 1H, $H_4$), 7.56 (cm, 1H, $H_{4''}$), 7.41 (AB, J=1.9, 8.7 Hz, 1H, $H_5$), 7.40 (AB, J=0.6, 8.7 Hz, 1H, $H_6$), 7.26 (cm, 1H, $H_{4'}$), 7.10 (cm, 2H, $H_{3'',5''}$), 6.83 (cm, 2H, $H_{3',5'}$), 5.35 (s, 2H, $CH_2PhF_2$). Anal. ($C_{20}H_{11}BrF_4N_2$x3/4$H_2O$), C,H,N.

EXAMPLE 74

Preparation of 1-(2,6-Difluorobenzyl)-2-(2,6-Difluorophenyl)-5-Chlorobenzimidazole In this Example, 1-(2,6-difluorobenzyl)-2-(2,6-difluorophenyl)-5-chlorobenzimidazole (2200) was prepared according to Method F. N-(2,6-difluorobenzoyl)-N-(2,6-difluorobenzyl)-4-chloro-2-nitroanilide (Example 68) (620 mg, 1.41 mmol) and iron powder (200 mg) were mixed for 3 hours. After recrystallization, 250 mg (0.64 mmol, 45%) of colorless crystals were produced, with a mp of 136° C. $^1$H-NMR (300 MHz, $CD_2Cl_2$): δ 7.77 (d, J=1.95 Hz, $H_4$), 7.55 (m, 1H, $H_{4'}$), 7.42 (d, J=8.7 Hz, 1H, $H_7$), 7.27 (dd, J=8.7, 1.95 Hz, 1H, $H_6$), 7.26 (m, 1H, $H_{4''}$), 7.09 (m, 2H, $H_{3',5'}$), 6.82 (m, 2H, $H_{3'',5''}$), 5.34 (s, 2H, $CH_2$). Anal. ($C_{20}H_{11}ClF_4N_2$) C,H,N

EXAMPLE 75

Preparation of 1-(2,6-Difluorobenzyl)-2-(2,6-Difluorophenyl)-6-Chlorobenzimidazole In this Example, 1-(2,6-difluorobenzyl)-2-(2,6-difluorophenyl)-6-chlorobenzimidazole (2300) was prepared according to Method F. N-(2,6-difluorobenzoyl)-N-(2,6-difluorobenzyl)-5-chloro-2-nitroanilide (Example 69) (0.57 g, 1.30 mmol) and iron powder (17) (0.43 g) were mixed for 1 hour. The crude product was purified by flash chromatography eluted with 2% $MeOH/CH_2Cl_2$, and recrystallized from diethyl ether/ hexane (3:1), to produce 0.43 g (1.10 mmol, 85% yield) of white crystals. $^1$H-NMR (300 MHz, $CD_2Cl_2$): δ 7.73 (dd, J=0.9, 8.6 Hz, 1H, $H_4$), 7.56 (m, 1H, $H_{4''}$), 7.51 (d, J=1.9 Hz, 1H, $H_7$), 7.29 (dd, J=1.9, 8.6 Hz, 1H, $H_5$), 7.27 (m, 1H, $H_{4'}$), 7.09 (m, 2H, $H_{3',5'}$), 6.84 (m, 2H, $H_{3',5'}$), 5.33 (s, 2H, $CH_2PhF_2$). Anal. ($C_{20}H_{11}ClF_4N_2$) C,H,N.

EXAMPLE 76

Preparation of 1-(2,6-Difluorobenzyl)-2-(2,6-Difluorophenyl)-5-Methylbenzimidazole In this Example, 1-(2,6-difluorobenzyl)-2-(2,6-difluorophenyl)-5-methylbenzimidazole (2400) was prepared according to Method F. N-(2,6-difluorobenzoyl)-N-(2,6-difluorobenzyl)-4-methyl-2-nitroanilide (Example 70) (1.55 g, 3.71 mmol) and iron powder (0.79 g) were mixed, and then recrystallized from diethyl ether/hexane (3:1), to produce 0.85 g (2.30 mmol, 62% yield) of white crystals. $^1$H-NMR (300 MHz, $CD_2Cl_2$): δ 7.60–7.49 (cm, 2H, $H_{4,4''}$), 7.37 (d, J=8.4 Hz, 1H, $H_7$), 7.24 (m, 2H, $H_{4'}$), 7.14 (m, 1H, $H_6$), 7.09 (m, 2H, $H_{3'',5''}$), 6.81 (m, 2H, $H_{3',5'}$), 5.34 (s, 2H, $CH_2PhF_2$), 2.47 (s, 3H, $CH_3$). Anal. ($C_{21}H_{14}F_4N_2$) C,H,N.

EXAMPLE 77

Preparation of 1-(2,6-Difluorobenzyl)-2-(2,6-Difluorophenyl)-6-Methylbenzimidazole In this Example, 1-(2,6-difluorobenzyl)-2-(2,6-difluorophenyl)-6-methylbenzimidazole (2500) was prepared according to Method F. N-(2,6-difluorobenzoyl)-N-(2,6-difluorobenzyl)-5-methyl-2-nitroanilide (Example 71) (1.56 g, 3.73 mmol) and iron powder (0.79 g) were mixed. After recrystallization from diethyl ether/hexane 0.89 g (2.41 mmol, 64% yield) of white crystals were produced. $^1$H-NMR (300 MHz, $CD_2Cl_2$): δ 7.64 (cm, 1H, $H_4$), 7.52 (m, 1H, $H_{4''}$), 7.30–7.19 (m, 2H), $H_{7,4'}$), 7.14–7.03 (m, 3H, $H_{5,3'',5''}$), 6.81 (m, 2H, $H_{3',5'}$), 5.33 (s, 2H, $CH_2PhF_2$), 2.48 (s, 3H, $CH_3$). Anal. ($C_{21}H_{14}F_4N_2$) C,H,N.

EXAMPLE 78

Preparation of 1-(2,6-Difluorobenzyl)-2-(2,6-Difluorophenyl)-7-Methylbenzimidazole In this Example, 1-(2,6-difluorobenzyl)-2-(2,6-difluorophenyl)-7-methylbenzimidazole (2600) was prepared according to Method F. N-(2,6-difluorobenzoyl)-N-(2,6-difluorobenzyl)-2-methyl-6-nitroanilide (Example 72) (300 mg, 0.72 mmol) and iron powder (50 mg) were mixed. After recrystallization from ethyl acetate, 149 mg (0.15 mmol, 56% yield) of colorless crystals were produced, with a mp of 177° C. $^1$H-NMR (300 MHz, $CD_2Cl_2$): 7.62 (d, J=8.2 Hz, 1H, $H_4$), 7.45 (m, 1H, $H_{4'}$), 7.18 (m, 1H, $H_{4''}$), 7.17 (dd, J=7.3, 8.2, 1H, $H_5$), 7.08 (d, J=7.3, $H_6$), 6.95 (m, 2H, $H_{3',5'}$), 6.70 (m, 2H, $H_{3'',5''}$), 5.64 (s, 2H, $CH_2$), 2.74 (s, 3H, $CH_3$). Anal. ($C_{21}H_{14}F_4N_2$) C,H,N.

EXAMPLE 79

Preparation of 2-(2,6-Difluorophenyl)-4,5-Dimethylbenzimidazole

In this Example, 2-(2,6-difluorophenyl)-4,5-dimethylbenzimidazole (2700) was produced according to Method F. N-(2,6-difluorobenzoyl)-2,3-dimethyl-6-nitroanilide (Example 63) (1.40 g, 4.57 mmol) and iron powder (1.05 g) were mixed for 1 h, and recrystallized from ethylacetate to produce 1.07 g (4.14 mmol, 91% yield) of white crystals. $^1$H-NMR (300 MHz, $CD_2Cl_2$): δ 7.49–7.37 (m, 2H, $H_{4',7}$), 7.16–7.07 (m, 3H, $H_{3',5',6}$), 2.54 (br s, 3H, $CH_3$), 2.42 (s, 3H, $CH_3$).

EXAMPLE 80

Preparation of 2-(2,6-Difluorophenyl)-4-Nitrobenzimidazole

In this Example, 2-(2,6-difluorophenyl)-4-nitrobenzimidazole (2800) was prepared according to Method F. N-(2,6-difluorobenzoyl)-2-amino-3-nitroanilide (Example 62) (12 g, 41 mmol) was dissolved in 130 mL of acetic acid, heated to reflux, and stirred for 12 hours. The reaction mixture was cooled to room temperature, neutralized with NaOH (4N), basified with NaHCO$_3$ (1%), and extracted with ethylacetate (3×300 mL). The combined organic layers were dried (Na$_2$SO$_4$), filtered, and evaporated. The remaining crystals were recrystallized from ethylacetate/hexane to produce 7.7 g, (28 mmol, 68%) of crystals. $^1$H-NMR (300 MHZ, CD$_2$Cl$_2$): δ 11.00 (s, 1H, NH), 8.23 (dd, J=8.2, 0.8 Hz, 1H, H$_5$), 8.21 (dd, J=8.0, 0.8 Hz, 1H, H$_7$), 7.54 (m, 1H, H$_{4'}$), 7.45 (dd, J=8.0, 8.2 Hz, 1H, H$_6$), 7.13 (m, 2H, H$_{3',5'}$).

EXAMPLE 81

Preparation of 2-(2,6-Difluorophenyl)-5-Nitrobenzimidazole

In this Example, 2-(2,6-difluorophenyl)-5-nitrobenzimidazole (2900) was prepared according to Method F. 2-(2,6-difluorophenyl)-benzimidazole (Example 12) (2.00 g, 8.70 mmol) was dissolved in H$_2$SO$_4$ (5.0 mL), and HNO$_3$ (5.0 mL) was added. After 2 hours at room temperature, the reaction was quenched with ice (50 mL), filtered and washed with water yielding a white solid (1.92 g, 80% yield). $^1$H-NMR (300 MHz, CD$_2$Cl$_2$): δ 8.60 (d, J=2.2 Hz, 1H, H$_4$), 8.25 (dd, J=2.2, 8.9 Hz, 1H, H$_7$), 7.78 (d, J=8.9 Hz, 1H, H$_6$), 7.65 (m, 1H, H$_{4'}$), 7.24 (m, 2H, H$_{3',5'}$).

EXAMPLE 82

Preparation of 1-(2,6-Difluorobenzyl)-2-(2,6-Difluorophenyl)-4,5-Dimethylbenzimidazole In this Example, 1-(2,6-difluorobenzyl)-2-(2,6-difluorophenyl)-4,5-dimethylbenzimidazole (3000) was prepared according to Method E. 2-(2,6-difluorophenyl)-4,5-dimethylbenzimidazole (Example 79) (0.25 g, 0.97 mmol) and 2,6-difluoro-α-bromo-toluene (0.44 g, 2.12 mmol, 220 M %) were mixed. After flash chromatography, elution with 4% MeOH/CH$_2$Cl$_2$, and recrystallization from ethylacetate/hexane (1:1) 0.38 g (0.81 mmol, 83% yield) of white crystals was produced. $^1$H-NMR (300 MHz, CD$_3$OD): δ 7.63 (cm, 1H, H$_{4'}$), 7.34 (cm, 1H, H$_6$), 7.30 (cm, 1H, H$_{4''}$), 7.16 (cm, 1H, H$_7$), 7.13 (cm, 2H, H$_{3',5'}$), 6.85 (cm, 2H, H$_{3'',5''}$), 5.40 (s, 2H, CH$_2$PhF$_2$), 2.54 (s, 3H, CH$_3$), 2.40 (s, 3H, CH$_3$). Anal. (C$_{22}$H$_{16}$F$_4$N$_2$) C,H,N.

EXAMPLE 83

Preparation of 1-(2,6-Difluorobenzyl)-2-(2,6-Difluorophenyl)-4-Nitrobenzimidazole In this Example, 1-(2,6-difluorobenzyl)-2-(2,6-difluorophenyl)-4-nitrobenzimidazole (3100) was prepared according to Method E. 2-(2,6-difluorophenyl)-4-nitrobenzimidazole (Example 80) (7.7 g, 28 mmol) and 2,6-difluoro-α-bromo-toluene (6.95 g, 33.6 mmol) were mixed as described. After recrystallization from diethyl ether/hexane (3:1), 9.8 g (24.4 mmol, 87%) of slightly brown crystals were produced, with a mp of 169° C. $^1$H-NMR (300 MHz, CD$_2$Cl$_2$): δ 8.13 (dd, J=8.1, 0.92 Hz, 1H, H$_5$), 7.86 (dd, J=8.1, 0.9 Hz, 1H, H$_7$), 7.59 (m, 1H, H$_{4'}$), 7.43 (dd, J=8.1 Hz, H$_6$), 7.28 (m, 1H, H$_{4''}$), 7.12 (m, 2H, H$_{3',5'}$), 6.84 (m, 2H, H$_{3'',5''}$), 5.44 (s, 2H, CH$_2$). Anal. (C$_{20}$H$_{11}$F$_4$N$_3$O$_2$) C,H,N.

EXAMPLE 84

Preparation of 1-(2,6-Difluorobenzyl)-2-(2,6-Difluorophenyl)-5-Nitrobenzimidazole In this Example, 1-(2,6-difluorobenzyl)-2-(2,6-difluorophenyl)-5-nitrobenzimidazole (3200) was prepared according to Method E. 2-(2,6-difluorophenyl)-5-nitrobenzimidazole (Example 81) (0.91 g, 3.31 mmol) and 2,6-difluoro-α-bromo-toluene (1.08 g, 5.22 mmol, 160 M %) were mixed, and a second addition of difluoro-α-bromo-toluene (0.47 g, 2.27 mmol, 70 M %) was added to the mixture after 1 hour of mixing. After flash chromatography, eluting with ethyl acetate/hexane (1:4), 1.09 g (2.71 mmol, 82% yield) of white crystals were produced. $^1$H-NMR (300 MHz, CD$_2$Cl$_2$): δ 8.69 (dd, J=0.5, 2.2 Hz, 1H, H$_4$), 8.23 (dd, J=2.2, 9.0 Hz, 1H, H$_6$), 7.59 (dd, J=0.5, 9.0 Hz, 1H, H$_7$), 7.59 (m, 1H, H$_{4'}$), 7.28 (m, 1H), H$_{4''}$), 7.12 (m, 2H, H$_{3',5'}$), 6.84 (m, 2H, H$_{3'',5''}$), 5.44 (s, 2H, CH$_2$PhF$_2$). Anal. (C$_{20}$H$_{11}$F$_4$N$_3$O$_2$) C,H,N.

EXAMPLE 85

Preparation of 1-(2,6-Difluorobenzyl)-2-(2,6-Difluorophenyl)-4-Amino-benzimidazole In this Example, 4-amino-1-(2,6-difluorobenzyl)-2-(2,6-difluorophenyl)benzimidazole (3300) was produced according to Method E. 1-(2,6-difluorobenzyl)-2-(2,6-difluorophenyl)-4-nitrobenzimidazole (Example 83) (9.2 g, 23 mmol) was dissolved in acetic acid (130 mL), and SnCl$_2$x2H$_2$O (41.5 g) dissolved in concentrated HCl (35 mL) was added. After stirring for 3 hours at room temperature, the mixture was neutralized with NaOH (4N), basified with NaHCO$_3$ (5%), diluted with water to give a final volume of 3 L, and then extracted with ethylacetate (5×300 mL). The combined ethylacetate layers were dried (Na$_2$SO$_4$), filtered, and evaporated. The residue was purified by gravity chromatography, eluting with acetone/hexane (1:1), and recrystallized from acetone/hexane/diethylether to produce 3.7 g of pink crystals (10 mmol, 44% yield), with a mp of 178° C. $^1$H-NMR (300 MHz, CD$_2$Cl$_2$): δ 7.52 (m, 1H, H$_{4'}$), 7.23 (m, 1H, H$_{4''}$), 7.07 (m, 2H, H$_{3',5'}$), 7.06 (dd, J=8.1, 7.7 Hz, 1H, H$_6$), 6.82 (d, J=8.1 Hz, H$_7$), 6.81 (m, 2H, H$_{3'',5''}$), 6.52 (d, J=7.7, 0.9 Hz, 1H, H$_5$), 5.29 (s, 2H, CH$_2$), 4.42 (s, 2H, NH$_2$).

EXAMPLE 86

Preparation of 4-Bromo-1-(2,6-Difluorobenzyl)-2-(2,6-Difluorophenyl)-4-Bromo-benzimidazole In this Example, 4-bromo-1-(2,6-difluorobenzyl)-2-(2,6-difluorophenyl)benzimidazole (3400) was produced according to Method E. To 1-(2,6-difluorobenzyl)-2-(2,6-difluorophenyl)-4-amino-benzimidazole (Example 85) (800 mg, 2.15 mmol) suspended in HBr (48%, 7 mL) at 0° C. was slowly added NaNO$_2$ (193 mg, 2.8 mmol) in water (1.5 mL). After stirring for 30 min at 0–5° C., the mixture was added to CuBr (373 mg, 2.6 mmol) dissolved in HBr (48%, 3 mL). After 30 min at room temperature, water (250 mL) was added, and the pH was adjusted to 5 with KOH 4N. The mixture was extracted with ethylacetate, dried (Na$_2$SO$_4$), filtered, and evaporated. The crude brown crystals were purified by gravity chromatography eluting with hexane/acetone (2:1), and recrystallized with diethylether/hexane (3:1) to produce 610 mg, (1.4 mmol, 65% yield) of colorless crystals, with a mp of 147° C. $^1$H-NMR (300 MHz, CD$_2$Cl$_2$): δ 7.56 (m, 1H, H$_{4'}$), 7.49 (dd, J=7.7, 0.87 Hz, 1H, H$_5$), 7.47 (d, J=7.9 Hz, H$_7$), 7.26 (m, 1H, H$_{4''}$), 7.18 (dd, J=8.2, 7.7 Hz, 1H, H$_6$), 7.09 (m, 2H, H$_{3',5'}$), 6.82 (m, 2H, H$_{3'',5''}$), 5.35 (s, 2H, CH$_2$). Anal. (C$_{20}$H$_{11}$BrF$_4$N$_2$x1/4H$_2$O) C,H,N.

EXAMPLE 87

Preparation of 1-(2,6-Difluorobenzyl)-2-(2,6-Difluorophenyl)-4-Chloro-benzimidazole In this Example, 4-chloro-1-(2,6-difluorobenzyl)-2-(2,6-difluorophenyl)benzimidazole (3500) was prepared according to Method E. To 1-(2,6-difluorobenzyl)-2-(2,6-difluorophenyl)-4-aminobenzimidazole (Example 85) (800 mg, 2.15 mmol) dissolved in concentrated HCl (7 mL) and water (5 mL) at 0° C. was slowly added $NaNO_2$ (193 mg, 2.8 mmol) in water (1.5 mL). After 30 min at 0–5° C., the mixture was added to CuCl (256 mg, 2.6 mmol) in concentrated HCl (2 mL) at 0° C. After rising to room temperature over 40 min, the pH was adjusted to pH 5, diluted with water (80 mL), extracted with ethylacetate, dried ($Na_2SO_4$), filtered, and evaporated. The residue was purified by gravity chromatography eluting with hexane/acetone (2:1), and recrystallized from acetone/hexane to produce 350 mg of yellow crystals (0.90 mmol, 42% yield), with a mp of 163° C. $^1$H-NMR (300 MHz, $CD_2Cl_2$): δ 7.56 (m, 1H, $H_{4'}$), 7.43 (dd, J=8.0, 1.1 Hz, 1H, $H_7$), 7.31 (dd, J=7.8, 1.1 Hz, 1H, $H_5$), 7.26 (m, 1H, $H_{4''}$), 7.24 (dd, J=8.0, 7.8 Hz 1H, $H_6$), 7.09 (m, 2H, $H_{3',5'}$), 6.83 (m, 2H, $H_{3'',5''}$), 5.36 (s, 2H, $CH_2$). Anal. ($C_{20}H_{11}ClF_4N_2$) C,H,N.

EXAMPLE 88

Preparation of 1-(2,6-Difluorobenzyl)-2-(2,6-Difluorophenyl)-4-Acetamidobenzimidazole In this Example, 1-(2,6-difluorobenzyl)-2-(2,6-difluorophenyl)-4-acetamidobenzimidazole (3600) was prepared according to Method E. 1-(2,6-difluorobenzyl)-2-(2,6-difluorophenyl)4-aminobenzimidazole (Example 85) (0.30 g, 0.81 mmol) was dissolved in THF (3 mL), and acetic anhydride (100 mL, 1.06 mmol) was then added. After 3 hours, additional acetic anhydride (20 mL, 0.21 mmol) was added. After 5 hours, the reaction was concentrated to dryness, diluted with ethyl acetate (50 mL), and washed with $NaHCO_3$ (25 mL) and NaCl (25 mL). The combined washings were dried ($Na_2SO_4$), filtered, and concentrated. The product was recrystallized from diethyl ether/hexane (3:1) to produce 0.32 g (0.77 mmol, 95% yield) of white crystals. $^1$H-NMR (300 MHz, $CD_2Cl_2$): δ 8.49 (1H, br, NH), 8.20 (d, J=7.8 Hz, 1H, $H_5$), 7.56 (m, 1H, $H_{4'}$), 7.26 (t, J=7.9 Hz, 1H, $H_6$), 7.26 (m, 1H, $H_{4''}$), 7.19 (d, J=7.9 Hz, 1H, $H_7$), 7.10 (m, 2H, $H_{3',5'}$), 6.82 (m, 2H, $H_{3'',5''}$), 5.34 (s, 2H, $CH_2PhF_2$), 2.21 (s, 3H, Ac). Anal. ($C_{22}H_{15}F_4N_3O$) C,H,N.

EXAMPLE 89

Preparation of 1-(2,6-Difluorobenzyl)-2-(2,6-Difluorophenyl)-4-N,N-Dimethylaminobenzimidazole In this Example, 1-(2,6-difluorobenzyl)-2-(2,6-difluorophenyl)-4-N,N-dimethylaminobenzimidazole (3700) was prepared according to Method E. A slurry of 1-(2,6-difluorobenzyl)-2-(2,6-difluorophenyl)-4-aminobenzimidazole (Example 85) (0.37 g, 1.0 mmol) and sodium borohydride (0.27 g) was added to a mixture of 3 M $H_2SO_4$ (0.80 mL) and 37% $H_2CO$ (0.50 mL). After the addition was complete, the mixture was concentrated to dryness, diluted with ethyl acetate, and washed with $Na_2CO_3$ and NaCl. The combined washings were dried ($Na_2SO_4$), filtered, concentrated. The crude product was purified by recrystallization from diethyl ether/hexane (3:1) to produce 0.34 g (0.85 mmol, 85% yield) of white crystals. $^1$H-NMR (300 MHz, $CD_2Cl_2$): δ 7.51 (m, 1H, $H_{4'}$), 7.23 (m, 1H, $H_{4''}$), 7.13 (t, J=8.0 Hz, 1H, $H_6$), 7.06 (m, 2H, $H_{3',5'}$), 6.90 (d, J-8.0 Hz, 1H, $H_5$), 6.80 (m, 2H, $H_{3'',5''}$), 6.48 (d, J=8.0 Hz, 1H, $H_7$), 5.30 (s, 2H, $CH_2PhF_2$), 3.18 (s, 6H, $N(CH_3)_2$). Anal. ($C_{22}H_{17}F_4N_3$) C,H,N.

EXAMPLE 90

Reverse Transcriptase Assay

In this Example, the effects of various compounds were tested for their ability to inhibit the RNA-dependent DNA polymerase (i.e., RT) activity of purified RT. Briefly, in the basic assay (e.g., controls), purified RT protein (0.015 mg/mL) was incubated in a 100 μL reaction mixture containing 25 mM Tris (pH 8.0), 75 mM KCl, 8 mM $MgCl_2$, 2 mM dithiothreitol, 0.1 units poly (rC)-oligo(dG), 0.01 mM dGTP, 1×BSA, 10 mM CHAPS, 0.025 mCi ($\alpha^{35}$S)dGTP (specific activity, 1000 Ci/mmol), for 1 hour at 37° C. In the test assays, various concentrations of anti-RT compounds were included in the reaction mixture. The assays were stopped by adding 1 mL of 10% trichloroacetic acid and 30 μL of denatured and sheared salmon sperm DNA (10 mg/mL) as a carrier. The labeled polymer was collected on Whatman glass GF/C filters by suction filtration, washed with 10% trichloroacetic acid and 95% ethanol, and the radioactivity was counted.

Table 3 shows the structures, physical and biological data, as well as remaining HIV RT activity reported as a percent of the control in HIV RT inhibition assays, for various 1-(2,6-difluorobenzyl)-2-substituted-benzimidazoles produced using the methods of the present invention.

EXAMPLE 91

Cytopathic Cell Killing Anti-Viral Assay

In this Example, the antiviral and cellular toxicity of NNRTIs was investigated, using the cytopathic cell killing assay described by Yang (Yang et al., "Characteristics of a Group of Non-nucleoside Reverse Transcriptase Inhibitors with Structural Diversity and Potent Anti-Human Immunodeficiency Virus Activity," Leukemia 9:S75–S85 [1995]). Briefly, in this method cells (e.g., the CEM-SS cell line, available from the NIAID AIDS Research and Reference Program [ARRRP]) were seeded at a density of 5×10$^3$ cells/well, into the wells of a 96-well microtiter plate. The cells were then infected with HIV virus (either mutant or WT), at a multiplicity of infection (MOI) previously determined to provide complete cell killing by 6 days of culture post-infection (e.g., MOI of 0.01–0.05). Each of the HIV isolates was pre-titered to induce equivalent levels of infection based on cell killing or virus production, prior to their use in these assays. A range of test compound concentrations was added to the wells in triplicate (e.g., serial half-log dilutions) to evaluate inhibition of HIV infection. Controls for each assay included drug controls (drug colorimetric control wells), drug cytotoxicity control wells (cells with drug), virus control wells (cells with virus), and cell viability controls (cells only). Positive control drugs (e.g. AZT and ddC) were also run in parallel.

After six days of incubation at 37° C., cell viability was determined spectrophotometrically at 450 nm for each well, using the metabolic reduction of XTT to a soluble colored formazan. (See, Gartner and Popovic, "Virus Isolation and Production, in Aldovini and Walker (eds.), *Techniques in HIV Research*, Stockton Press, NY, pp. 69–63 [1991]; and Nara and Fischinger, "Quantitative Infectivity Assay for HIV-1 and HIV-2, " Nature 332:469–470 [1988]).

Antiviral and toxicity data were reported as the quantity of drug required to inhibit 50% of virus-induced cell killing or virus production ($EC_{50}$), and the quantity of drug required to reduce enzyme activity by 50% ($IC_{50}$). The in vitro therapeutic index ($TI_{50}$) was defined as the fold-difference between the $EC_{50}$ and $IC_{50}$. The results for the various compounds are included in FIGS. 8 and 19. In addition, graphs showing the summary data for three compounds are shown in FIGS. 10–12. FIG. 10 shows the graph for compound 33. As indicated in this Figure, 33 exhibited very effective therapeutic dose. FIG. 11 shows the graph for compound 34, another compound that also exhibited an effective therapeutic dose. FIG. 12 shows the graph for compound 2100, a compound that was found to be inactive.

EXAMPLE 92

Comparisons Of Inactive Compounds With Active Compounds

Figure 6:
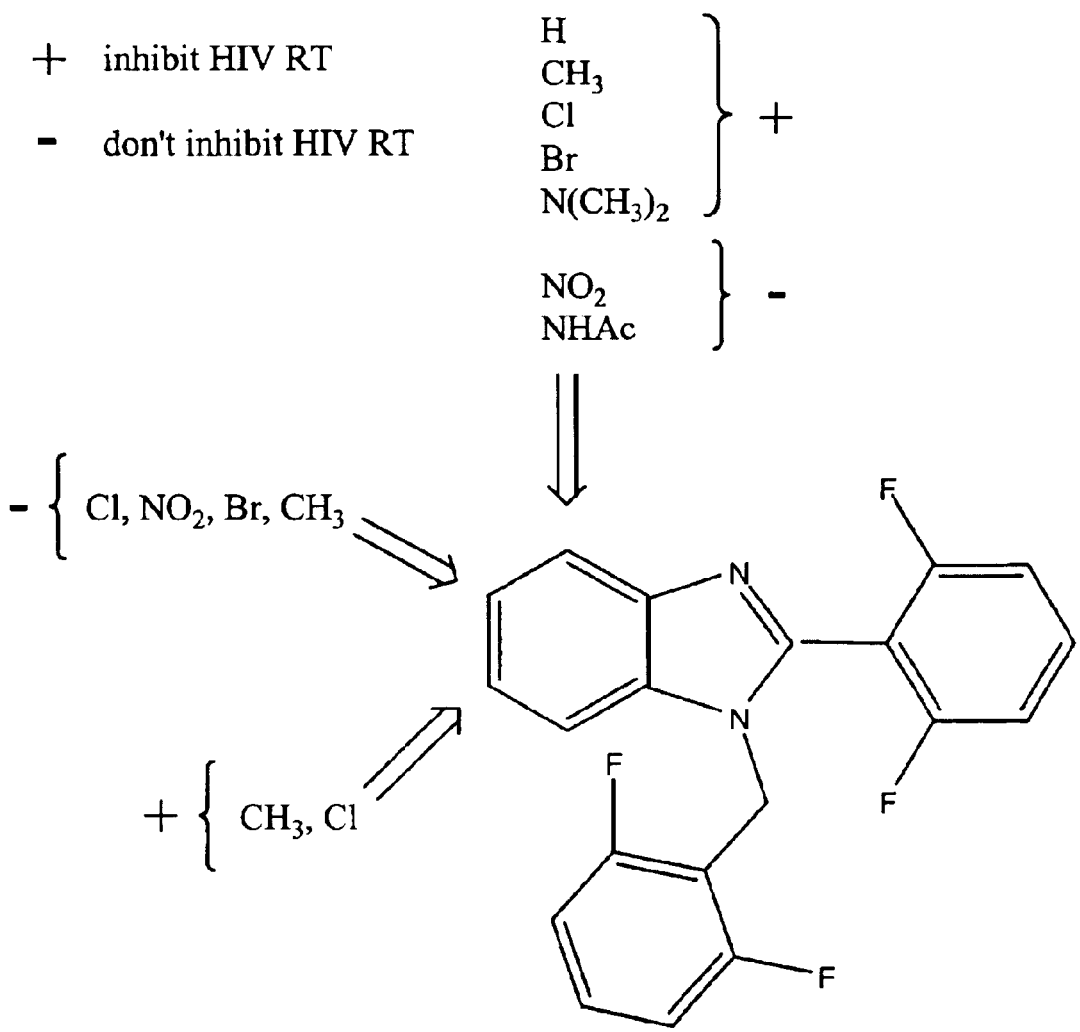
FIG. 6 shows the substituted benzimidazoles that inhibited HIV RT, as well as substituted benzimidazoles that did not inhibit HIV RT.
Figure 7:
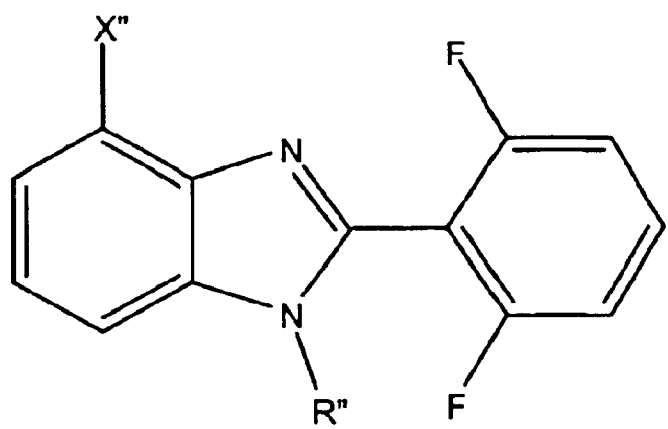
FIG. 7 (Panels A–B) shows the structure of 1- and 2-(2,6-difluorophenyl)benzimidazoles of the present invention.
Figure 7:
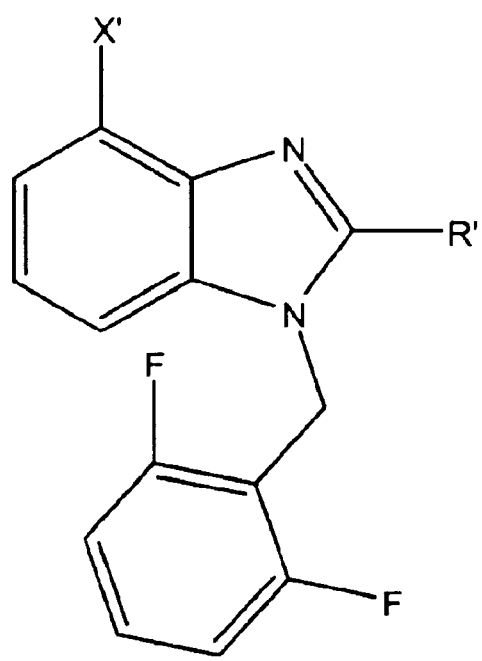

RT inhibition activity of previously described 5, 6, or 7-substituted 1-(2,6-difluorobenzyl)-2-(2,6-difluorophenyl) benzimidazole compounds show that substituents with H, $CH_3$, Cl, Br, and $N(CH_3)_2$ were found to inhibit HIV RT, while substitutions with $NO_2$, and NHAc did not inhibit the enzyme. These results are illustrated in FIG. 6. Although it is not necessary for an understanding of the present invention, it was determined that electron donating or halogen groups apparently increase RT inhibition activity, while electron withdrawing groups decrease inhibition activity.

Furthermore, it is apparent that substitution in the 4,6 positions gave increased RT inhibition activity compared to substitutions at the 5 or 7 positions. In addition, it was observed that substitutions of the 4 position with electron donating or halogen groups led to greater HIV RT inhibition than substitution at the 6 position. These results are summarized in FIGS. 16 and 17.

EXAMPLE 93

Preparation of N-(2,6-Difluorobenzoyl)-2,4-dimethyl-6-nitroanilide

To 4,6-Dimethyl-2-nitroaniline (4.25 g, 25.6 mmol) and was added 2,6-difluorobenzoyl chloride (4.25 mL, 33.80 mmol, 130 M %), and the reaction mixture was stirred for 5 h. Recrystallization of the crude product from ethylacetate/hexane (1:1) gave white crystals of N-(2,6-difluorobenzoyl)-2,4-dimethyl-6-nitroanilide (7.07 g, 90% yield). $^1$H NMR (200 MHz, $CD_2Cl_2$): δ 8.41 (br, 1H, NH), 7.68 (br d, J=2.6 Hz, 1H, $H_5$), 7.48 (m, 1H, $H_4$), 7.42 (d, J=2.6 Hz, 1H, $H_3$), 7.05 (m, 2H, $H_{3',5'}$), 2.42 (s, 3H, $CH_3$), 2.39 (s, 3H, $CH_3$).

EXAMPLE 94

Preparation of 2-(2,6-Difluorophenyl)-4,6-dimethylbenzimidazole

N-(2,6-Difluorobenzoyl)-2,4-dimethyl-6-nitroanilide (Example 93) (4.55 g, 14.9 mmol) was reacted with iron powder (3.45 g) for 0.5 h. Recrystallization of the crude product from diethylether/hexane (1:3) gave white crystals of 2-(2,6-difluorophenyl)-4,6-dimethylbenzimidazole (3.35 g, 12.97 mmol, 87% yield). $^1$H NMR (200 MHz, $CD_2Cl_2$): δ 9.69 (br, 1H, NH), 7.43 (bm, 1H,$H_4$), 7.26 (br s, $H_5$), 7.09 (m, 2$H_{3',5'}$), 6.95 (br s 1H, $H_7$), 2.59 (s, 3H, $CH_3$), 2.45 (s, 3H, $CH_3$).

EXAMPLE 95

Preparation of 1-(2,6-Difluorobenzyl)-2-(2,6-difluorophenyl)-4,6-dimethylbenzimidazole To 2-(2,6-difluorophenyl)-4,6-dimethylbenzimidazole (Example 94) (0.50 g, 1.94 mmol) was added 2,6-difluoro-α-bromotoluene (0.52 g, 2.51 mmol, 130 M %). Flash chromatography of the crude product eluting with 2% methanol/$CH_2Cl_2$, and recrystallization from hexane gave white crystals of 1-(2,6-difluorobenzyl)-2-(2,6-difluorophenyl)-4,6-dimethylbenzimidazole (0.68 g, 1.77 mmol, 91% yield). $^1$H NMR (200 MHz, $CD_2Cl_2$): δ 7.51 (cm, 1H, $H_4$), 7.23 (m, 1H, $H_{4''}$), 7.11 (m, 1H, $H_5$), 7.05 (cm, 2H, $H_{3',5'}$), 6.93 (m, 1H, $H_7$), 6.80 (cm, 2H, $H_{3'',5''}$), 5.29 (s, 2H, $CH_2PhF_2$), 2.58 (s, 3H, $CH_3$), 2.44 (s, 3H, $CH_3$).

EXAMPLE 96

Preparation of 1-(2,6-Difluorobenzyl)-2-(2,6-difluorophenyl)-4-(N-methylacetamido)-benzimidazole To 1-(2,6-difluorobenzyl)-2-(2,6-difluorophenyl)-4-acetamidobenzimidazole (Example 88) (2.44 g, 5.90 mmol) and methyl iodide (0.60 mL, 9.69 mmol) dissolved in THF (30 mL) was added excess NaH. After stirring overnight, the solution was concentrated to dryness, diluted with $CH_2Cl_2$, and washed with water, $NaHSO_4$(10% soln) and NaCl (sat. aq). The combined washings were dried ($Na_2SO_4$), filtered, and concentrated. The crude product was purified by flash chromatography eluting with 2% methanol in $CH_2Cl_2$, yielding 1-(2,6-Difluorobenzyl)-2-(2,6-difluorophenyl)-4-(N-methylacetamido)-benzimidazole (0.89 g, 2.08 mmol, 63% yield). M.p. 155–156° C. $^1$H NMR (200 MHz, $CD_2Cl_2$): δ 7.55 (m, 1H, $H_{4'}$), 7.48 (br d, J=7.4 Hz, 1H, $H_5$), 7.31 (dd, J=7.4, 7.7 Hz, 1H, $H_6$), 7.27 (m, 1H, $H_{4''}$), 7.14 (dd, J=1.1, 7.7 Hz, 1H, $H_7$), 7.09 (m, 2H, $H_{3',5'}$), 6.84 (m, 2H, $H_{3'',5''}$), 5.38 (s, 2H, $CH_2PhF_2$), 3.34 (s, 3H, $NCH_3$), 1.83 (s, 3H, NAc).

EXAMPLE 97

Preparation of 1-(2,6-Difluorobenzyl)-2-(2,6-difluorophenyl)-4-(N-methylamino)benzimidazole To 1-(2,6-difluorobenzyl)-2-(2,6-difluorophenyl)-4-(N-methylacetamido)-benzimidazole (Example 96) (0.50 g, 1.17 mmol) suspended in water (9.0 mL) was added HCl (1.0 mL). After 3 h at reflux, the solution was concentrated to dryness, diluted with ethylacetate, and washed with $NaHCO_3$ (sat. aq) and NaCl (sat. aq). The combined washings were dried ($Na_2SO_4$), filtered, and concentrated. The crude product was purified by flash chromatography eluting with 2% methanol in $CH_2Cl_2$, yielding 1-(2,6-Difluorobenzyl)-2-(2,6-difluorophenyl)-4-(N-methylamino)-benzimidazole (0.35 g, 78% yield). M.p. 194–195° C. $^1$H NMR (200 MHz, $CD_2Cl_2$): δ 7.52 (m, 1H, $H_{4'}$), 7.23 (m, 1H, $H_{4''}$), 7.13 (dd, J=8.3, 8.0 Hz, 1H, $H_6$), 7.07 (m, 2H, $H_{3',5'}$), 6.80 (m, 2H, $H_{3'',5''}$), 6.76 (d, J=8.3 Hz, 1H, $H_5$) 6.36 (d, J=8.0 Hz, 1H, $H_7$), 5.29 (s, 2H, $CH_2PhF_2$), 2.96 (s, 3H, $NCH_3$).

EXAMPLE 98

Preparation of 2,6-Difluorobenzoic Acid-(2-hydroxymethyl)-6-nitroanilide

To methyl N-(2,6-difluorobenzoyl)-6-nitro-2-anilidecarboxylate (4003, Example 43) (4.50 g, 13.4 mmol) dissolved in THF (50 mL) at 0° C. was added lithium aluminum hydride (0.50 g, 13.2 mmol, 100 M %). After 30 min, the reaction was allowed to warm to room temperature followed by a second addition of lithium aluminum hydride (0.20 g, 5.26 mmol, 40 M %) at 2 h. After 4 h, the reaction was concentrated and the residue was redissolved in EtOAc, and washed with $NaHSO_4$ (10% soln), $NaHCO_3$ (sat. aq), and NaCl (sat. aq). The combined washings were dried ($Na_2SO_4$), filtered, and evaporated. The crude product was purified by flash chromatograph eluting with 4% MeOH/$CH_2Cl_2$, and recrystallized from $CH_2Cl_2$ yielding white solids of 2,6-Difluorobenzoic acid-(2-hydroxymethyl)-6-nitroanilide (2.47 g, 8.01 mmol, 60% yield). $^1$H NMR (200 MHz, $CD_2Cl_2$): δ 7.92 (dd, J=1.4, 8.2 Hz, 1H, $H_5$), 7.79 (dd, J=1.4, 7.8 Hz, 1H, $H_3$), 7.54–7.43 (m, 2H, $H_{4'}$, $H_4$), 7.06 (m, 2H, $H_{3',5'}$), 4.74 (s, 2H, $CH_2O$).

EXAMPLE 99

Preparation of 2,6-Difluorobenzoic Acid-(2-acetoxymethyl)-6-nitroanilide

To 2,6-difluorobenzoic acid-(2-hydroxymethyl)-6-nitroanilide (Example 98) (6.00 g, 19.5 mmol) dissolved in THF (85 mL) and triethylamine (4.00 mL) was added acetic anhydide (4.00 mL, 42.4 mmol, 220 M %). After stirring overnight at room temperature, the reaction was concentrated. The residue was then redissolved in EtOAc, and washed with $NaHCO_3$ (sat. aq) and NaCl (sat. aq). The combined washings were dried ($Na_2SO_4$), filtered, and evaporated. The crude product was purified by flash chromatograph eluting with 4% MeOH/$CH_2Cl_2$ and titrated from $Et_2O$, yielding white solids of 2,6-difluorobenzoic acid-(2-acetoxymethyl)-6-nitroanilide (5.09 g, 14.5 mmol, 75% yield). $^1$HNMR (200 MHz, $CD_2Cl_2$): δ 9.16 (br, 1H, NH), 7.99 (dd, J=1.5, 8.3 Hz, 1H, $H_5$), 7.79 (dd, J=1.5, 7.7 Hz, 1H, $H_3$), 7.50 (m, 1H, $H_{4'}$), 7.49 (dd, J=7.7, 8.3 Hz, 1H, $H_4$), 7.06 (m, 2H, $H_{3',5'}$), 5.20 (s, 2H, $CH_2O$), 2.09 (s, 3H, OAc).

EXAMPLE 100

Preparation of Methyl 2-(2,6-difluorophenyl)benzimidazole-4-carboxylate

Methyl N-(2,6-difluorobenzoyl)-6-nitro-2-anilidecarboxylate (4003, Example 43) (30.38 g, 90.35 mmol) and iron powder (30.80 g) were refluxed for 0.5 h. Recrystallization of the crude product from EtOAc gave white crystals of methyl 2-(2,6-difluorophenyl)-benzimidazole-4-carboxylate (18.47 g, 64.07 mmol, 71% yield). $^1$H-NMR (200 MHz, $CD_2Cl_2$): δ 10.92 (br, 1H, NH), 8.06 (d, J=8.1 Hz, 1H, $H_5$), 7.97 (d, J=7.7 Hz, 1H, $H_7$), 7.49 (m, 1H, $H_{4'}$), 7.37 (dd, J=7.7,8.1 Hz, $H_6$), 7.13 (m, 2H, $H_{3',5'}$), 4.01 (s, 3H, $CO_2CH_3$).

EXAMPLE 101

Preparation of 2-(2,6-Difluorophenyl)-4-acetoxymethylbenzimidazole 2,6-Difluorobenzoic acid-2-(acetoxymethyl)-6-nitroanilide (Example 99) (2.82 g, 8.05 mmol) and iron powder (2.50 g) were refluxed for 0.5 h. The crude product was purified using flash chromatography with 2% methanol/$CH_2Cl_2$, and tritrated from 3:1 $Et_2O$:hexane, to give white crystals of 2-(2,6-difluorophenyl)-4-acetoxymethylbenzimidazole (1.83 g, 6.05 mmol, 75% yield). $^1$H-NMR (200 MHz, $CD_2Cl_2$): δ 10.64 & 9.97$_{(rotamers)}$ (br, 1H, NH), 7.83 (m, 1H), 7.45 (m, 1H, $H_{4'}$), 7.29 (m, 2H), 7.13 (m, 2H, $H_{3',5'}$), 5.61& 5.46$_{(rotamers)}$ (s, 2H, $CH_2O$), 2.11 (s, 3H, Ac).

EXAMPLE 102

Preparation of Methyl 1-(2,6-difluorobenzyl)-2-(2,6-difluorophenyl)benzimidazole-4-carboxylate Methyl 2-(2,6-difluorophenyl)benzimidazole-4-carboxylate (Example 100) (16.15 g, 56.0 mmol) and 2,6-difluorobenzyl bromide (14.67 g, 70.86 mmol, 125 M %) were reacted. The crude product was purified using flash chromatography eluting with 2% methanol/$CH_2Cl_2$ and recrystallization from diethylether, yielding white crystals of methyl 1-(2,6-difluorobenzyl)-2-(2,6-difluorophenyl)benzimidazole-4-carboxylate (17.63 g, 42.55 mmol, 76% yield). M.p. 184–186° C. $^1$H NMR (200 MHz, $CD_2Cl_2$): δ 7.94 (dd, J=1.1, 7.6 Hz, 1H, $H_5$), 7.72 (dd, J=1.1, 8.2 Hz, 1H, $H_7$), 7.56 (m, 1H, $H_{4'}$), 7.37 (dd, J=7.6, 8.2 Hz, 1H, $H_6$), 7.26 (m, 1H, $H_{4''}$), 7.09 (m, 2H, $H_{3',5'}$), 6.82 (m, 2H, $H_{3'',5''}$), 5.39 (s, 2H, $CH_2PhF_2$), 3.95 (s, 3H, $CO_2CH_3$).

EXAMPLE 103

Preparation of 1-(2,6-Difluorobenzyl)-2-(2,6-difluorophenyl)-4-acetoxymethylbenzimidazole 2-(2,6-Difluorophenyl)-4-acetoxymethylbenzimidazole (Example 101) (3.55 g, 11.74 mmol) and 2,6-difluorobenzylbromide (3.40 g, 16.4 mmol, 140 M %) were reacted. The crude product was purified using flash chromatography eluting with 2% methanol/$CH_2Cl_2$ and recrystallization from diethylether, yielding white crystals of 1-(2,6-difluorobenzyl)-2-(2,6-difluorophenyl)-4-acetoxymethylbenzimidazole (5.94 g, 13.9 mmol, 76% yield). M.p. 126–127° C. $^1$HNMR (300 MHz, $CD_2Cl_2$): δ 7.54 (m, 1H, $H_{4'}$), 7.48 (m, 1H, $H_6$), 7.33–7.27 (m, 2H, $H_{5,7}$), 7.25 (m, 1H, $H_{4''}$), 7.08 (m, 2H, $H_{3',5'}$), 6.82 (m, 2H, $H_{3'',5''}$), 5.54 (s, 2H, $CH_2PhF_2$), 5.36 (s, 2H, $CH_2O$), 2.08 (s, 3H, OAc).

EXAMPLE 104

Preparation of 1-(2,6-Difluorobenzyl)-2-(2,6-difluorophenyl)-4-hydroxylbenzimidazole To 1-(2,6-difluorobenzyl)-2-(2,6-difluorophenyl)-4-methoxylbenzimidazole (Example 46) (0.30 g, 0.78 mmol) and hexadecyltrimethylammonium bromide (0.30 g) dissolved in acetic acid (9.0 mL) was added HBr (1.0 mL). After refluxing for 7 h, the reaction was concentrated. The residue was then diluted with EtOAc, and washed with $NaHCO_3$ (sat. aq) and NaCl (sat. aq). The combined washing were dried ($Na_2SO_4$), filtered, and concentrated. The crude product was purified by flash chromatography eluting with 2% methanol/$CH_2Cl_2$ and recrystallization from diethylether, yielding 1-(2,6-Difluorobenzyl)-2-(2,6-difluorophenyl)-4-hydroxyl-benzimidazole (0.25 g, 0.67 mmol, 86% yield). M.p. 257–259° C. $^1$H NMR (200 MHz, $CD_2Cl_2$): δ 7.57 (m, 1H, $H_{4'}$), 7.25 (m, 1H, $H_{4''}$), 7.17 (dd, J=7.9, 8.3 Hz, 1H, $H_6$), 7.12 (m, 2H, $H_{3',5'}$), 6.99 (d, J=8.3 Hz, 1H, $H_7$), 6.82 (m, 2H, $H_{3'',5''}$), 6.73 (dd, J=7.9, 1.0 Hz, $H_5$), 5.35 (s, 2H, $CH_2PhF_2$).

EXAMPLE 105

Preparation of 1-(2,6-Difluorobenzyl)-2-(2,6-difluorophenyl)benzimidazole-4-carbonitrile To methyl 1-(2,6-difluorobenzyl)-2-(2,6-difluorophenyl)benzimidazole-4-carboxylate (Example 102) (1.02 g, 2.46 mmol) suspended in xylene (60 mL) was added freshly prepared 1.0 M $AlMe_2NH_2$ (20 mL). After 3 h at reflux, the reaction was concentrated. The residue was redissolved in $CH_2Cl_2$ and washed with $NaHSO_4$ (10% soln), $NaHCO_3$ (sat. aq) and NaCl (sat. aq). The combined washings were dried ($Na_2SO_4$), filtered and concentrated. The crude product was purified by flash chromatography eluting with 2% methanol/$CH_2Cl_2$ and recrystallization from diethylether/hexane (3:1), yielding white crystals of 1-(2,6-Difluorobenzyl)-2-(2,6-difluorophenyl)-benzimidazole-4- carbonitrile (1.72 g, 4.51 mmol, 61% yield). M.p. 156–157° C.; $^1$H NMR (200 MHz, CD$_2$Cl$_2$): δ 7.76 (dd, J=1.0, 8.6 Hz, 1H, H$_5$), 7.63 (dd, J=1.0, 7.6 Hz, 1H, H$_7$), 7.58 (m, 1H, H$_{4'}$), 7.37 (dd, J=7.6, 8.6 Hz, 1H, H$_6$), 7.28 (m, 1H, H$_{4''}$), 7.11 (m, 2H, H$_{3',5'}$), 6.83 (m, 2H, H$_{3'',5''}$), 5.40 (s, 2H, CH$_2$PhF$_2$).

EXAMPLE 106

Preparation of N-Hydroxy 1-(2,6-difluorobenzyl)-2-(2,6-difluorophenyl)benzimidazole-4-carboxamidine To 1-(2,6-Difluorobenzyl)-2-(2,6-difluorophenyl) benzimidazole-4-carbonitrile (Example 105) (0.60 g, 1.57 mmol) dissolved in ethanol (15 mL) and triethylamine (0.5 mL) was added hydroxylamine (0.14 g, 130 M %). After 24 h at reflux, the reaction was concentrated. The residue was redissolved in CH$_2$Cl$_2$ and washed with NaHSO$_4$(10% soln), NaHCO$_3$ (sat. aq) and NaCl (sat. aq). The combined washings were dried (Na$_2$SO$_4$), filtered and concentrated. The crude product was purified by flash chromatography eluting with 4% methanol/CH$_2$Cl$_2$ and recrystallization from methanol, yielding white crystals of N-hydroxy 1-(2, 6-difluorobenzyl)-2-(2,6-difluorophenyl)benzimidazole-4-carboxamidine (0.57 g, 1.37 mmol, 87% yield). M.p. 214–216° C. $^1$H NMR (200 MHz, CD$_2$Cl$_2$): δ 7.84 (dd, J=1.1, 7.7 Hz, 1H, H$_5$), 7.57 (m, 1H, H$_{4'}$), 7.54 (dd, J=1.1, 8.2 Hz, 1H, H$_7$), 7.30 (dd, J=7.7, 8.2 Hz, 1H, H$_6$), 7.28 (m, 1H, H$_{4''}$), 7.11 (m, 2H, H$_{3',5'}$), 6.83 (m, 2H, H$_{3'',5''}$), 6.61 (br, 2H, NH$_2$), 5.39 (s, 2H, CH$_2$PhF$_2$).

EXAMPLE 107

Preparation of 1-(2,6-difluorobenzyl)-2-(2,6-difluorophenyl)benzimidazole-4-carboxylic Acid Amide To 1-(2,6-Difluorobenzyl)-2-(2,6-difluorophenyl) benzimidazole-4-carbonitrile (Example 105) (1.10 g, 2.88 mmol) dissolved in ethanol (100 mL) and 3 M Na$_2$CO$_3$ (10 mL) was added 30% hydrogen peroxide (10 mL). After stirring overnight at room temperature, the reaction was concentrated. The residue was then redissolved in EtOAc, and washed with NaHSO$_4$(10% soln), NaHCO$_3$ (sat. aq) and NaCl (sat. aq). The combined washings were dried (Na$_2$SO$_4$), filtered and concentrated. The crude product was purified by flash chromatography eluting with 2% methanol/CH$_2$Cl$_2$ and recrystallization from methanol, yielding white crystals of 1-(2,6-difluorobenzyl)-2-(2,6-difluorophenyl) benzimidazole-4-carboxylic acid amide (0.83 g, 2.08 mmol, 72% yield). M.p. 260–261° C. $^1$H-NMR (200 MHz, CD$_2$Cl$_2$): δ 8.10 (dd, J=1.1, 7.7 Hz, 1H, H$_5$), 7.71 (br d, J=8.1 Hz, 1H, H$_7$), 7.59 (m, 1H, H$_{4'}$), 7.43 (dd, J=7.7, 8.1 Hz, 1H, H$_6$), 7.28 (m, 1H, H$_{4''}$), 7.13 (m, 2H, H$_{3',5'}$), 6.84 (m, 2H, H$_{3'',5''}$), 5.43 (s, 2H, CH$_2$PhF$_2$), 1.92 (s, 2H, NH$_2$).

EXAMPLE 108

Preparation of 1-(2,6-difluorobenzyl)-2-(2,6-difluorophenyl)benzimidazole-4-carboxylic Acid Dimethylamide To 1-(2,6-difluorobenzyl)-2-(2,6-difluorophenyl) benzimidazole-4-carboxylic acid amide (Example 107) (1.10 g, 2.88 mmol) and methyl iodide (0.12 mL) suspended in THF (5 mL) was added sodium hydride (0.15 g). After stirring overnight at room temperature, the reaction was diluted with EtOAc and washed with NaHSO$_4$(10% soln), NaHCO$_3$ (sat. aq) and NaCl (sat. aq). The combined washings were dried (Na$_2$SO$_4$), filtered and concentrated. The crude product was purified by flash chromatography eluting with 5% methanol/CH$_2$Cl$_2$, yielding white crystals of 1-(2, 6-difluorobenzyl)-2-(2,6-difluorophenyl)benzimidazole-4-carboxylic acid dimethylamide (0.20 g, 0.47 mmol, 90% yield). M.p. 213–214° C. $^1$H NMR (300 MHz, CD$_2$Cl$_2$): δ 7.59–7.43 (m, 2H, H$_{4',5}$), 7.36–7.20 (m, 3H, H$_{6,7,4''}$), 7.08 (m, 2H, H$_{3',5'}$), 6.83 (m, 2H, H$_{3'',5''}$), 5.37 (s, 2H, CH$_2$PhF$_2$), 3.12 (s, 3H, CH$_3$), 2.88 (s, 3H, CH$_3$).

EXAMPLE 109

Preparation of 1-(2,6-Difluorobenzyl)-2-(2,6-difluorophenyl)benzimidazole-4-carboxylate To methyl 1-(2,6-difluorobenyl)-2-(2,6-difluorophenyl) benzimidazole-4-carboxylate (Example 102) (1.02 g, 2.46 mmol) dissolved in methanol (20 mL) was added barium hydroxide (1.20 g). After 2 h, acetic acid was added and the reaction concentrated. The residue was redissolved in CH$_2$Cl$_2$ and washed with NaHCO$_3$ (sat. aq) and NaCl(sat. aq). The combined washings were dried (Na$_2$SO$_4$), filtered and concentrated. The crude product was purified by flash chromatography eluting with 8% methanol/CH$_2$Cl$_2$ and recrystallization from diethylether/hexane (3:1), yielding white crystals of 1-(2,6-Difluorobenzyl)-2-(2,6-difluorophenyl)benzimidazole-4-carboxylate (0.71 g, 1.77 mmol, 72% yield). M.p. 178–180° C. $^1$H-NMR (200 MHz, CD$_2$Cl$_2$): δ 8.06 (d, J=7.8 Hz, 1H, H$_5$), 7.76 (d, J=8.1 Hz, 1H, H$_7$), 7.62 (m, 1H, H$_{4'}$), 7.47 (dd, J=7.8, 8.1 Hz, 1H, H$_6$), 7.29 (m, 1H, H$_{4''}$), 7.14 (m, 2H, H$_{3',5'}$), 6.85 (m, 2H, H$_{3'',5''}$), 5.45 (s, 2H, CH$_2$PhF$_2$).

EXAMPLE 110

Preparation of 1-(2,6-Difluorobenzyl)-2-(2,6-difluorophenyl)-4-benzimidazoyl-2-propanol To methyl 1-(2,6-difluorobenyl)-2-(2,6-difluorophenyl) benzimidazole-4-carboxylate (Example 102) (1.02 g, 2.46 mmol) suspended in THF (5 mL) was added 1.4 M methyl lithium (0.95 mL). After 0.5 h, the reaction was diluted with EtOAc and washed with NaHSO$_4$ (10% soln) and NaCl(sat. aq). The combined washings were dried (Na$_2$SO$_4$), filtered and concentrated. The crude product was purified by flash chromatography eluting with 1:1 ethylacetate/hexane and recrystallization from hexane, yielding white crystals of 1-(2,6-Difluorobenzyl)-2-(2,6-difluorophenyl)-4-benzimidazoyl-2-propanol (0.11 g, 0.27 mmol, 55% yield). M.p. 149–150° C. $^1$H-NMR (200 MHz, CD$_2$Cl$_2$): δ 7.55 (m, 1H, H$_{4'}$), 7.48 (d, J=8.1 Hz, 1H, H$_5$), 7.25 (m, 2H, H$_{6,4''}$), 7.16 (dd, J=1.1, 7.6 Hz, 1H, H$_7$), 7.10 (m, 2H, H$_{3',5'}$), 6.82 (m, 2H, H$_{3'',5''}$), 5.82 (s, 1H, OH), 5.37 (s, 2H, CH$_2$PhF$_2$), 1.67 (s, 6H, CH$_3$). Anal. (C$_{23}$H$_{18}$F$_4$N$_2$O) C,H,N.

EXAMPLE 111

Preparation of 1-(2,6-Difluorobenzyl)-2-(2,6-difluorophenyl)-4-isopropenylbenzimidazole To 1-(2,6-Difluorobenzyl)-2-(2,6-difluorophenyl)-4-benzimidazoyl-2-propanol (Example 110) (0.45 g, 1.09 mmol) was added to H$_2$SO$_4$ (1.00 mL). After 15 min. at room temperature, the reaction was diluted with EtOAc, and washed with NaHCO$_3$ (sat. aq) and NaCl (sat. aq). The combined washings were dried (Na$_2$SO$_4$), filtered and concentrated. The crude product was purified by flash chromatography eluting with 1% MeOH/CH$_2$Cl$_2$ and recrystallization from diethylether/hexane (3:1), yielding white crystals of 1-(2,6-Difluorobenzyl)-2-(2,6-difluorophenyl)-4- isopropenylbenzimidazole (0.11 g, 0.28 mmol, 30% yield). M.p. 156–158° C. $^1$H-NMR (200 MHz, CD$_2$Cl$_2$): δ 7.53 (m, 1H, H$_{4'}$), 7.44–7.16 (cm, 4H, H$_{4'',5,6,7}$), 7.07 (m, 2H, H$_{3',5'}$), 6.81 (m, 2H, H$_{3'',5''}$), 6.03 (dq, J=0.8, 2.4 Hz, 1H, vinyl), 5.37 (s, 2H, CH$_2$PhF$_2$), 5.36 (dq, J=1.5, 2.4 Hz, 1H, vinyl), 2.33 (dd, J=0.8, 1.5 Hz, 3H, CH$_3$).

EXAMPLE 112

Preparation of 1-(2,6-Difluorobenzyl)-2-(2,6-difluorophenyl)-4-hydroxymethylbenzimidazole To 1-(2,6-difluorobenzyl)-2-(2,6-difluorophenyl)-4-acetoxymethylbenzimidazole (Example 103) (1.45 g, 3.38 mmol) dissolved in methanol (19 mL) and water (1.0 mL) was added K$_2$CO$_3$ (0.40 g). After 30 min, the reaction was concentrated, redissolved in EtOAc, and washed with NaHSO$_4$ (10% soln) and NaCl (sat. aq). The combined washings were dried (Na$_2$SO$_4$), filtered, and concentrated. Recrystallization of the crude product from diethylether:hexane (3:1) yielded white crystals of 1-(2,6-Difluorobenzyl)-2-(2,6-difluorophenyl)-4-hydroxymethyl-benzimidazole (1.25 g, 3.24 mmol, 96% yield). M.p. 157–158° C. $^1$H-NMR (300 MHz, CD$_2$Cl$_2$): δ 7.54 (m, 1H, H$_{4'}$), 7.43 (d, J=7.9 Hz, 1H, H$_7$), 7.30–7.22 (m, 2H, H$_{6,4''}$), 7.18 (d, J=7.5 Hz, 1H, H$_5$), 7.09 (m, 2H, H$_{3',5'}$), 6.82 (m, 2H, H$_{3'',5''}$), 5.37 (s, 2H, CH$_2$PhF$_2$), 5.06 (d, J=5.4 Hz, 2H, CH$_2$O), 3.51 (t, J=5.4 Hz, 1H, OH).

EXAMPLE 113

Preparation of 1-(2,6-Difluorobenzyl)-2-(2,6-difluorophenyl)-benzimidazole-4-carbaldehyde To CrO$_3$ (1.26 g) dissolved in pyridine (1.0 mL) and CH$_2$Cl$_2$ (9.0 mL) was added 1-(2,6-difluorobenzyl)-2-(2,6-difluorophenyl)-4-hydroxylmethylbenzimidazole (Example 112) (0.49 g, 1.27 mmol) dissolved in pyridine:CH$_2$Cl$_2$ (1:1) (2 mL). After stirring for 6 h, the reaction was filtered. The filtrate was diluted with CH$_2$Cl$_2$, and washed with NaHCO$_3$ (sat. soln) and NaCl (sat. aq). The combined washings were dried (Na$_2$SO$_4$), filtered, and concentrated. The crude product was purified by flash chromatography eluting with 1% methanol/CH$_2$Cl$_2$. Recrystallization from diethylether:hexane (3:1) yielded white crystals of 1-(2,6-Difluorobenzyl)-2-(2,6-difluorophenyl)-benzimidazole-4-carbaldehyde (0.38 g, 0.99 mmol, 78% yield). M.p. 151–153° C. $^1$H-NMR (300 MHz, CD$_2$Cl$_2$): δ 10.82 (d, J=0.6 Hz, 1H, CHO), 7.83 (dd, J=7.5, 1.1 Hz, 1H, H7), 7.78 (dd, J=8.1, 1.1 Hz, H5), 7.58 (m, 1H, H$_{4'}$), 7.44 (ddd, J=8.1, 7.5, 0.6 Hz, 1H, H$_6$), 7.27 (m, 1H, H$_{4''}$), 7.11 (m, 2H, H$_{3',5'}$), 6.84 (m, 2H, H$_{3'',5''}$), 5.42 (s, 2H, CH$_2$PhF$_2$).

EXAMPLE 114

Preparation of 1-(2,6-Difluorobenzyl)-2-(2,6-difluorophenyl)-4-chloromethylbenzimidazole To 1-(2,6-difluorobenzyl)-2-(2,6-difluorophenyl)-4-hydroxylmethyl-benzimidazole (Example 112) (0.54 g, 1.40 mmol) dissolved in CHCl$_3$ (3.0 mL) was added SOCl$_2$ (0.15 mL, 2.06 mmol, 150 M %). After 3 h at room temperature, the reaction was diluted with CHCl$_3$, and washed with NaHCO$_3$ (sat. soln) and NaCl (sat. aq). The combined washings were dried (Na$_2$SO$_4$), filtered and concentrated. The product was purified by flash chromatography eluting with 1% MeOH/CH$_2$Cl$_2$. Recrystallization from diethylether:hexane (3:1) yielded white crystals of 1-(2,6-difluorobenzyl)-2-(2,6-difluorophenyl)-4-chloromethylbenzimidazole (0.52 g, 1.28 mmol, 92% yield). M.p. 143–144° C. $^1$H-NMR (300 MHz, CD$_2$Cl$_2$): δ 7.55 (m, 1H, H$_{4'}$), 7.48 (dd, J=7.7, 1.1 Hz, 1H, H$_7$), 7.36 (dd, J=7.6 Hz, 1.1 Hz, 1H, H$_5$), 7.30 (dd, J=7.7, 7.6 Hz, 1H, H$_6$), 7.25 (m, 1H, H$_{4''}$), 7.09 (m, 2H, H$_{3',5'}$), 6.82 (m, 2H, H$_{3'',5''}$), 5.36 (s, 2H, CH$_2$PhF$_2$), 5.07 (s, 2H, CH$_2$Cl).

EXAMPLE 115

Preparation of 1-(2,6-Difluorobenzyl)-2-(2,6-difluorophenyl)benzimidazol-4-yl-azidomethyl To 1-(2,6-Difluorobenzyl)-2-(2,6-difluorophenyl)-4-chloromethylbenzimidazole (Example 114) (1.31 g, 3.23 mmol) dissolved in DMF (10 mL) was added sodium azide (0.68 g, 10.5 mmol, 325 M %). After 1 h at room temperature, the reaction was diluted with CH$_2$Cl$_2$, and washed with NaHCO$_3$ (sat. soln) and NaCl (sat. aq). The combined washings were dried (Na$_2$SO$_4$), filtered and concentrated. Recrystallization from diethylether:hexane (3:1) yielded white crystals of 1-(2,6-difluorobenzyl)-2-(2,6-difluorophenyl)benzimidazol-4-yl-azidomethyl (1.23 g, 2.99 mmol, 93% yield). M.p. 150–152° C. $^1$H-NMR (300 MHz, CD$_2$Cl$_2$): δ 7.55 (m, 1H, H$_{4'}$), 7.50 (dd, J=7.7, 1.6 Hz, 1H, H$_7$), 7.32 (m, 1H, H$_6$), 7.30 (m, 2H, H$_{5,4''}$), 7.09 (m, 2H, H$_{3',5'}$), 6.82 (m, 2H, H$_{3'',5''}$), 5.37 (s, 2H, CH$_2$PhF$_2$), 4.81 (s, 2H, CH$_2$N$_3$).

EXAMPLE 116

Preparation of 1-(2,6-Difluorobenzyl)-2-(2,6-difluorophenyl)benzimidazol-4-yl-methylamine To 1-(2,6-Difluorobenzyl)-2-(2,6-difluorophenyl) benzimidazol-4-yl-azidomethyl (Example 115) (0.55 g, 1.34 mmol) dissolved in acetic acid (10 mL) was added zinc (0.55 g, 6.27 mmol, 630 M %). After 1 h at room temperature, the reaction was concentrated, redissolved with EtOAc, and washed with NaHCO$_3$(sat. soln) and NaCl(sat. aq). The combined washings were dried(Na$_2$SO$_4$), filtered and concentrated to give the crude product. The crude product was purified by flash chromatography eluting with 4% MeOH/CH$_2$Cl$_2$ increasing to 100% MeOH, yielding white crystals of 1-(2,6-difluorobenzyl)-2-(2,6-difluorophenyl) benzimidazol-4-yl-methylamine (0.16 g, 0.42 mmol, 31% yield). M.p. 257–260° C.; $^1$H-NMR (300 MHz, CD$_2$Cl$_2$): δ 7.59 (m, 1H, H$_{4'}$), 7.55 (m, 1H, H$_7$), 7.35 (m, 2H, H$_{5,6}$), 7.27 (m, 1H, H$_{4''}$), 7.12 (m, 2H, H$_{3',5'}$), 6.83 (m, 2H, H$_{3'',5''}$), 5.40 (s, 2H, CH$_2$PhF$_2$), 4.49 (s, 2H, CH$_2$N).

EXAMPLE 117

Preparation of N-1-(2,6-Difluorobenzyl)-2-(2,6-difluorophenyl)-benzimidazol-4-methyl)-acetamide To 1-(2,6-Difluorobenzyl)-2-(2,6-difluorophenyl) benzimidazol-4-yl-methylamine (Example 116) (0.28 g, 0.73 mmol) dissolved in THF (10 mL) and triethylamine (0.2 mL) was added acetic anhydride (0.20 mL, 2.12 mmol, 300 M %). After 1.5 h at room temperature, the reaction was concentrated, redissolved with EtOAc, and washed with NaHCO$_3$(sat. soln) and NaCl (sat. aq). The combined washings were dried (Na$_2$SO$_4$), filtered, and concentrated. The crude product was purified by flash chromatography eluting with 4% MeOH/CH$_2$Cl$_2$ increasing to 8% MeOH/CH$_2$Cl$_2$, yielding white crystals of N-1-(2,6-difluorobenzyl)-2-(2,6-difluorophenyl)-benzimidazol-4-methyl)-acetamide (0.20 g (0.47 mmol, 65% yield). M.p. 178–179° C. $^1$H-NMR (300 MHz, CD$_2$Cl$_2$): δ 7.56 (m, 1H, H$_{4'}$), 7.42 (m, 1H, H$_7$), 7.30–7.18 (m, 3H, H$_{5,6,4''}$), 7.10 (m, 2H, H$_{3',5'}$), 6.90 (br, 1H, NH), 6.82 (m, 2H, H$_{3'',5''}$) 5.37 (s, 2H, CH$_2$PhF$_2$), 4.79 (d, J=5.9 Hz, 2H, CH$_2$N), 1.92 (s, 3H, NAc).

EXAMPLE 118

Preparation of 1-(2,6-Difluorobenzyl)-2-(2,6-difluorophenyl)-4-(N-acetyl-N-methyl)-aminomethylbenzimidazole To N-1-(2,6-Difluorobenzyl)-2-(2,6-difluorophenyl)-benzimidazol-4-methyl)-acetamide (Example 117) (0.25 g, 0.58 mmol) and methyl iodide (0.065 mL, 1.04 mmol, 180 M %) dissolved in THF (10 mL) was added sodium hydride (50 mg, 1.25 mmol, 215 M %). After stirring overnight at room temperature, the reaction was diluted with EtOAc, and washed with NaHSO$_4$ (10% soln) and NaCl (sat. aq). The combined washings were dried(Na$_2$SO$_4$), filtered, and concentrated. The crude product was purified by flash chromatography eluting with 2% MeOH/CH$_2$Cl$_2$ increasing to 4% MeOH/CH$_2$Cl$_2$, yielding white crystals of 1-(2,6-Difluorobenzyl)-2-(2,6-difluorophenyl)-4-(N-acetyl-N-methyl)-aminomethylbenzimidazole (0.24 g, 0.54 mmol, 94% yield). M.p. 171–172° C. $^1$H-NMR (300 MHz, CD$_2$Cl$_2$): δ 7.55 (m, 1H, H$_4$), 7.44 & 7.40 (rotamers) (d, J=8.3 Hz, 1H, H$_7$), 7.32–7.20 (m, 2H), 7.15–7.04 (m, 3H), 6.82 (m, 2H, H$_{3'',5''}$), 5.37 & 5.35 (rotamers) (s, 2H, CH$_2$PhF$_2$), 5.00 & 4.98 (rotamers) (s, 2H, CH$_2$N), 3.04 & 2.96 (rotamers) (s, 3H, NCH$_3$), 2.15 & 2.11 (rotamers) (s, 3H, NAc).

EXAMPLE 119

Preparation of 1-(2,6-Difluorobenzyl)-2-(2,6-difluorophenyl)benzimidazol-4-yl-methoxymethyl To 1-(2,6-difluorobenzyl)-2-(2.6-difluorophenyl)-4-hydroxymethyl-benzimidazole (Example 112) (0.20 g, 0.52 mmol) dissolved in THF (2 mL) was added methyl iodide (40 mL, 0.64 mmol, 120 M %) and sodium hydride (20 mg). After 2 h at room temperature, additional methyl iodide (20 mL, 0.32 mmol, 60 M %) was added. After 3 h, the reaction was diluted with EtOAc, and washed with NaHCO$_3$ (sat. soln) and NaCl (sat. aq). The combined washings were dried (Na$_2$SO$_4$), filtered and concentrated. The crude product was purified by flash chromatography eluting with 2% MeOH/CH$_2$Cl$_2$, yielding white crystals of 1-(2,6-difluorobenzyl)-2-(2,6-difluorophenyl)benzimidazol-4-yl-methoxymethyl (0.10 g, 0.25 mmol, 48% yield). $^1$H-NMR (300 MHz, CD$_2$Cl$_2$): δ 7.53 (m, 1H, H$_4$), 7.43 (dd, J=7.1, 2.2 Hz, 1H, H$_7$), 7.34–7.28 (m, 2H, H$_{5,6}$), 7.24 (m, 1H, H$_{4''}$), 7.08 (m, 2H, H$_{3',5'}$), 6.81 (m, 2H, H$_{3'',5''}$), 5.35 (s, 2H, CH$_2$PhF$_2$), 4.90 (s, 2H, CH$_2$O), 3.45 (s, 3H, OCH$_3$).

EXAMPLE 120

Preparation of 4-Azidomethyl-2-(2,6-difluorobenzyl)-1-(2,6-difluorophenyl)benzimidazole To a solution of 1-(2,6-difluorobenzyl)-2-(2,6-difluorophenyl)-4-chloromethylbenzimidazole (Example 114) (125 mg, 0.31 mmole) in 0.7 mL of acetonitrile (not completely soluble) was added 5.9 mg (0.022 mmole) of 18-crown-6 ether, followed by 20 mg (0.31 mmole) of potassium cyanide. The reaction mixture was diluted with 0.4 mL of dry methanol, and stirred for 24 hrs at room temperature. The reaction mixture was then diluted with methylene chloride (2 mL), filtered, washed with water, and the solution was dried over anhydrous sodium sulfate. The solvent was evaporated and the residue was chromatographed on silica gel column eluted with 1:1 hexane/ethyl acetate, yielding 4-azidomethyl-2-(2,6-difluorobenzyl)-1-(2,6-difluorophenyl)benzimidazole (57 mg, 47% yield).

From the above, it is clear that the present invention provide compositions and methods for the treatment of HIV infection. In particular, the present invention provides non-nucleoside inhibitors of reverse transcriptase (RT). In particular, the present invention relates to stable analogues of 1-(2,6-difluorophenyl)-1H,3H-thiazolo[3,4-a]benzimidazole, effective in the inhibition of human immunodeficiency virus (HIV) RT, with particular activity against HIV-1 RT. Furthermore, the present invention provides highly purified compositions with high activity against HIV-1 RT mutants that are refractory to inhibition with other non-nucleoside HIV-1 RT compounds.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. A method for treating human immunodeficiency virus infection, comprising the steps of:
   a) providing: i) a subject suspected of being infected with human immunodeficiency virus; and ii) a composition having anti-reverse transcriptase activity and comprising at least one substituted benzimidazole having a 2,6-difluorobenzyl substituent at the N-1 site of said benzimidazole;
   b) administering said composition to said subject; and
   c) observing for indicators of said anti-reverse transcriptase inhibition activity.

2. The method of claim 1, wherein said human immunodeficiency virus is HIV-1.

3. The method of claim 1, wherein said substituted benzimidazole further comprises a 2,6-difluorophenyl substituent at the C2 site of said benzimidazole.

4. The method of claim 1, wherein said substituted benzimidazole is of the general structure:

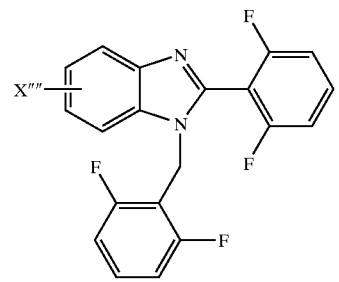

wherein X'''' is at least one substituent positioned at a benzimidazole carbon selected from C4, C5, C6, C7, C4 and C5, and C4 and C6 of a substituted 1-(2,6-difluorobenzyl)-2-(2,6-difluorophenyl)benzimidazole, and wherein said X'''' is selected from the group consisting of hydrogen, 4-methyl, 5-methyl, 6-methyl, 7-methyl, 4,5-dimethyl, 4,6-dimethyl, 4-ethyl, 4-cyano (CN), 4-methylenecyano (CH$_2$CN), 4-methoxy, 4-nitro, 5-nitro, 4-amino, 4-N-acetamido (NHAc), 4-N-methylamino (NHCH$_3$), 4-N-dimethylamino (N(CH$_3$)$_2$), 4-isopropyl, 4-isoprenyl, 4-bromo, 5-bromo, 6-bromo, 4-chloro, 5-chloro, 6-chloro, fluoro, N-methylacetamido (NAcCH$_3$), methyl carboxylate (CO$_2$Me), methyl acetamido ester (CH$_2$OAc), hydroxy, CNH(NH$_2$OH), amide (CONH$_2$), N-dimethylamide (CON(CH$_3$)$_2$), carboxylic acid, hydroxymethyl (CH$_2$OH), formyl, chloromethyl, 4-methyleneazido (CH$_2$N$_3$), aminomethyl (CH$_2$NH$_2$), N-acetamidomethyl (CH$_2$NHAc), CH$_2$NCH$_2$Ac, dimethyl ether (CH$_2$OCH$_3$), 4-methylenethiocyanate (CH$_2$NCS), and 4-methyleneacetylene (CH$_2$CCH).

5. The method of claim 4, wherein said X"" is selected from the group consisting of hydrogen, 4-methyl, 4-ethyl, 4-cyano, 4-methoxy, 4-nitro, 4-amino, 4-N-acetamido, 4-N-methylamino, 4-N-dimethylamino, 4-isopropyl, 4-isopropenyl, 4-bromo, 4-chloro, 4-methyleneazido, 4-methylenecyano, 4-methylenethiocyanate, and 4-methyleneacetylene.

6. The method of claim 5, wherein said X"" is selected from the group consisting of 4-methoxy, 4-methyleneazido, and 4-methylenecyano.

7. A method for inhibiting HIV-1 reverse transcriptase, comprising the steps of:

a) providing: i) a sample suspected of being infected with HIV-1 virus; and ii) a composition having anti-reverse transcriptase activity and comprising at least one substituted benzimidazole, having a 2,6-difluorobenzyl substituent at the N-1 site of said benzimidazole;

b) administering said composition to said sample; and c) observing for indicators of said anti-reverse transcriptase inhibition activity.

8. The method of claim 7, wherein said substituted benzimidazole further comprises a 2,6-difluorophenyl substituent at the C2 site of said benzimidazole.

9. The method of claim 7, wherein said substituted benzimidazole is of the general structure:

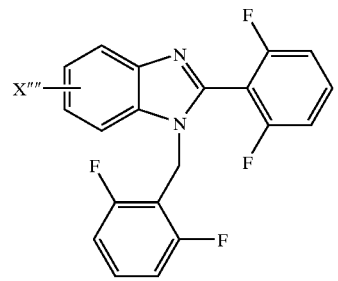

wherein X"" is at least one substituent positioned at a benzimidazole carbon selected from C4, C5, C6, C7, C4 and C5, and C4 and C6 of a substituted 1-(2,6-difluorobenzyl)-2-(2,6-difluorophenyl)benzimidazole, and wherein said X"" is selected from the group consisting of hydrogen, 4-methyl, 5-methyl, 6-methyl, 7-methyl, 4,5-dimethyl, 4,6-dimethyl, 4-ethyl, 4-cyano (CN), 4-methylenecyano (CH$_2$CN), 4-methoxy, 4-nitro, 5-nitro, 4-amino, 4-N-acetamido (NHAc), 4-N-methylamino (NHCH$_3$), 4-N-dimethylamino (N(CH$_3$)$_2$), 4-isopropyl, 4-isoprenyl, 4-bromo, 5-bromo, 6-bromo, 4-chloro, 5-chloro, 6-chloro, fluoro, N-methylacetamido (NAcCH$_3$), methyl carboxylate (CO$_2$Me), methyl acetamido ester (CH$_2$OAc), hydroxy, CNH(NH$_2$OH), amide (CONH$_2$), N-dimethylamide (CON(CH$_3$)$_2$), carboxylic acid, hydroxymethyl (CH$_2$OH), formyl, chloromethyl, 4-methyleneazido (CH$_2$N$_3$), aminomethyl (CH$_2$NH$_2$), N-acetamidometbyl (CH$_2$NHAc), CH$_2$NCH$_2$Ac, dimethyl ether (CH$_2$OCH$_3$), 4-methylenethiocyanate (CH$_2$NCS), and 4-methyleneacetylene (CH$_2$CCH).

10. The method of claim 9, wherein said X"" is selected from the group consisting of hydrogen, 4-methyl, 4-ethyl, 4-cyano, 4-methoxy, 4-nitro, 4-amino, 4-N-acetamido, 4-N-methylamino, 4-N-dimethylamino, 4-isopropyl, 4-isopropenyl, 4-bromo, 4-chloro, 4-methyleneazido, 4-methylenecyano, 4-methylenethiocyanate, and 4-methyleneacetylene.

11. The method of claim 10, wherein said X"" is selected from the group consisting of 4-methoxy, 4-methyleneazido, and 4-methylenecyano.

* * * * *